US010961516B2

(12) United States Patent
Hong et al.

(10) Patent No.: US 10,961,516 B2
(45) Date of Patent: Mar. 30, 2021

(54) PROLINE HYDROXYLASE AND USES THEREOF

(71) Applicants: ASYMCHEM LABORATORIES (TIANJIN) CO., LTD., Tianjin (CN); ASYMCHEM LIFE SCIENCE (TIANJIN) CO., LTD., Tianjin (CN); TIANJIN ASYMCHEM PHARMACEUTICALS CO., LTD., Tianjin (CN); ASYMCHEM LABORATORIES (FUXIN) CO., LTD., Liaoning (CN); JILIN ASYMCHEM LABORATORIES CO., LTD., Jilin (CN)

(72) Inventors: Hao Hong, Tianjin (CN); Gage James, Tianjin (CN); Jiangping Lu, Tianjin (CN); Na Zhang, Tianjin (CN); Wenyan Yu, Tianjin (CN); Fang Liu, Tianjin (CN); Yanjun Li, Tianjin (CN); Xin Huang, Tianjin (CN); Juan Gao, Tianjin (CN); Kejian Zhang, Tianjin (CN); Yulei Ma, Tianjin (CN); Junlu Wei, Tianjin (CN)

(73) Assignees: ASYMCHEM LABORATORIES (TIANJIN) CO., LTD., Tianjin (CN); ASYMCHEM LIFE SCIENCES (TIANJIN) CO., LTD., Tianjin (CN); TIANJIN ASYMCHEM PHARMACEUTICALS CO., LTD., Tianjin (CN); ASYMCHEM LABORATORIES (FUXIN) CO., LTD., Fuxin (CN); JILIN ASYMCHEM LABORATORIES CO., LTD., Jilin (CN)

( * ) Notice: Subject to any disclaimer, the term of this patent is extended or adjusted under 35 U.S.C. 154(b) by 0 days.

(21) Appl. No.: 16/344,779

(22) PCT Filed: Nov. 4, 2016

(86) PCT No.: PCT/CN2016/104670
§ 371 (c)(1),
(2) Date: Apr. 24, 2019

(87) PCT Pub. No.: WO2018/082030
PCT Pub. Date: May 11, 2018

(65) Prior Publication Data

US 2020/0199544 A1 Jun. 25, 2020

(51) Int. Cl.

| | |
|---|---|
| *C12N 9/02* | (2006.01) |
| *C12N 15/70* | (2006.01) |
| *C12N 15/81* | (2006.01) |

(52) U.S. Cl.
CPC .......... *C12N 9/0071* (2013.01); *C12N 15/70* (2013.01); *C12N 15/81* (2013.01); *C12Y 114/11002* (2013.01)

(58) Field of Classification Search
None
See application file for complete search history.

(56) References Cited

FOREIGN PATENT DOCUMENTS

| | | | |
|---|---|---|---|
| CN | 104928311 | A | 9/2015 |
| CN | 105713883 | A | 6/2016 |
| EP | 2290065 | A1 | 3/2011 |
| EP | 3358016 | A1 | 8/2018 |
| WO | 2013169725 | A2 | 11/2013 |

OTHER PUBLICATIONS

PCT, "International Search Report", Application No. PCT/CN2016/104670, dated Aug. 9, 2017, 8 pages.
NCBI Reference Sequence, "hypothetical protein[Kordia jejudonensis]" May 11, 2015.
Extended European Search Report issued in European Patent Application No. 16920642.2 dated May 15, 2020 (7 pages).

*Primary Examiner* — Paul J Holland
(74) *Attorney, Agent, or Firm* — Dorsey & Whitney LLP

(57) ABSTRACT

Provided are a proline hydroxylase and uses thereof. The proline hydroxylase comprises (a) a protein having the amino acid sequence as shown in SEQ ID NO: 2; (b) a protein having an amino acid sequence of SEQ HD NO: 2 with a mutation of one or more amino acids and having a proline hydroxylase activity; or (c) a protein retaining the mutation of one or more amino acids as in (b), and having the proline hydroxylase activity and having at least 78% homology with the amino acid sequence of the protein in (b). Protein having the amino acid sequence as shown in SEQ HD NO: 2 and mutants obtained by genetically engineering have higher catalytic specificity or significantly increased catalytic activity when compared to proline hydroxylases in prior art.

6 Claims, 1 Drawing Sheet

Specification includes a Sequence Listing.

PROLINE HYDROXYLASE AND USES THEREOF

SEQUENCE LISTING

The instant application contains a Sequence Listing, which has been submitted electronically in ASCII format and is hereby incorporated by reference in its entirety. Said ASCII file was created 23 Apr. 2019, is named "20190424_P281926WOUS01_371Appln_SL.txt", is 533 bytes in size, and contains a sequence listing identical to the sequence listing filed in the corresponding international application no. PCT/CN2016/104670 created and filed on 4 Nov. 2016.

TECHNICAL FIELD

The application relates to genetic engineering and enzyme engineering, and in particular, to a proline hydroxylase and uses thereof.

BACKGROUND

A derivative of proline is an important structure unit of pharmaceutical synthesis, especially hydroxyproline which belongs to rare amino acid in the nature world, and is a starting raw material for synthesis of many important pharmaceuticals. According to different proline hydroxylation positions and space structures, there are eight isomers of the hydroxyproline totally, herein 3-hydroxy-L-proline and 4-hydroxy-L-proline are used as the important raw materials of multiple pharmaceuticals of antibiotics, enzyme inhibitors, antineoplastics, antihypertensive agents and new-type stomach medicines and the like, and are a hot point of existing biosynthesis research. In addition, the hydroxyproline may be a source of a natural product or chemical synthesis, for example, the hydroxyproline may be a plant material or a hydrolysate of collagen, or use allyl bromide, diethyl acetaminopropionic acid, D-glutamic acid and Beta-alanine as the starting raw materials for performing the chemical synthesis.

Similarly, the derivative L-hydroxypiperidine acid of the hydroxyproline is also the important structure unit of the pharmaceutical synthesis, and is an important intermediate of the synthesis of a Beta-lactamase inhibitor and a TNF-A invertase inhibitor. The L-hydroxypiperidine may be prepared through separation of plants or other natural materials or through a chemical synthesis method similarly. But a complicated separating and purifying method or a complicated synthesis process is needed, and it is difficult to realize large-scale industrial production. A mode of performing hydroxylation on piperidine acid through hydroxylase is an ideal method for acquiring the hydroxypiperidine acid. Enzyme frequently applied at present is the proline hydroxylase, it is a type of ketoglutarate-dependent dioxygenase, and A-oxoglutarate and $O_2$ are needed as a common substrate, and iron ions are used as a cofactor.

Many microorganisms contain the proline hydroxylase, for example, *Sinorhizobium meliloti, Streptomyces* sp. strain THI, and Glarea lozoyensis. Three types of frequently-used cis-form-proline-3-hydroxylase, cis-form-proline-4-hydroxylase and anti-form-proline-4-hydroxylase may respectively catalyze L-proline to generate cis-form-3-hydroxy-L-proline, cis-form-4-hydroxy-L-proline and anti-form-4-hydroxy-L-proline. But in a catalytic reaction of the proline hydroxylase to the proline and the proline derivative, some inevitable problems are existent, for example, a conversion rate is low, and a position isomer is generated by catalysis, the large-scale industrial production may not be realized. After the cis-form-proline-4-hydroxylase from the *Sinorhizobium meliloti* is genetically modified, the conversion rate of L-piperidine acid hydroxylation and specificity of enzyme catalysis are greatly improved, but 10% of the position isomer (2S,3R)-3-hydroxypiperidine-2-carboxylic acid is still generated (W02013169725A2). So, it has important significance to industrial synthesis of the hydroxyproline and the derivative thereof that a type of the enzyme capable of specifically and rapidly catalyzing the hydroxylation of the proline and the proline derivative is found out.

SUMMARY

A main purpose of the application is to provide a proline hydroxylase and uses thereof, and solve the problem of poor selectivity of proline hydroxylation enzyme catalysis in the prior art.

In order to realize the above purpose, according to one aspect of the application, a proline hydroxylase is provided, the proline hydroxylase comprises: (a) a protein having an amino acid sequence as shown in SEQ ID NO: 2; (b) a protein having an amino acid sequence of SEQ HD NO: 2 with a mutation of one or more amino acids and having a proline hydroxylase activity; or (c) a protein retaining the mutation of one or more amino acids as in (b), and having the proline hydroxylase activity and having at least 78% homology with the amino acid sequence of the protein in (b).

Further, a site of the mutation is selected from one or more of the group consisting of H14, S16, T25, F26, E27, D30, S33, E34, Y35, S37, I39, W40, K41, D54, H55, S57, I58, K86, T91, F95, C97, I98, K106, F111, K112, K162, L166, I118, H119, I120, K123, T130, D134, V135, S154, N165, D173, K209, I223 and S225.

Further, the mutation comprises any one or more of the group consisting of: H14R, S16N, T25G, T25R, F26L, E27K, D30S, S33N, E34N, E34G, E34L, E34S, E34D, Y35W, Y35K, S37W, S37F, S37E, S37N, S37T, S37C, I39K, I39R, W40F, K41E, D54G, H55Q, S57L, I58T, I58Y, I58A, I58R, I58V, I58S, I58C, K86P, T91A, F95Y, C97Y, I98V, K106V, K106T, K106Q, F111S, K112E, K112R, S154A, K162E, L166M, I118F, I118V, I118R, H119R, H119F, I120V, K123D, K123N, K123Q, K123S, K123I, K123T, T130N, D134G, V135K, N165H, D173G, K209R, I223V, and S225A.

Further, the mutation comprises any one of combinations selected from the group consisting of: E27K+Y35W/K, E27K+I39K/R, E27K+K123D/I/Q/S, E27K+N165H, 139K/R+Y35W/K, I39K/R+K123D/I/Q/S, 139K/R+N165H, K123D+W40F, K123D+Y35W/K, E27K+I39K/R+K123D/I/Q/S, K123D/I/Q/S+N 165H, S37C/E/F/N/W/T+I223V, E27K+Y35W/K+I39K/R, E27K+S37C/E/F/N/W/T+I39K/R E27K+E34N/G/L/D/S+I39K/R, E27K+I39K/R+D30S, E27K+I39K/R+I118F/V/R, E27K+I39K/R+I98V, S37C/E/F/N/W/T+I223V+N165H, Y35W/K+S37C/E/F/N/W/T+W40F, S37C/E/F/N/W/T+I223V+K123D/I/Q/S, E27K+I39K+Y35W/K+S37C/E/F/N/W/T, E27K+I39K/R+S37C/E/F/N/W/T+K123D/I/Q/S, E27K+I39K/R+K106Q+K112E, E27K+I39K/R+Y35W/K+S37C/E/F/N/W/T+K123D/I/Q/S, E27K+I39K/R+S37C/E/F/N/W/T+I58A/C/R/S/T/V/Y, E27K+S37C/E/F/N/W/T+I223V+K123D/I/Q/S, S37C/E/F/N/W/T+I39K/R+I223V+K123D/I/Q/S, E27K+S37C/E/F/N/W/T+I39K/R+K123D/I/Q/S+I98V, E27K+S37C/E/F/N/W/T+I39K/R+K123D/I/Q/S+I223V, F26L+E27K+I39K/R+K123D/I/Q/S, I223V+S37C/E/F/N/W/T+E27K+I39K/R, I223V+S37C/E/F/N/W/T+E27K+N165H, E27K+S37C/E/F/N/W/T+I39K/R+I98V+K123D/I/Q/S+I223V, K106Q+K112E+I223V, E27K+S37C/E/F/N/W/T+I39K/R+I58A/C/R/S/T/V/Y+K123D/I/Q/S, E27K+I39K/R+K123D/I/Q/S+N165H, H14R+E34G+K106Q+K112E+I223V, T25G/R+E27K+S37C/E/F/N/W/T+I39K/R+I58A/C/R/S/T/V/Y, E27K+S37C/E/F/N/W/T+I39K/R+I58A/C/R/S/T/V/Y+K86P, K123D/I/Q/S+Y35W/K+I120V, E27K+D30S+I39K/R+I58A/C/R/S/T/V/Y+K112E, S37C/E/F/N/W/T+I39K/R+N165H, E27K+E34N/G/L/D/S+I39K/R+I58A/C/R/S/T/V/Y+1223V, E27K+S37C/E/F/N/W/T+I39K/R+I58A/C/R/S/T/V/Y+D173G, E27K+S37C/E/F/N/W/T+I39K/R+I58A/C/R/S/T/V/Y+D173G+I118F/V/R, E27K+E34N/G/L/D/S+S37C/E/F/N/W/T+I39K/R+I58A/C/R/S/T/V/Y, E27K+E34N/G/L/D/S+S37C/E/F/N/W/T+I39K/R+I58A/C/R/S/T/V/Y+D173G, E27K+S37C/E/F/N/W/T+I39K/R+I58A/C/R/S/T/V/Y+D173G+K123D/I/Q/S, E27K+S37C/E/F/N/W/T+I39K/R+I58A/C/R/S/T/V/Y+D173G+K123D/I/Q/S+I118F/V/R, E27K+S37C/E/F/N/W/T+I39K/R+I58A/C/R/S/T/V/Y+D1736+K123D/I/Q/S+N165H, E27K+E34N/G/L/D/S+S37C/E/F/N/W/T+I39K/R+I58A/C/R/S/T/V/+D173G+K123D/I/Q/S, H14R+E27K+D30S+E34N/G/L/D/S+I39K/R+I98V+K106V/T/Q+K112E/R+I223V, T25G/R+E27K+S37C/E/F/N/W/T+I39K/R+I58A/C/R/S/T/V/Y+D173G+K123D/I/Q/S+I118 F/V/R+N165H, H14R+E27K+E34N/G/L/D/S+I39K/R+I98V+K106V/T/Q+K112E/R+I223V, H14R+E27K+E34N/G/L/D/S+S37C/E/F/N/W/T+I39K/R+I98V+K106V/T/Q+K112E/R+I223 V, H14R+E27K+E34N/G/L/D/S+Y35W/K+I39K/R+I98V+K106V/T/Q+K112E/R+I223V, H14R+E27K+E34N/G/L/D/S+I39K/R+I98V+K106V/T/Q+K112E/R+K123D/I/Q/S+I223V, H14R+E27K+E34N/G/L/D+139K/R+I58A/C/R/S/T/V/Y+198V+K106V/T/Q+K112E/R+I223V and H14R+E27K+E34N/G/L/D/S+I39K/R+I98V+K106V/T/Q+K112E/R+I118F/V/R+I223V, wherein, '/' represents 'or'.

In order to realize the above purpose, according to one aspect of the application, a DNA molecule is provided, wherein the DNA molecule encodes any one of the proline hydroxylase.

In order to realize the above purpose, according to another aspect of the application, a recombinant vector is provided, wherein the recombinant vector is connected with the DNA molecule.

Further, the recombinant vector is selected from one of the group consisting of: pET-21b(+), pET-22b(+), pET-3a(+), pET-3d(+), pET-11a(+), pET-12a(+), pET-14b(+), pET-15b (+), pET-16b(+), pET-17b(+), pET-19b(+), pET-20b(+), pET 21a(+), pET-23a(+), pET-23b(+), pET-24a(+), pET-25b(+), pET-26b(+), pET-27b(+), pET-28a(+), pET-29a(+), pET-30a (+), pET-31b(+), pET-32a(+), pET-35b(+), pET-38b(+), pET-39b(+), pET-40b(+), pET-41a(+), pET-41b(+), pET-42a (+), pET-43a(+), pET-43b(+), p-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwinl, pEZZ18, pKK232-18, pUC-18 and pUC-19.

According to another aspect of the application, a host cell is provided, wherein the host cell comprises any one of the recombinant vectors.

Further, the host cell is a prokaryotic cell or a eukaryocyte, preferably the eukaryocyte is a yeast cell.

Further, the host cell is a competent cell, preferably the competent cell is an *E. coli* BL21 cell or an *E. coli* W3110 cell.

According to another aspect of the application, a method for producing an L-hydroxyproline derivative is provided, wherein the method comprises: using an L-proline derivative as a substrate, and applying any one of the proline hydroxylases to catalyze hydroxylation of the substrate, to obtain the L-hydroxyproline derivative as shown in a general formula (I);

(I)

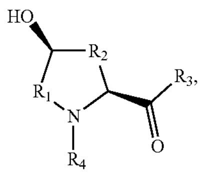

Wherein $R_1$ is selected from $C_1$-$C_5$ alkylene or $C_2$-$C_5$ alkenylene; $R_2$ is selected form $C_0$-$C_4$ alkylene or $C_2$-$C_4$ alkenylene; $R_3$ is selected from hydroxyl, amino, $C_1$-$C_6$ alkoxy, aryloxy, $C_1$-$C_6$ alkyl sulfenyl or $C_1$-$C_6$ aryl sulfenyl; and $R_4$ is selected from hydrogen, $C_1$-$C_6$ alkyl, $C_2$-$C_6$ alkenyl or $C_2$-$C_6$ alkynyl.

Further, the method comprises: using α-oxoglutarate and $O_2$ as a common substrate, using iron ions as a cofactor, applying the proline hydroxylase to catalyze hydroxylation of the substrate, to obtain the L-hydroxyproline derivative.

Further, the L-hydroxyproline derivative is cis-4-hydroxy-L-proline or (2S,5S)-5-hydroxypiperidine-2-carboxylic acid.

Further, the proline hydroxylase catalyzes hydroxylation of the substrate in a temperature of 5~45 DEG C., preferably 5~15 DEG C., to obtain the L-hydroxyproline derivative as shown in the general formula (I).

By means of the technical solutions of the present application, by selecting SEQ ID NO: 2 as a base sequence, a mutant containing single or multiple amino acid residues modified through genetic engineering, or by altering other amino acid residues while retaining these mutations, a protein of which modified amino acid sequence having at least 78% homology with the amino acid sequence in (b), has a higher catalytic specificity (namely selectivity) than the proline hydroxylases in prior art, or has remarkably improved catalytic activity when compared with the wild-type hydroxylases (namely the proline hydroxylase having the amino acid sequence of SEQ ID NO: 2) discovered by the application.

BRIEF DESCRIPTION OF THE DRAWINGS

The accompanying drawings of the specification, which constitute a part of the application, are used for providing further understanding to the present application. The exemplary embodiments of the present application and illustration thereof are used for explaining the present application, instead of constituting improper limitation to the present application. In the accompanying drawings.

DETAILED DESCRIPTION OF THE EMBODIMENTS

Figure 1:
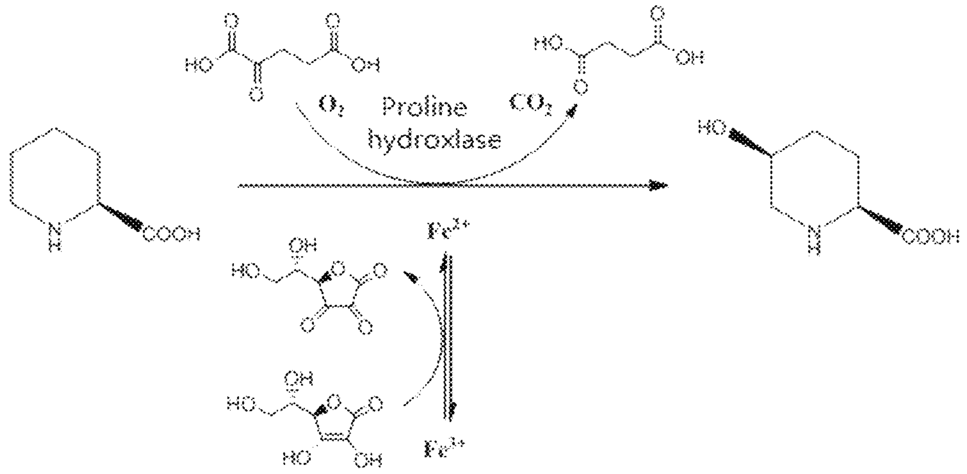
FIG. 1 shows a chemical reaction of a use of a proline hydroxylase according to the present application in catalytic-synthesizing (2S,5S)-5-hydroxypiperidine-2-carboxylic acid (or named as cis-5-hydroxypiperidine acid)

It needs to be noted that the embodiments in the invention and the characteristics in the embodiments may be combined with each other if there is no conflict. The present invention will be expounded hereinafter with reference to the accompanying drawings and in conjunction with the embodiments.

Term Explanation:

Selectivity of enzyme: or named as specificity of enzyme, it is the selectivity of the enzyme to a substrate in a catalytic biochemical reaction. In the application, the selectivity of a proline hydroxylase refers to the extent to which the proline hydroxylase catalyzes hydroxylation of an L-proline derivative to obtain a L-hydroxyproline derivative of a particular configuration. In the reaction related to the application, the extent of catalytic selectivity of the hydroxylase may be characterized with reacted diastereomeric excess.

Conversion rate: it is a percentage or a fraction of conversion of a certain reactant. The conversion rate is an index for representing a reaction extent of the reactant. The conversion rate of hydroxylation of L-piperidine acid in the application is a percentage of a product (2S,5S)-5-hydroxypiperidine-2-carboxylic acid generated in a reaction of catalyzing L-piperidine acid through hydroxylase or proline hydroxylase accounting for the L-piperidine acid in a system.

Catalytic activity: refers to the amount of reactant conversion per unit volume (or mass) of catalyst per unit time. In the present application, the catalytic activity of the proline hydroxylase is positively correlated with the conversion of the reaction.

Evolution: creating molecular diversity by means of mutations or recombination, and screening the diversity to obtain a gene or DNA with new functions. In the present application, the hydroxylase or the proline hydroxylase is modified through the means of mutations or recombination, to obtain the hydroxylase or the proline hydroxylase with improved performance.

Diastereoisomer: it is a stereoisomer of which molecules have two or more chiral centers, and the molecules are in a non-mirrored relationship.

Diastereomeric excess (de % for short): it is used for representing excess of one diastereomer to other enantiomers in the two chiral centers. Namely de %=(R,R+S,S)−(S,R+R,S)/(R,R+S,S+S,R+R,S).

Wild type: it is obtained from the nature, and is not artificially mutagenized or modified. In the application, the wild type proline hydroxylase is a natural proline hydroxylase screened from Genebank and is encoded by a gene sequence not artificially modified.

Homologous sequence: refers to a DNA sequence that is identical or similar between different individuals of the same species or the different species.

In the application, related 1 wt refers to an 1 g proline hydroxylase variant recombined wet cell needed for converting an 1 g main raw material.

As mentioned in the background, a defect of the proline hydroxylase in the prior art is that the catalytic selectivity is not high, and difficulty is increased for separation of a follow-up target product. In order to solve the problem in the prior art that the selectivity of the proline hydroxylase is not high, inventors acquire a proline hydroxylase with high catalytic specificity through genetic engineering. At the same time, the inventors perform various mutation modifications on the wild-type proline hydroxylase in prior art, in order to obtain a proline hydroxylase with high selectivity and improved catalytic activity.

The inventors screens countless homologous sequences of the amino acid sequence of the proline hydroxylase in prior art from Genebank, according to the order of homology from high to low, gene mutations in different positions were performed on various screened homologous sequences, and the hydroxylase activities of various mutants were screened. It was discovered that the activity of the proline hydroxylase of the mutant obtained by performing the mutation on the sequence with higher homologous with the proline hydroxylase in prior art sequences has no apparent difference with the proline hydroxylase in prior art. Finally, only one sequence derived from *Kordia jejudonensis* which has the lowest homology (only about 30%) with the amino acid sequence of the proline hydroxylase in prior art was left, and the sequence has no specific gene function annotation in the Genebank, and is annotated as a hypothetical protein. Recombination expression was performed on the sequence by means of genetic engineering, it was unexpectedly discovered that a protein encoded by the sequence has the activity of the proline hydroxylase, and has the selectivity higher than that of the proline hydroxylase in the prior art. The protein is named as the wild-type proline hydroxylase by the inventors. The application further performs a mutation test on the amino acid sequence of the wild-type proline hydroxylase, it is more surprised that the mutant obtained by the mutation of the sequence derived from *Kordia jejudonensis* not only has the activity of the proline hydroxylase, but also the catalytic activity thereof is remarkably improved compared with the wild-type proline hydroxylase.

Further, the inventors perform various mutation screening based on the sequence, and finally it was discovered that multiple mutation sites are related to the activity of the proline hydroxylase. Under the precondition of retaining these mutation sites, the activity of the proline hydroxylase is not apparently affected by arbitrarily changing the mutations of other sites.

On the above basis, the inventors performed a deeper research, and some important amino acid residue sites were discovered, after the mutation of the sites, soluble expression of the proline hydroxylase thereof is decreased significantly or the catalytic activity of the proline hydroxylase is lost. After S3, L94, H105, D107, S131, E132, Y137, M139, W145, H153, N157, V167, D169 amino acid residue sites are mutated to the other majority of amino acids, the soluble expression of the proline hydroxylase is decreased significantly, some are zero even. The mutations of these amino acids affect folding of the proline hydroxylase, so the soluble expression of the proline hydroxylase in an *E. coli* host cell is significantly decreased, and even the soluble expression is decreased to zero. The mutated amino acid of the proline hydroxylase may be selected from: Y35A, Y35F, Y355, W40Y, L94A, L94G, L945, F95A, F95W, H105R, H105Q, H105E, H105G, R117A, R117P, R117K, P121V, V135A, S131T, H153Y, H153A, H153R, H153K. At the same time, it is further discovered that after the Y32, R93, R117, Y108 amino acid residue sites are mutated to the other majority of the amino acids, the catalytic activity of the proline hydroxylase is lost. These mutated amino acids which are capable of significantly decreasing, even losing the catalytic activity of proline hydroxylase may be selected from: Y32N, Y32V, Y32V, Y320, Y32E, Y325, Y32R, Y32D, Y32R, Y321, Y32P, Y35H, Y35F, Y35A, W40Y, R93K, R93H, R93E, R93A, L94A, F95W, F95A, H105E, H105Q, H105R, H105K, H105A, K106H, D107A, Y108W, Y108A, Y108L, Y108S, R117D, R117P, R117N, R117N, R117H, R117K, R117A, P121V, H153W, H153F, H153K, H153R, H153A.

Computer simulation was performed on a three-dimensional structure of the proline hydroxylase, and a simulated three-dimensional structure diagram was obtained. After the structure diagram was analyzed, it was speculated that most of these sites should be the important amino acid residues for participating in combination of the proline hydroxylase with a substrate or combination with a cofactor, for example, H105, D107, and H153 may participate in the combination of the cofactor with the proline hydroxylase. And for example, Y32, R93, and R117 may participate in the combination of the substrate with the proline hydroxylase, herein R93 and R117 amino acid residues may form a salt bridge with the substrate. In addition, the amino acid residues at 230-276 are outside an activity relevant area of the enzyme, so modifying or removing some of the amino acids in the area does not have a significant effect on the activity of the proline hydroxylase.

The mutants of the application are the mutants with improved catalytic activity or selectivity which are obtained by modifying the rest amino acids in the case of keeping the above amino acid sites having significant effects on the activity of the proline hydroxylase unchanged.

On the basis of the above research results, the inventors provide the technical solution of the application. In a typical embodiment, a proline hydroxylase is provided, wherein the proline hydroxylase comprises: (a) a protein having an amino acid sequence as shown in SEQ ID NO: 2; (b) a protein having an amino acid sequence of SEQ HD NO: 2 with a mutation of one or more amino acids and having a proline hydroxylase activity; or (c) a protein retaining the mutation of one or more amino acids as in (b), and having the proline hydroxylase activity and having at least 78% homology with the amino acid sequence of the protein in (b).

The above proline hydroxylase, through selecting SEQ ID NO:2 as a base sequence, a mutant containing single or multiple amino acid residues modified through genetic engineering, or by altering other amino acid residues while retaining these mutations, a protein of which modified amino acid sequence having at least 78% homology with the amino acid sequence in (b), has a higher catalytic specificity (namely selectivity) than the proline hydroxylase in prior art, or has remarkably improved catalytic activity when compared with the wild-type hydroxylase (namely the proline hydroxylase having the amino acid sequence of SEQ ID NO: 2) discovered by the application.

The catalytic activity of the above proline hydroxylase is at least improved by 1 time, 2 times, 3 times, 4 times, 5 times or more compared with the original wild type hydroxylase encoded by the SEQ ID NO:2. In addition, the selectivity of the above proline hydroxylase is remarkably improved compared with the prior art, the diastereomeric excess of the (2S,5S)-5-hydroxypiperidine-2-carboxylic acid catalytically generated by the proline hydroxylase is greater than 90%, 91%, 92%, 93%, 94%, 95%, 96%, 97%, 98%, 99% or more.

In some embodiments, the above proline hydroxylase is the protein having the amino acid sequence of SEQ ID NO:2 with the mutation of one or more of the following amino acid sites and having the proline hydroxylase activity: H14, S16, T25, F26, E27, D30, S33, E34, Y35, S37, I39, W40, K41, D54, H55, S57, 158, K86, T91, F95, C97, I98, K106, F111, K112, K162, L166, I118, H119, I120, K123, T130, D134, V135, S154, N165, D173, K209, I223 and S225. Wherein, the amino acid sites related to the proline hydroxylase activity are as follows: H14, S16, F26, E27, D30, S33, E34, S37, I39,W40, K41, T91, F95, C97, I98, K106, F111, K112, I118, H119, I120, K123, T130, D134, V135, N165, K209 and I223. In addition, Y35 and S57 amino acid sites relate to the selectivity of the hydroxylase. The mutation of the above one or more amino acid sites has remarkable effects on the activity or selectivity of the wild type proline hydroxylase, and is capable of remarkably improving the proline hydroxylase catalytic activity and/or selectivity of the mutant.

The three-dimensional structure simulated diagram of the above proline hydroxylase was further analyzed, it was speculated that the active sites of the proline hydroxylase in the application are located in a Beta folding related region, and the region is fixed by an A helical structure positioned in the N-terminal and C-terminal. The substrate combination site is positioned in a center of the Beta folding area, and adjacent to a cofactor combination area. These sites are analyzed, and it was discovered that the mutated amino acid residues of the proline hydroxylase referred in the application are mainly positioned in the substrate combination sites or the region related to the cofactor combination in the three-dimensional structure simulated diagram of the proline hydroxylase. For example, E27, D30, S33, E34, Y35, S37, I39, W40, K41, H55, S57, 158, F95, C97, I98, F111, K112, I118, H119, and I120 amino acids may be positioned near the substrate combination sites, and specificity of the substrate combination may be improved through the modification of these amino acids, so the activity or catalytic selectivity of the enzyme is improved. For example, K106, L166, K123, D134, S154, N165 amino acids may be positioned near the cofactor combination sites, the modification of these amino acids may improve the combination of the cofactor, and coordinate the utilization and transmission of oxygen, so the activity of the enzyme is improved.

On the basis of the mutation of the above sites, through mutating these sites to different amino acids and detecting the change of the activity of the proline hydroxylase thereof, it was discovered that after these amino acid sites are mutated to any one or more of the following combinations, the activity and/or selectivity of the hydroxylase is further improved. The mutation comprises any one or more of the followings: H14R, S16N, T25G, T25R, F26L, E27K, D30S, S33N, E34N, E34G, E34L, E34S, E34D, Y35W, Y35K, S37W, S37F, S37E, S37N, S37T, S37C, I39K, I39R, W40F, K41E, D54G, H55Q, S57L, I58T, I58Y, I58A, I58R, I58V, I58S, I58C, K86P, T91A, F95Y, C97Y, I98V, K106V, K106T, K106Q, F111S, K112E, K112R, S154A, K162E, L166M, I118F, I118V, I118R, H119R, H119F, I120V, K123D, K123N, K123Q, K123S, K123I, K123T, T130N, D134G, V135K, N165H, D173G, K209R, I223V and S225A. More preferably, the mutation comprises any one or more of the followings: H14R, E27K, E34N, E34G, E34L, E34D, Y35W, Y35K, S37W, S37F, S37E, S37N, S37T, S37C, I39K, I39R, I58T, I58Y, I58A, I58R, I58V, I58S, I58C, K123D, K123N, K123Q, K123S, K123I and K123T. Herein, the amino acid mutations related to the selectivity of the proline hydroxylase are as follows: Y35W, S57L and 557V.

The mutation of some amino acids may improve the soluble expression quantity of the proline hydroxylase in a bacterial cell, especially the soluble expression in an *E. Coli* host cell, these mutated amino acids may be selected from: E27K, D30S, Y35W, Y35K, S37W, S37F, S37E, S37N, S37T, S37C, I39K, I39R, W40F, I58T, I58Y, I58A, I58R, I58V, I58S, I58C, I98V, K106V, K106T, K106Q, H119R, H119F, K123D, K123N, K123Q, K123S, K123I, K123T, N165H, I223V. Generally, when an exogenous gene is expressed in a prokaryotic expression system, only the soluble protein correctly folded is active, a formed inclusion body is inactive. The soluble protein expression quantity is increased, and the total enzyme activity is increased accordingly.

In a more preferable embodiment, the above mutation comprises any one of the following combinations: E27K+Y35W/K, E27K+I39K/R, E27K+K123D/I/Q/S, E27K+N165H, I39K/R+Y35W/K, I39K/R+K123D/I/Q/S, I39K/R+N165H, K123D+W40F, K123D+Y35W/K, E27K+I39K/R+K123D/I/Q/S, K123D/I/Q/S+N165H, S37C/E/F/N/W/T+I223V, E27K+Y35W/K+I39K/R, E27K+S37C/E/F/N/W/T+I39K/R, E27K+E34N/G/L/D/S+I39K/R, E27K+I39K/R+D30S, E27K+I39K/R+I118 F/V/R, E27K+I39K/R+I98V, S37C/E/F/N/W/T+I223V+N165H, Y35W/K+S37C/E/F/N/W/T+W40F, S37C/E/F/N/W/T+I223V+K123D/I/Q/S, E27K+I39K+Y35W/K+S37C/E/F/N/W/T, E27K+I39K/R+S37C/E/F/N/W/T+K123D/I/Q/S, E27K+I39K/R+K106Q+K112E, E27K+I39K/R+Y35W/K+S37C/E/F/N/W/T+K123D/I/Q/S, E27K+I39K/R+S37C/E/F/N/W/T+I58A/C/R/S/T/V/Y, E27K+S37C/E/F/N/W/T+I223V+K123D/I/Q/S, S37C/E/F/N/W/T+I39K/R+I223V+K123D/I/Q/S, E27K+S37C/E/F/N/W/T+I39K/R+K123D/I/Q/S+I98V, E27K+S37C/E/F/N/W/T+I39K/R+K123D/I/Q/S+I223V, F26L+E27K+I39K/R+K123D/I/Q/S, I223V+S37C/E/F/N/W/T+E27K+I39K/R, I223 V+S37C/E/F/N/W/T+E27K+N165H, E27K+S37C/E/F/N/W/T+I39K/R+I98V+K123D/I/Q/S+I223V, K106Q+K112E+I223V, E27K+S37C/E/F/N/W/T+I39K/R+I58A/C/R/S/T/V/Y+K123D/I/Q/S, E27K+I39K/R+K123D/I/Q/S+N165H, H14R+E34G+K106Q+K112E+I223V, T25G/R+E27K+S37C/E/F/N/W/T+I39K/R+I58A/C/R/S/T/V/Y, E27K+S37C/E/F/N/W/T+I39K/R+I58A/C/R/S/T/V/Y+K86P, K123D/I/Q/S+Y35W/K+I120V, E27K+D30S+I39K/R+I58A/C/R/S/T/V/Y+K112E, S37C/E/F/N/W/T+I39K/R+N 165H, E27K+E34N/G/L/D/S+I39K/R+I58A/C/R/S/T/V/Y+1223V, E27K+S37C/E/F/N/W/T+I39K/R+I58A/C/R/S/T/V/Y+D173G, E27K+S37C/E/F/N/W/T+I39K/R+I58A/C/R/S/T/V/Y+D173G+I118F/V/R, E27K+E34N/G/L/D/S+S37C/E/F/N/W/T+I39K/R+I58A/C/R/S/T/V/Y, E27K+E34N/G/L/D/S+S37C/E/F/N/W/T+I39K/R+I58A/C/R/S/T/V/Y+D173G, E27K+S37C/E/F/N/W/T+I39K/R+I58A/C/R/S/T/V/Y+D173G+K123D/I/Q/S, E27K+S37C/E/F/N/W/T+I39K/R+I58A/C/R/S/T/V/Y+D173G+K123D/I/Q/S+I118F/V/R, E27K+S37C/E/F/N/W/T+I39K/R+I58A/C/R/S/T/V/Y+D173G+K123D/I/Q/S+N165H, E27K+E34N/G/L/D/S+S37C/E/F/N/W/T+I39K/R+I58A/C/R/S/T/V/+D173G+K123D/I/Q/S, H14R+E27K+D30S+E34N/G/L/D/S+I39K/R+I98V+K106V/T/Q+K112E/R+I223V, T25G/R+E27K+S37C/E/F/N/W/T+I39K/R+I58A/C/R/S/T/V/Y+D173G+K123D/I/Q/S+I118 F/V/R+N165H, H14R+E27K+E34N/G/L/D/S+I39K/R+I98V+K106V/T/Q+K112E/R+I223V, H14R+E27K+E34N/G/L/D/S+S37C/E/F/N/W/T+I39K/R+I98V+K106V/T/Q+K112E/R+I223V, H14R+E27K+E34N/G/L/D/S+Y35W/K+I39K/R+I98V+K106V/T/Q+K112E/R+I223 V, H14R+E27K+E34N/G/L/D/S+I39K/R+I98V+K106V/T/Q+K112E/R+K123D/I/Q/S+I223V, H14R+E27K+E34N/G/L/D+139K/R+I58A/C/R/S/T/V/Y+198V+K106V/T/Q+K112E/R+I223V and H14R+E27K+E34N/G/L/D/S+I39K/R+I98V+K106V/T/Q+K112E/R+I118F/V/R+I223V. '/' in the above mutation combinations stands for 'or'. In the above mutation combinations, the combinations referring to the mutation of Y35W are related to the selectivity of the proline hydroxylase, and the other combinations are related to the catalytic activity of the proline hydroxylase.

In the above preferable embodiment, catalytic activity information of the proline hydroxylase is screened on the basis of the catalytic activity of the enzyme to L-piperidine acid. Catalytic activity results of the proline hydroxylase in these more preferable embodiments are as shown in Table 1 and Table 2, a sequence number of the DNA sequence is an odd, and a sequence number of the amino acid sequence is an even. The mutated amino acid of the application is obtained by modification based on the amino acid sequence of SEQ ID NO: 2, and the SEQ ID NO: 2 is the sequence of hypothetical protein derived from *Kordia jejudonensis*. The activity of the wild type proline hydroxylase in the application is represented by '1', the activity of the mutant proline hydroxylase is represented by '+': '+' represents that the activity is 1-2 times of wild type SEQ ID NO:2, '++' represents that the activity is 2-3 times of wild type SEQ ID NO:2, '+++' represents that the activity is 3-4 times of wild type SEQ ID NO:2, and '++++' represents that the activity is 4-5 times of wild type SEQ ID NO:2.

TABLE 1

Comparison of proline hydroxylase activity after mutation of a single site.

| No. | SEQ ID NO: (DNA/AA) | Mutated amino acid | activity |
|---|---|---|---|
| 1 | 1/2 | No | 1 |
| 2 | 3/4 | No | 1 |
| 3 | 5/6 | H14R | + |
| 4 | 7/8 | S16N | + |
| 5 | 9/10 | T25G | + |
| 6 | 11/12 | T25R | + |
| 7 | 13/14 | F26L | + |
| 8 | 15/16 | E27K | + |
| 9 | 17/18 | D30S | + |
| 10 | 19/20 | S33N | + |
| 11 | 21/22 | E34N | + |
| 12 | 23/24 | E34G | + |
| 13 | 25/26 | E34L | + |
| 14 | 27/28 | E34D | + |
| 15 | 29/30 | E34S | + |
| 16 | 31/32 | Y35W | ++ |
| 17 | 33/34 | Y35K | ++ |
| 18 | 35/36 | S37W | + |
| 19 | 37/38 | S37F | + |
| 20 | 39/40 | S37E | + |
| 21 | 41/42 | S37N | + |
| 22 | 43/44 | S37T | + |
| 23 | 45/46 | S37C | + |
| 24 | 47/48 | I39K | ++ |
| 25 | 49/50 | I39R | ++ |
| 26 | 51/52 | W40F | + |
| 27 | 53/54 | K41E | + |
| 28 | 55/56 | D54G | + |
| 29 | 57/58 | H55Q | + |
| 30 | 59/60 | S57L | + |
| 31 | 61/62 | I58T | + |
| 32 | 63/64 | I58Y | + |
| 33 | 65/66 | I58A | + |
| 34 | 67/68 | I58R | + |
| 35 | 69/70 | I58V | + |
| 36 | 71/72 | I58S | + |
| 37 | 73/74 | I58C | + |
| 38 | 75/76 | K86P | + |
| 39 | 77/78 | T91A | + |
| 40 | 79/80 | F95Y | + |
| 41 | 81/82 | C97Y | + |
| 42 | 83/84 | I98V | + |
| 43 | 85/86 | K106V | + |
| 44 | 87/88 | K106T | + |
| 45 | 89/90 | K106Q | + |
| 46 | 91/92 | F111S | + |
| 47 | 93/94 | K112E | + |
| 48 | 95/96 | I118F | + |
| 50 | 97/98 | H119R | ++ |
| 51 | 99/100 | H119F | + |
| 52 | 101/102 | I120V | + |
| 53 | 103/104 | K123D | ++ |
| 54 | 105/106 | K123N | + |
| 55 | 107/108 | K123Q | + |
| 56 | 109/110 | K123S | + |
| 57 | 111/112 | K123I | + |
| 58 | 113/114 | K123T | + |
| 59 | 115/116 | T130N | + |

TABLE 1-continued

Comparison of proline hydroxylase activity after mutation of a single site.

| No. | SEQ ID NO: (DNA/AA) | Mutated amino acid | activity |
|---|---|---|---|
| 60 | 117/118 | D134G | + |
| 61 | 119/120 | V135K | + |
| 62 | 121/122 | N165H | + |
| 63 | 123/124 | K209R | + |
| 64 | 125/126 | I223V | + |

The Table 1 provides the effects on the catalytic activity of the mutated proline hydroxylase by performing the modification of the amino acids at different sites on the basis of the sequence of SEQ ID NO:2. Herein, the mutated proline hydroxylase was expressed from an *E. coli* BL21 cell, the catalytic activity was based on conversion efficiency of the enzyme to L-piperidine acid. The above catalytic reaction was performed in a 10 ml reaction system, and the reaction system comprises: 30 g/L L-piperidine acid, 5-10 wt recombinase (1 wt is an 1 g proline hydroxylase variant recombined wet cell needed for converting an 1 g main raw material), 37.3 g/L α-ketoglutarate, 6.1 g/L L-ascorbic acid, 5 mM ammonium ferrous sulfate, the reaction pH was 6.5, the reaction temperature was 10 DEG C., and the reaction time was 40 hours.

TABLE 2

Comparison of proline hydroxylase activity after multi-site mutation.

| No. | SEQ ID NO: (DNA/AA) | Mutated amino acid | Activity |
|---|---|---|---|
| 1 | 127/128 | E27K + K123D | ++ |
| 2 | 129/130 | E27K + I39K | +++ |
| 3 | 131/132 | I39K + K123Q | ++ |
| 4 | 133/134 | I39K + K123D | ++ |
| 5 | 135/136 | S37C + I223V + K123D | ++ |
| 6 | 137/138 | K123D + N165H | ++ |
| 7 | 139/140 | I39R + K123D | +++ |
| 8 | 141/142 | E27K + I39K + K123D | +++ |
| 9 | 143/144 | E27K + I39R | +++ |
| 10 | 145/146 | I39R + N165H | + |
| 11 | 147/148 | I39K + N165H | + |
| 12 | 149/150 | E27K + I39R + K123D | +++ |
| 13 | 151/152 | S37C + I223V + N165H | + |
| 14 | 153/154 | K123D + W40F | ++ |
| 15 | 155/156 | E27K + N165H | ++ |
| 16 | 157/158 | E27K + S37C + I223V + K123D | +++ |
| 17 | 159/160 | S37C + I39K + I223V + K123D | ++++ |
| 18 | 161/162 | E27K + S37C + I39K +K123D + I98V | ++++ |
| 19 | 163/164 | E27K + S37C + I39K + K123D + I223V | ++ |
| 20 | 165/166 | F26L + E27K + I39K + K123D | ++ |
| 21 | 167/168 | I223V + S37C + E27K + I39K | +++ |
| 22 | 169/170 | I223V + S37C + E27K + N165H | +++ |
| 23 | 171/172 | K123D + Y35W | ++ |
| 24 | 173/174 | K123D + Y35W + I120V | ++ |
| 25 | 175/176 | E27K + Y35W | ++ |
| 26 | 177/178 | I39R + Y35W | ++++ |
| 27 | 179/180 | S37C + I223V | ++ |
| 28 | 181/182 | E27K + I39K + Y35W | ++++ |
| 29 | 183/184 | E27K + S37C + I39K + I98V + K123D + I223V | ++ |
| 30 | 185/186 | E27K + I39K + K123D + N165H | + |
| 31 | 187/188 | E27K + I39R + Y35W | +++ |
| 32 | 189/190 | S37C + I39K + N165H | ++ |
| 33 | 191/192 | E27K + I39K + D30S | +++ |
| 34 | 193/194 | E27K + I39K + E34N | +++ |
| 35 | 195/196 | E27K + I39K + E34G | +++ |
| 36 | 197/198 | E27K + I39K + S37W | +++ |
| 37 | 199/200 | E27K + I39K + S37E | +++ |
| 38 | 201/202 | E27K + I39K + Y35K | +++ |

TABLE 2-continued

Comparison of proline hydroxylase activity after multi-site mutation.

| No. | SEQ ID NO: (DNA/AA) | Mutated amino acid | Activity |
|---|---|---|---|
| 39 | 203/204 | E27K + I39K + S37N | +++ |
| 40 | 205/206 | E27K + I39K + K123Q | +++ |
| 41 | 207/208 | E27K + I39K + K123S | +++ |
| 42 | 209/210 | E27K + I39K + K106Q + K112E | +++ |
| 43 | 211/212 | I98V + E27K + I39K | +++ |
| 44 | 213/214 | E27K + I39K + I118F | +++ |
| 45 | 215/216 | E27K + I39K + S37T | +++ |
| 46 | 217/218 | E27K + I39K + K123I | +++ |
| 47 | 219/220 | K106Q + K112E + I223V | +++ |
| 48 | 221/222 | H14R + E34G + K106Q + K112E + I223V | +++ |
| 49 | 223/224 | E27K + I39K + E34L | +++ |
| 50 | 225/226 | E27K + I39K + S37F + I58T | +++ |
| 51 | 227/228 | E27K + I39K + S37F + I58Y | +++ |
| 52 | 229/230 | E27K + I39K + S37F + I58A | +++ |
| 53 | 231/232 | E27K + I39K + S37F + I58R | +++ |
| 54 | 233/234 | E27K + I39K + S37F + I58V | +++ |
| 55 | 235/236 | E27K + I39K + S37F + I58S | +++ |
| 56 | 237/238 | E27K + I39K + S37N + I58C | +++ |
| 57 | 239/240 | E27K + D30S + I39K + I58R + K112E | ++++ |
| 58 | 241/242 | E27K + E34N + I39K + I58Y + I223V | ++++ |
| 59 | 243/244 | E27K + S37N + I39K + I58Y + D173G | +++ |
| 60 | 245/246 | E27K + S37F + I39K + I58Y + D173G | +++ |
| 61 | 247/248 | E27K + I39K + S37N + I58A | +++ |
| 62 | 249/250 | E27K + I39K + S37N + I58R + K123Q | +++ |
| 63 | 251/252 | E27K + S37F + I39K + I58Y + D173G + I118R | +++ |
| 64 | 253/254 | E27K + E34L + S37N + I39K + I58R | +++ |
| 65 | 255/256 | E27K + E34L + S37N + I39K + I58Y + D173G | +++ |
| 66 | 257/258 | E27K + E34L + S37N + I39K + I58Y + D173G + K123Q | +++ |
| 67 | 259/260 | H14R + E27K + D30S + E34G + I39K + I98V + K106Q + K112E + I223V | +++ |
| 68 | 261/262 | H14R + E27K + E34N + I39K + I98V + K106Q + K112E + I223V | +++ |
| 69 | 263/264 | H14R + E27K + E34G + I39K + I98V + K106Q + K112E + I223V | +++ |
| 70 | 265/266 | H14R + E27K + E34G + S37W + I39K + I98V + K106Q + K112E + I223V | +++ |
| 71 | 267/268 | H14R + E27K + E34G + S37F + I39K + I98V + K106Q + K112E + I223V | +++ |
| 72 | 269/270 | H14R + E27K + E34G + S37E + I39K + I98V + K106Q + K112E + I223V | +++ |
| 73 | 271/272 | H14R + E27K + E34G + Y35K + I39K + I98V + K106Q + K112E + I223V | ++++ |
| 74 | 273/274 | H14R + E27K + E34G + S37N + I39K + I98V + K106Q + K112E + I223V | +++ |
| 75 | 275/276 | H14R + E27K + E34G + I39K + I98V + K106Q + K112E + K123Q + I223V | ++++ |
| 76 | 277/278 | H14R + E27K + E34G + I39K + I98V + K106Q + K112E + K123S + I223V | +++ |
| 77 | 279/280 | H14R + E27K + E34G + I39K + I58A + I98V + K106Q + K112E + I223V | +++ |
| 78 | 281/282 | H14R + E27K + E34G + I39K + I98V + K106Q + K112E + I118F + I223V | +++ |
| 79 | 283/284 | H14R + E27K + E34G + S37T + I39K + I98V + K106Q + K112E + I223V | +++ |
| 80 | 285/286 | H14R + E27K + E34G + I39K + I58V + I98V + K106Q + K112E + I223V | +++ |
| 81 | 287/288 | H14R + E27K + E34G + I39K + I98V + K106Q + K112E + K123I + I223V | +++ |

The Table 2 provides the effects on the catalytic activity of the proline hydroxylase through the modification of amino acids at multiple sites. The proline hydroxylase was expressed from the *E. coli* BL21 cell, the catalytic activity was based on the conversion efficiency of the enzyme to the L-piperidine acid. The catalytic process was performed in a 20 ml reaction system, herein the reaction system comprises 50 g/L L-piperidine acid, 2-5 wt recombinase, 62.2 g/L α-ketoglutarate, 10.2 g/L L-ascorbic acid, 5 mM ammonium ferrous sulfate, the reaction pH was 6.5, the reaction temperature was 10 DEG C., and the reaction time was 40 hours.

In some embodiments, one or more amino acid residues related to the proline hydroxylase activity is selected as a core and kept unchanged, and new mutation is introduced in other amino acid residue positions, the proline hydroxylase with the improved property may be generated. So, any one proline hydroxylase in the above preferable embodiments may be used as a female parent amino acid sequence for synthesizing other proline hydroxylase mutants by genetic engineering. For example new mutants of which the amino acid residues obtained by several rounds of evolution are different from the amino acid sequences in the Table 1 and Table 2.

Any one of the above disclosed proline hydroxylases, or any new mutant having the proline hydroxylase activity obtained by performing the mutation of one or more amino acid residues in the other amino acid residue positions on the basis of the above disclosed proline hydroxylases or the variants thereof are within the scope of protection of the application. It may be illustrated, but not limited to this, the proline hydroxylase mutant containing the mutation of the E27 amino acid residue may further be performed the mutation of one or more other amino acids, for example: H14, S16, T25, F26, D30, S33, E34, Y35, S37, I39, W40, K41, D54, H55, S57, I58, K86, T91, F95, C97, I98, K106, F111, K112, K162, L166, I118, H119, 1120, K123, T130, D134, V135, S154, N165, D173, K209, I223, S225. Another example is that the proline hydroxylase mutant containing the mutation of the 139 amino acid residue may further be performed the mutation of one or more other amino acids, for example: H14, S16, T25, F26, E27, D30, S33, E34, Y35, S37, W40, K41, D54, H55, S57, 158, K86, T91, F95, $C_{97}$, I98, K106, F111, K112, K162, L166, I118, H119, I120, K123, T130, D134, V135, S154, N165, D173, K209, I223, S225. Another example is that the proline hydroxylase mutant containing the mutation of the 158 amino acid residue may further be performed the mutation of one or more other amino acids, for example: H14, S16, T25, F26, E27, D30, S33, E34, Y35, S37, I39, W40, K41, D54, H55, S57, I58, K86, T91, F95, C97, I98, K106, F111, K112, K162, L166, I118, H119, I120, K123, T130, D134, V135, S154, N165, D173, K209, I223, S225.

The above hydroxylases have the proline hydroxylase activity, and are capable of catalyzing (2S)-piperidine-2-carboxylic acid to be converted to (2S,5S)-5-hydroxypiperidine-2-carboxylic acid, and improving the catalytic activity of the enzyme through genetic engineering, the hydroxylase activity of the mutants in some embodiments is improved by 1 time, 2 times, 3 times, 4 times, 5 times or more compared with the activity of the hydroxylase encoded by SEQ ID NO: 2 itself.

In another typical implementation mode of the application, a DNA molecule is provided, wherein the DNA molecule encodes any one of the above hydroxylases. The encoded hydroxylases have the advantages of high specificity and remarkably improved catalytic activity.

In another typical implementation mode of the application, a recombinant vector is further provided, wherein the recombinant vector is connected with the DNA molecule. The DNA molecule may encode any one of the above proline hydroxylases with high selectivity, and/or remarkably improved catalytic activity. The specific sequence is selected from the sequence in Table 1 and Table 2 of which the number is an odd, or a nucleotide sequence which is generated by substitution, addition or deletion mutation within the amino acid sequences in the other sites in the precondition of keeping the changed amino acid sites of these sequences.

In the above recombinant vector, any recombinant vector which may be used for expressing the DNA molecule of the above hydroxylase are suitable for the application. In the preferable embodiment of the application, the recombinant vector is selected from one of the followings: pET-22b(+), pET-21b(+), pET-3a(+), pET-3d(+), pET-11a(+), pET-12a (+), pET-14b(+), pET-15b(+), pET-16b(+), pET-17b(+), pET-19b(+), pET-20b(+), pET-21a(+), pET-23a(+), pET-23b (+), pET-24a(+), pET-25b(+), pET-26b(+), pET-27b(+), pET-28a(+), pET-29a(+), pET-30a(+), pET-31b(+), pET-32a (+), pET-35b(+), pET-38b(+), pET-39b(+), pET-40b(+), pET-41a(+), pET-41b(+), pET-42a(+), pET-43a(+), pET-43b (+), pET-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwinl, pEZZ18, pKK232-18, pUC-18 and PUG 19.

In another typical implementation mode of the application, a host cell is provided, wherein the host cell comprises any one of the recombinant vectors. The specific host cell may be a prokaryotic cell or a eukaryocyte, preferably the eukaryocyte is a yeast cell. More preferably, the host cell is a competent cell, further preferably the competent cell is an *E. coli* BL21 cell or an *E. coli* W3110 cell.

In another typical implementation mode of the application, a method for producing an L-hydroxyproline derivative is further provided, wherein the method comprises the following steps: using an L-proline derivative as a substrate, and applying the proline hydroxylases as claimed in any one of claims 1 to 4 to catalyze hydroxylation of the substrate, to obtain the L-hydroxyproline derivative as shown in a general formula (I):

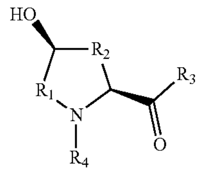

(I)

Wherein $R_1$ is selected from $C_1$-$C_5$ alkylene or $C_2$-$C_5$ alkenylene; $R_2$ is selected form $C_0$-$C_4$ alkylene or $C_2$-$C_4$ alkenylene; R3 is selected from hydroxyl, amino, $C_1$-$C_6$ alkoxy, aryloxy, $C_1$-$C_6$ alkyl sulfenyl or $C_1$-$C_6$ aryl sulfenyl; and R4 is selected from hydrogen, $C_1$-$C_6$ alkyl, $C_2$-$C_6$ alkenyl or $C_2$-$C_6$ alkynyl.

The above proline hydroxylase of the application is used for catalyzing the L-proline derivative to be a hydroxide thereof, not only catalytic efficiency may be improved, and the conversion rate of the L-proline derivative is improved, but also specificity of the catalysis is improved, so a purity of an obtained target product of the L-hydroxyproline derivative is improved, and the follow-up separating process is reduced.

Figure 2:
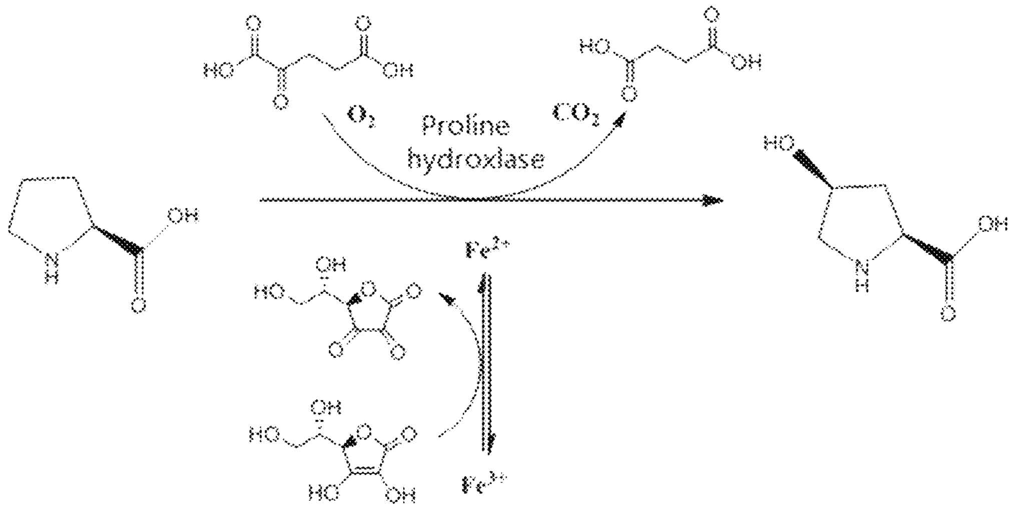
FIG. 2 shows an equation of a chemical reaction of a use of a proline hydroxylase according to the present application in catalytic-synthesizing cis-4-hydroxy-L-proline.

The chemical reaction equation for catalytic-synthesizing the L-hydroxyproline derivative with the proline hydroxylase is shown in FIG. 2. Herein,

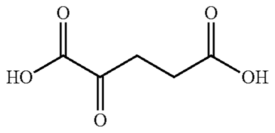

is α-ketoglutarate, in the catalytic reaction of the proline hydroxylase, the α-ketoglutarate and $O_2$ are used as a common substrate. Under the combined action of iron ions as a cofactor, the hydroxylation of the substrate is catalyzed, to obtain the L-hydroxyproline derivative;

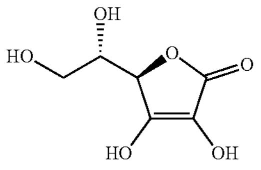 [SMILES: O=C1O[C@H]([C@@H](O)CO)C(O)=C1O]

is vitamin C, named as ascorbic acid too, in the catalytic reaction of the proline hydroxylase, which mainly plays the role of circulating the iron ions.

As a typical dioxygenase, just like the proline hydroxylase in prior art, in the catalytic reaction of the proline hydroxylase, α-ketoglutarate and the $O_2$ are needed, and the iron ions are needed as the cofactor. So the method comprises: the α-ketoglutarate and the $O_2$ are used as the common substrate, the iron ions are used as the cofactor, the hydroxylation of the substrate is catalyzed by the proline hydroxylase, so the L-hydroxyproline derivative is obtained.

The specific reaction conditions may be appropriately adjusted on the basis of the proline hydroxylase reaction system in prior art. For example, a concentration of a reducing agent (for example, the ascorbic acid), a concentration of a detergent, pH value, temperature, buffering, a solvent system, substrate loading, polypeptide loading, a pressure and reaction time and the like may be appropriately adjusted. In some embodiments, the specific reaction conditions are as follows: 15~120 g/L of the substrate, 1.5~48 g/L of the hydroxylase, 1~2.5 eq (eq: represents a proportion value of a mass of a used material and a mass of a main raw material) of the α-ketoglutarate, 0.1~0.3 eq of L-ascorbic acid, 1~10 mM of the ammonium ferrous sulfate, 6~8 of the reaction pH, 5~30 DEG C. of the reaction temperature, and 6~96 hours of the reaction time. In some embodiments, the appropriate reaction condition comprises that 2~5 Uh of oxygen and 0.5~2% of a defoaming agent are fed into the reaction solution.

In a preferably embodiment of the application, the proline hydroxylase may catalyze the hydroxylation of the substrate at 5~45 DEG C. of the reaction temperature, and the L-hydroxyproline derivative as shown in the general formula I is obtained. More preferably, the catalytic reaction is performed at 5~15 DEG C. of the reaction temperature. The improved proline hydroxylase of the application may not only catalyze the substrate to the hydroxide thereof in the lower temperature, but also improve the catalytic specificity (namely the selectivity), and the purity of the product is improved.

The enzyme may perform hydroxylation on multiple types of the L-proline derivatives. In a preferable embodiment of the application, the hydroxylation is performed on the L-proline or L-piperidine acid, cis-4-hydroxy-L-proline or (2S,5S)-5-hydroxypiperidine-2-carboxylic acid is obtained. The specificity of the hydroxylation to the above two substrates is the highest, and 100% of the substrate may be converted to the cis-4-hydroxy-L-proline or the (2S,5S)-5-hydroxypiperidine-2-carboxylic acid.

The beneficial effects of the application are further described below in combination with the specific embodiments. Experimental methods below are conventional methods if not specifically indicated, and used experimental materials may easily be acquired from a commercial corporation if not specifically indicated.

Embodiment 1: Recombination Expression of Proline Hydroxylase

Codon optimization (codon improvement was performed according to codon bias and degeneracy for *E. coli*, which was designed and completed by GENEWIZ SuZhou Co., Ltd) was performed on a DNA coding sequence SEQ ID NO: 1 annotated as a hypothetical protein and derived from *Kordia jejudonensis*, and the optimized DNA sequence SEQ ID NO: 3 was obtained, and the encoded proline hydroxylase polypeptide sequence is SEQ ID NO: 4. The coding sequence of SEQ ID NO: 3 was connected to a pET22b(+) expression vector (purchased from Novagen, and the product number is 69744), and transformed into *E. coli* BL21 (DE3), coated in an LB culture dish containing ampicillin having a final concentration of 50 μg/ml, and cultured overnight at 37 DEG C. A single colony on the culture dish was selected and inoculated in 500 ml of an LB liquid culture medium containing ampicillin having a final concentration of 50 μg/ml, then cultured by shaking at 37 DEG C. until $OD_{600}$=0.6, IPTG was added until the final concentration being 1 mM, and induced to express at 25 DEG C. After induction for 16 hours, the thalli were collected by centrifugation at 6000 g for 10 min. The thalli were disrupted by an ultrasonic cell disruptor (JY92-2D, Ningbo Xin Zhisheng science and technology Co., Ltd), and the supernatant was obtained by centrifugation at 10000 g for 20 min at 4 DEG C. for detection of wild-type proline hydroxylase activity as a control for screening the mutant activity.

Embodiment 2: Preparation of Proline Hydroxylase Mutants

A pET22b (+) expression vector containing the sequence of SEQ ID NO: 3 was used as a template, and a primer with a mutation site was used for acquiring a complete linear fragment through a full-length plasmid PCR, and the PCR product was digested by DPn I to remove the female parent template, and then transformed into *E. coli* BL21(DE3), coated in an LB culture dish containing ampicillin having a final concentration of 50 μg/ml and incubated overnight at 37 DEG C., and a monoclone containing an amino acid sequence of the proline hydroxylase mutant was obtained, and the mutation site was determined through induction testing and gene sequencing. Finally mutants with single mutation sites were obtained, and the mutants with the single mutation sites were used as a mutated female parent, and the primers with a mutation in other sites were used for performing the full-length plasmid PCR again, and then mutation sites were detected again.

After activated, the mutant bacteria was inoculated into 500 ml of LB fluid culture medium containing ampicillin having a final concentration of 50 μg/ml, and subjected to shake culture at 37 DEG C. until $OD_{600}$=0.6, then IPTG was added to a final concentration of 1 mM, and induction expression was carried out at 25 DEG C. After induction for 16 hours, the cells were collected by centrifugation at 6000 g for 10 min. The thalli were disrupted by an ultrasonic cell disruptor (JY92-2D, Ningbo Xin Zhisheng science and technology Co., Ltd), and the supernatant was obtained by centrifugation at 10000 g for 20 min at 4 DEG C. for activity detection of proline hydroxylase variants.

Embodiment 3: Activity Screening of Proline Hydroxylase Variants

The activity screening of the proline hydroxylase variants in which one amino acid residue differs from SEQ ID NO: 2 was screened using the following 10 mL of the reaction solution, and the 10 mL of the reaction solution comprises: 30 g/L of L-piperidine acid, 5-10 wt of recombinant crude enzyme (1 wt is 1 g proline hydroxylase variant recombinant wet cell needed for converting an 1 g main raw material), 37.3 g/L of α-ketoglutarate, 6.1 g/L of L-ascorbic acid, 5 mM of ammonium ferrous sulfate, the reaction pH was 6.5, the reaction temperature was 10 DEG C., and the reaction time was 40 hours. At the end of the reaction, 200 μL of the reaction system was taken, and then 200 μL of acetonitrile was added thereof, and 3000 μL of purified water was added after uniformly mixing, and the supernatant was collected by centrifugation at 10000 rpm for 5 min for HPLC to determine the conversion rate. The activity screening results were shown in Table 1 (Table 1 shows the activity screening results obtained according to the comparison of all conversion rate data).

The activity screening of the proline hydroxylase variants in which multiple amino acid residues differ from SEQ ID NO: 2 was screened using the following 20 mL of reaction solution, and the 20 mL of the reaction solution comprises: 50 g/L of L-piperidine acid, 2-5 wt of recombinant crude enzyme, 62.2 g/L of α-ketoglutarate, 10.2 g/L of L-ascorbic acid, 5 mM of ammonium ferrous sulfate, the reaction pH was 6.5, the reaction temperature was 10 DEG C., and the reaction time was 40 hours. At the end of the reaction, 100 μL of the reaction system was taken, then 200 μL of acetonitrile was added thereof, and 3000 μL of purified water was added after uniformly mixing, and the supernatant was collected by centrifugation at 10000 rpm for 5 min for HPLC to determine the conversion rate, and the activity screening results were shown in Table 2 (Table 2 shows the activity screening results obtained according to the comparison of all conversion rate data).

Embodiment 4: Clone and Expression of Proline Hydroxylase Mutants

In order to conveniently express and identify the hydroxylase mutants, a compatible restriction site was designed at 5' and 3' terminals of the gene thereof. Nde I and Xho I may be used for simultaneously performing digestion on the target gene and pET-22b(+) (other expression plasmids which may express the protein in *E. coli* may be also used), the target gene after the digestion and a larger fragment of the plasmid were performed a ligation reaction with a T4 DNA ligase, and a ligation product was converted into competent cells of *E. coli* DH5α strains, and the converted competent cells were coated on an LB culture plate containing ampicillin with a final concentration of 50 μg/ml, and cultured overnight at 37 DEG C.

A single colony grown on the above culture dish was selected, and inoculated in an LB fluid culture medium containing ampicillin having a final concentration of 50 μg/ml, and subjected to shake culture at 37 DEG C. overnight, bacteria liquid was collected, and after plasmid extraction, PCR identification and double digestion identification were performed, a correct clone vector was named as pET22b (+)-R-M and transformed into *E. coli* BL21 (DE3). The transformed *E. coli* BL21(DE3) was coated on the LB culture plate containing ampicillin having a final concentration of 50 μg/ml, and cultured at 37 DEG C. overnight. The single colony grown on the above culture plate was selected, and inoculated in 5 ml of the LB fluid culture medium containing ampicillin having a final concentration of 50 μg/ml, and the colony PCR was used for identification, and the *E. coli* cells containing the correct expression vector were performed the follow-up induction expression. The above bacteria solution is transferred and inoculated in 500 ml of the LB fluid culture medium containing ampicillin having a final concentration of 50 μg/ml, then cultured by shaking at 37 DEG C. until $OD_{600}$=0.5-0.6, IPTG was added until the final concentration being 0.2-1.0 mM, after the induced expression was performed at 18-25 DEG C. for 10-16 hours, the bacteria liquid was taken out, and the thalli were collected and centrifuged at 6000 g for 10 min, and frozen-stored for future use in −20 DEG C. The thalli were broken by an ultrasonic cell disruptor (JY92-2D, Ningbo Xin Zhisheng science and technology Co., Ltd), and the supernatant and precipitate were obtained at 4 DEG C. by centrifugation at 10000 g for 20 min, and the supernatant were detected by SDS-PAGE with a vertical electrophoresis apparatus. The molecular weight of the expressed hydroxylase mutant displayed on SDS-PAGE was about 30 KD.

Embodiment 5: Performance Comparison of Hydroxylases in Table 1 and Table 2 and Wild Type Proline Hydroxylase The following experiments were performed according to the chemical reaction process as shown in FIG. 1 for hydroxylase-catalyzed synthesis of (2S,5S)-5-hydroxypiperidine-2-carboxylic acid (or named as cis-5-hydroxypiperidine acid):

20 ml of the following reaction solution was used in a process that the wild type proline hydroxylase encoded by SEQ ID NO:2 catalyzed L-piperidine acid to prepare the (2S,5S)-5-hydroxypiperidine-2-carboxylic acid. 20 mL of the reaction solution comprised: 50 g/L of L-piperidine acid, 10 wt of hydroxylase, 62.2 g/L of α-ketoglutarate, 10.2 g/L of L-ascorbic acid, 5 mM of ammonium ferrous sulfate, the reaction pH was 6.5, the reaction temperature was 10 DEG C., and the reaction time was 40 hours. At the end of the reaction, 100 μL of the reaction system was taken, and then 200 μL of acetonitrile was added thereof, and 3000 μL of purified water was added after uniformly mixing, and the supernatant was collected by centrifugation at 10000 rpm for 5 min for HPLC to determine the conversion rate. At 40 hours, a conversion rate was 98.47%, and diastereomeric excess of the (2S,5S)-5-hydroxypiperidine-2-carboxylic acid was 98.36%.

20 ml of the following reaction solution was used in a process that the proline hydroxylase mutant with E27K amino acid residue mutation encoded by SEQ ID NO: 16 catalyzed L-piperidine acid to prepare the (2S,5S)-5-hydroxypiperidine-2-carboxylic acid. 20 mL of the reaction solution comprised: 50 g/L of L-piperidine acid, 10 wt/8 wt of recombinase, 62.2 g/L of α-ketoglutarate, 10.2 g/L of L-ascorbic acid, 5 mM of ammonium ferrous sulfate, the reaction pH was 6.5, the reaction temperature was 10 DEG C., and the reaction time was 40 hours. At the end of the reaction, 100 μL of the reaction system was taken, and then 200 μL of acetonitrile was added thereof, and 3000 μL of purified water was added after uniformly mixing, and the supernatant was collected by centrifugation at 10000 rpm for 5 min for HPLC to determine the conversion rate. At 40 hours, a conversion rate was 94.53%, and diastereomeric excess of the (2S,5S)-5-hydroxypiperidine-2-carboxylic acid was 98.32%.

20 ml of the following reaction solution was used in a process that the proline hydroxylase mutant with N165H amino acid residue mutation encoded by SEQ ID NO: 122 catalyzed L-piperidine acid to prepare the (2S,5S)-5-hydroxypiperidine-2-carboxylic acid. 20 mL of the reaction solution comprised: 50 g/L of L-piperidine acid, 10 wt and 6.67 wt of recombinase, 62.2 g/L of α-ketoglutarate, 10.2 g/L of L-ascorbic acid, 5 mM of ammonium ferrous sulfate, the reaction pH was 6.5, the reaction temperature was 10 DEG C., and the reaction time was 40 hours. At the end of the reaction, 100 μL of the reaction system was taken, and then 200 μL of acetonitrile was added thereof, and 3000 μL of purified water was added after uniformly mixing, and the supernatant was collected by centrifugation at 10000 rpm for 5 min for HPLC to determine the conversion rate. In the reaction system of which the amount of recombinase was 10 wt and 6.67 wt respectively, after 40 hours, the conversion rate was 100% and 90.41% respectively, and diastereomeric excess of the (2S,5S)-5-hydroxypiperidine-2-carboxylic acid was 99.89%.

According to another more preferable single-site mutant, 20 ml of the following reaction solution was used in a process that the proline hydroxylase mutant with K123D amino acid residue mutation encoded by SEQ ID NO: 104 catalyzed L-piperidine acid to prepare the (2S,5S)-5-hydroxypiperidine-2-carboxylic acid. 20 mL of the reaction solution comprised: 50 g/L of L-piperidine acid, 8 wt/5 wt/4 wt of recombinase, 62.2 g/L of α-ketoglutarate, 10.2 g/L of L-ascorbic acid, 5 mM of ammonium ferrous sulfate, the reaction pH was 6.5, the reaction temperature was 10 DEG C., and the reaction time was 40 hours. At the end of the reaction, 100 μL of the reaction system was taken, and then 200 μL of acetonitrile was added thereof, and 3000 μL of purified water was added after uniformly mixing, and the supernatant was collected by centrifugation at 10000 rpm for 5 min for HPLC to determine the conversion rate. In the reaction system of which the amount of recombinase was 8 wt, 5 wt and 4 wt respectively, after 40 hours, the conversion rate was 100%, 97.83% and 89.09% respectively, and diastereomeric excess of the (2S,5S)-5-hydroxypiperidine-2-carboxylic acid was 98.68%.

According to a multi-site mutant, 20 ml of the following reaction solution was used in a process that the proline hydroxylase mutant with S37C+I223V amino acid residue mutation encoded by SEQ ID NO: 180 catalyzed L-piperidine acid to prepare the (2S,5S)-5-hydroxypiperidine-2-carboxylic acid. 20 mL of the reaction solution comprised: 50 g/L of L-piperidine acid, 8 wt/5 wt of recombinase, 62.2 g/L of α-ketoglutarate, 10.2 g/L of L-ascorbic acid, 5 mM of ammonium ferrous sulfate, the reaction pH was 6.5, the reaction temperature was 10 DEG C., and the reaction time was 40 hours. At the end of the reaction, 100 μL of the reaction system was taken, and then 200 μL of acetonitrile was added thereof, and 3000 μL of purified water was added after uniformly mixing, and the supernatant was collected by centrifugation at 10000 rpm for 5 min for HPLC to determine the conversion rate. In the reaction system of which the amount of recombinase was 8 wt and 5 wt respectively, after 40 h, the conversion rate was 100% and 93.99% respectively, and diastereomeric excess of the (2S,5S)-5-hydroxypiperidine-2-carboxylic acid was 98.25%.

According to the multi-site mutant, 20 ml of the following reaction solution was used in a process that the proline hydroxylase mutant with I39R+Y35W amino acid residue mutation encoded by SEQ ID NO: 178 catalyzed L-piperidine acid to prepare the (2S,5S)-5-hydroxypiperidine-2-carboxylic acid. 20 mL of the reaction solution comprised: 50 g/L of L-piperidine acid, 5 wt/3 wt of recombinase, 62.2 g/L of α-ketoglutarate, 10.2 g/L of L-ascorbic acid, 5 mM of ammonium ferrous sulfate, the reaction pH was 6.5, the reaction temperature was 10 DEG C., and the reaction time was 40 hours. At the end of the reaction, 100 μL of the reaction system was taken, and then 200 μL of acetonitrile was added thereof, and 3000 μL of purified water was added after uniformly mixing, and the supernatant was collected by centrifugation at 10000 rpm for 5 min for HPLC to determine the conversion rate. In the reaction system of which the amount of recombinase was 5 wt and 3 wt respectively, after 40 h, the conversion rate was 100% and 94.45% respectively, and diastereomeric excess of the (2S,5S)-5-hydroxypiperidine-2-carboxylic acid was 75.02%. Although the selectivity of the mutant is poorer, the catalytic activity thereof is apparently higher than that of the wild type proline hydroxylase.

According to a more preferable combined mutant, 20 ml of the following reaction solution was used in a process that the proline hydroxylase mutant with I39R+K123D amino acid residue mutation encoded by SEQ ID NO: 140 catalyzed L-piperidine acid to prepare the (2S,5S)-5-hydroxypiperidine-2-carboxylic acid. 20 mL of the reaction solution comprised: 50 g/L of L-piperidine acid, 4 wt/3 wt of recombinase, 62.2 g/L of α-ketoglutarate, 10.2 g/L of L-ascorbic acid, 5 mM of ammonium ferrous sulfate, he reaction pH was 6.5, the reaction temperature was 10 DEG C., and the reaction time was 40 hours. At the end of the reaction, 100 μL of the reaction system was taken, and then 200 μL of acetonitrile was added thereof, and 3000 μL of purified water was added after uniformly mixing, and the supernatant was collected by centrifugation at 10000 rpm for 5 min for HPLC to determine the conversion rate. In the reaction system of which the amount of recombinase was 4 wt and 3 wt respectively, after 40 h, the conversion rate was 97.35% and 92.08% respectively, and diastereomeric excess of the (2S,5S)-5-hydroxypiperidine-2-carboxylic acid was 99.26%.

According to another more preferable combined mutant, 20 ml of the following reaction solution was used in a process that the proline hydroxylase mutant with S37C+139K+I223V+K123D amino acid residue mutation encoded by SEQ ID NO: 160 catalyzed L-piperidine acid to prepare the (2S,5S)-5-hydroxypiperidine-2-carboxylic acid. 20 mL of the reaction solution comprised: 50 g/L of L-piperidine acid, 3 wt/2 wt of recombinase, 62.2 g/L of α-ketoglutarate, 10.2 g/L of L-ascorbic acid, 5 mM of ammonium ferrous sulfate, the reaction pH was 6.5, the reaction temperature was 10 DEG C., and the reaction time was 40 hours. At the end of the reaction, 100 μL of the reaction system was taken, and then 200 μL of acetonitrile was added thereof, and 3000 μL of purified water was added after uniformly mixing, and the supernatant was collected by centrifugation at 10000 rpm for 5 min for HPLC to determine the conversion rate. In the reaction system of which the amount of recombinase was 3 wt and 2 wt respectively, after 40 h, the conversion rate was 95.23% and 88.41% respectively, and diastereomeric excess of the (2S,5S)-5-hydroxypiperidine-2-carboxylic acid was 99.90%.

Embodiment 6

An amino acid sequence PH1 (as shown in SEQ ID No: 289 in the sequence listing) independently designed and constructed by the inventor has 78% of homology with SEQ ID NO:2. The protein was used for catalyzing the L-piperidine acid to prepare (2S,5S)-5-hydroxypiperidine-2-carboxylic acid. 20 ml of the following reaction solution was used. 20 mL of the reaction solution comprised: 50 g/L of L-piperidine acid, 9 wt of recombinase, 62.2 g/L of α-ketoglutarate, 10.2 g/L of L-ascorbic acid, 5 mM of ammonium ferrous sulfate, the reaction pH was 6.5, the reaction temperature was 10 DEG C., and the reaction time was 40 hours. At the end of the reaction, 100 μL of the reaction system was taken, and then 200 μL of acetonitrile was added thereof, and 3000 μL of purified water was added after uniformly mixing, and the supernatant was collected by centrifugation at 10000 rpm for 5 min for HPLC to determine the conversion rate. After 40 h, a conversion rate was 98.56% respectively, and diastereomeric excess of the (2S,5S)-5-hydroxypiperidine-2-carboxylic acid was 98.45%.

Embodiment 7

1) A I39K+S33N amino acid residues mutation in SEQ ID NO:2 has 99% of homology with SEQ ID NO:2, and the amino acid sequence thereof is shown in SEQ ID NO: 290 in a sequence listing. Mutated enzyme encoded by the sequence was used for catalyzing the L-piperidine acid to prepare (2S,5S)-5-hydroxypiperidine-2-carboxylic acid. 20 ml of the following reaction solution was used. 20 mL of the reaction solution comprised: 50 g/L of L-piperidine acid, 8 wt/6 wt of recombinase, 62.2 g/L of α-ketoglutarate, 10.2 g/L of L-ascorbic acid, 5 mM of ammonium ferrous sulfate, the reaction pH was 6.5, the reaction temperature was 10 DEG C., and the reaction time was 40 hours. At the end of the reaction, 100 μL of the reaction system was taken, and then 200 μL of acetonitrile was added thereof, and 3000 μL of purified water was added after uniformly mixing, and the supernatant was collected by centrifugation at 10000 rpm for 5 min for HPLC to determine the conversion rate. In the reaction system of which the amount of recombinase was 8 wt and 6 wt respectively, after 40 hours, the conversion rate was 100% and 91.62% respectively, and diastereomeric excess of the (2S,5S)-5-hydroxypiperidine-2-carboxylic acid was 98.89%.

2) A E27K+I39K+F28L+S31A amino acid residues mutation in the SEQ ID NO:2 has 98.6% of homology with SEQ ID NO:2, and the amino acid sequence thereof is as shown in SEQ ID NO: 291 in the sequence listing. The mutated enzyme encoded by the sequence was used for catalyzing the L-piperidine acid to prepare (2S,5S)-5-hydroxypiperidine-2-carboxylic acid. 20 ml of the following reaction solution was used. 20 mL of the reaction solution comprised: 50 g/L of L-piperidine acid, 5 wt of recombinase, 62.2 g/L of α-ketoglutarate, 10.2 g/L of L-ascorbic acid, 5 mM of ammonium ferrous sulfate, the reaction pH was 6.5, the reaction temperature was 10 DEG C., and the reaction time was 40 hours. At the end of the reaction, 100 μL of the reaction system was taken, and then 200 μL of acetonitrile was added thereof, and 3000 μL of purified water was added after uniformly mixing, and the supernatant was collected by centrifugation at 10000 rpm for 5 min for HPLC to determine the conversion rate. At 40 hours, the conversion rate was 98.75% respectively, and diastereomeric excess of the (2S,5S)-5-hydroxypiperidine-2-carboxylic acid was 98.30%.

3) Base on the SEQ ID NO:289 sequence which has 78% of homology with the SEQ ID NO:2 and constructed in the embodiment 6, the mutation is performed, after the E27K amino acid residue of the sequence was mutated, the amino acid sequence as shown in SEQ ID NO: 292 in the sequence listing was obtained, the amino acid sequence has 97.8% of the homology with the SEQ ID NO:2. The mutated proline hydroxylase encoded by the sequence was used for catalyzing the L-piperidine acid to prepare (2S,5S)-5-hydroxypiperidine-2-carboxylic acid. 20 ml of the following reaction solution was used. 20 mL of the reaction solution comprised: 50 g/L of L-piperidine acid, 7 wt of recombinase, 62.2 g/L of α-ketoglutarate, 10.2 g/L of L-ascorbic acid, 5 mM of ammonium ferrous sulfate, the reaction pH was 6.5, the reaction temperature was 10 DEG C., and the reaction time was 40 hours. At the end of the reaction, 100 μL of the reaction system was taken, and then 200 μL of acetonitrile was added thereof, and 3000 μL of purified water was added after uniformly mixing, and the supernatant was collected by centrifugation at 10000 rpm for 5 min for HPLC to determine the conversion rate. At 40 hours, the conversion rate was 97.25%, and diastereomeric excess of the (2S,5S)-5-hydroxypiperidine-2-carboxylic acid was 98.40%.

Control Example 1

In a process of the prior art for preparing (2S,5S)-5-hydroxypiperidine-2-carboxylic acid with a recombined proline hydroxylase derived from *Sinorhizobium mehloti*, the highest diastereomeric excess of the (2S,5S)-5-hydroxypiperidine-2-carboxylic acid was 90.7%, and 9.3% of a positional isomer (2S,3R)-3-hydroxypiperidine-2-carboxylic acid was generated (W02013169725A2).

Compared with the embodiment 5, the diastereomeric excess of hydroxylase of SEQ ID NO:2 is 98.36%, and the diastereomeric excess of the control example 1 is 90.7%. It is clear that the selectivity of the hydroxylase of SEQ ID NO:2 in the application is superior to the prior art.

Embodiment 8

Application of hydroxylases in Table 1 and Table 2 for preparing cis-4-hydroxy-L-proline, a reaction process thereof was as shown in FIG. 2.

A proline hydroxylase mutant mutated at K123D amino acid residue encoded by SEQ ID NO: 104 catalyzed L-piperidine acid to prepare the cis-4-hydroxy-L-proline. 20 ml of the following reaction solution was used. 20 mL of the reaction solution comprised: 50 g/L of L-piperidine acid, 5 wt of recombinase, 62.2 g/L of α-ketoglutarate, 10.2 g/L of L-ascorbic acid, 5 mM of ammonium ferrous sulfate, the reaction pH was 6.5, the reaction temperature was 10 DEG C., and the reaction time was 40 hours. At the end of the reaction, 100 μL of the reaction system was taken, and then 200 μL of acetonitrile was added thereof, and 3000 μL of purified water was added after uniformly mixing, and the supernatant was collected by centrifugation at 10000 rpm for 5 min for HPLC to determine the conversion rate. At 40 hours, a conversion rate was 92.36%, and diastereomeric excess was 99.30%.

The proline hydroxylase mutant mutated at S37C+139K+I223V+K123D amino acid residues encoded by SEQ ID NO: 160 catalyzed L-piperidine acid to prepare the cis-4-hydroxy-L-proline. 20 ml of the following reaction solution was used. 20 mL of the reaction solution comprised: 50 g/L of L-piperidine acid, 4 wt of recombinase, 62.2 g/L of α-ketoglutarate, 10.2 g/L of L-ascorbic acid, 5 mM of ammonium ferrous sulfate, the reaction pH was 6.5, the reaction temperature was 10 DEG C., and the reaction time was 40 hours. At the end of the reaction, 100 μL of the reaction system was taken, and then 200 μL of acetonitrile was added thereof, and 3000 μL of purified water was added after uniformly mixing, and the supernatant was collected by centrifugation at 10000 rpm for 5 min for HPLC to determine the conversion rate. At 40 hours, the conversion rate was 99.47%, and the diastereomeric excess was 99.56%.

It is clear that many mutant hydroxylases in Table 1 and Table 2 may be also applied to prepare cis-4-hydroxy-L-proline, and the cis-4-hydroxy-L-proline with high purity and high selectivity may be obtained too.

It is observed from the above description that the above embodiments of the application achieve the following technical effects: through using the SEQ ID NO:2 as a base sequence for screening mutated proline hydroxylases, and by means of genetic engineering, multiple hydroxylases with remarkably improved catalytic activity and selectivity were obtained. These hydroxylases have the characteristics of enabling a substrate conversion rate to be high and catalyzing less specific positional isomers, and are capable of specifically catalyzing hydroxylation of proline derivatives, especially, catalyzing the hydroxylation of L-piperidine acid to generate (2S,5S)-5-hydroxypiperidine-2-carboxylic acid (or named as cis-5-hydroxypiperidine acid) and catalyzing the hydroxylation of L-proline to generate cis-4-hydroxy-L-proline.

The above are only the preferable embodiments of the application, but not intended to limit the application. It is to be understood by those skilled in the art that the application may have various modifications and changes. Any modifications, equivalent replacements, improvements and the like made within the spirit and principles of the application shall fall within the scope of protection of the present application.

What is claimed is:

1. A proline hydroxylase, comprising a protein having the amino acid sequence of SEQ ID NO: 2 with the exception of a mutation of one or more amino acids, wherein the mutation of one or more amino acids must comprise I39, wherein the mutation of I39 is I39K or I39R, and the mutation of one or more amino acids is selected from the group consisting of: H14R, L16N, T25R, F26L, E27K, D30S, S33N, E34N, E34G, E34L, E34S, E34D, Y35W, Y35K, S37W, S37F, S37E, S37N, S37T, S37C, W40F, K41E, D54G, H55Q, S57L, I58T, I58Y, I58A, I58R, I58V, I58S, I58C, K86P, T91A, F95Y, C97Y, I98V, K106V, K106T, K106Q, F111S, K112E, K112R, S154A, K162E, L166M, I118F, I118V, I118R, H119R, H119F, I120V, K123D, K123N, K123Q, K123S, K123I, K123T, T130N, D134G, V135K, N165H, D173G, K209R, I223V and S225A and having proline hydroxylase activity.

2. The proline hydroxylase of claim 1, wherein the mutation comprises any one of the combinations selected from the group consisting of:

E27K+I39K/R, I39K/R+Y35W/K, I39K/R+K123D/1/Q/S, I39K/R+N165H, E27K+I39K/R+K123D/I/Q/S, E27K+Y35W/K+I39K/R, E27K+S37C/E/F/N/W/T+I39K/R, E27K+E34N/G/L/D/S+I39K/R, E27K+I39K/R+D30S, E27K+I39K/R+I118F/V/R, E27K+I39K/R+I98V, E27K+I39K+Y35W/K+S37C/E/F/N/W/T, E27K+I39K/R+S37C/E/F/N/W/T+K123D/I/Q/S, E27K+I39K/R+K106Q+K112E, E27K+I39K/R+Y35W/K+S37C/E/F/N/W/T+K123D/I/Q/S, E27K+I39K /R+S37C/E/F/N/W/T+I58A/C/R/S/T/V/Y, S37C/E/F/N/W/T+I39K/R+I223V+K123D/I/Q/S, E27K+S 37C/E/F/N/W/T+I39K/R+K123D/I/Q/S+I98V, E27K+S37C/E/F/N/W/T+I39K/R+K123D/I/Q/S+I223V, F26L+E27K+I39K/R+K123D/I/Q/S, 1223V+S37C/E/F/N/W/T+E27K+I39K/R, E27K+S37C/E/F/N/W/T+I39K/R+I98V+K123D/I/Q/S+I223V,E27K+S37C/E/F/N/W/T +I39K/R+I58A/C/R/S/T/V/Y+K123D/I/Q/S, E27K+I39K/R+K123D/I/Q/S+N165H, T25G/R+E27K+S37C/E/F/N/W/T+I39K/R+I58A/C/R/S/T/V/Y, E27K+S37C/E/F/N/W/T+I39K/R+I58A/C/R/S/T/V/Y+K86P, E27K+D30S+I39K/R+I58A/C/R/S/T/V/Y+K112E, S37C/E/F/N/W/T+I39K/R+N165H, E27K+E34N/G/L/D/S+I39K/R+158 A/C/R/S/T/V/Y+I223V, E27K+S37C/E/F/N/W/T+I39K/R+158A/C/R/S/T/V/Y+D173G, E27K+S37C/E/F/N/W/T+I39K/R+I58A/C/R/S/T/V/Y+D173G+I118F/V/R, E27K+E34N/G/L/D/S+S3 7C/E/F/N/W/T+I39K/R+I58A/C/R/S/T/V/Y, E27K+E34N/G/L/D/S+S37C/E/F/N/W/T+I39K/R+I58A /C/R/S/T/V/Y+D173G, E27K+S37C/E/F/N/W/T+I39K/R+I58A/C/R/S/T/V/Y+D173G+K123D/I/Q/S, E27K+S37C/E/F/N/W/T+I39K/R+I58A/C/R/S/T/V/Y+D173G+K123D/I/Q/S+I118F/V/R, E27K+S37C /E/F/N/W/T+I39K/R+I58A/C/R/S/T/V/Y+D173G+K123D/I/Q/S+N165H, E27K+E34N/G/L/D/S+S37 C/E/F/N/W/T+I39K/R+I58A/C/R/S/T/V/+D173G+K123D/I/Q/S, H14R+E27K+D30S+E34N/G/L/D/S+I39K/R+I98V+K106V/T/Q+K112E/R+I223V, T25G/R+E27K+S37C/E/F/N/W/T+I39K/R+I58A/C/R/S/TA//Y+D173G+K123D/I/Q/S+I118F/V/R+N 165H, H14R+E27K+E34N/G/L/D/S+I39K/R+I98V+K106V/T/Q+K112E/R+I223V, H14R+E27K+E34N/G/L/D/S+S37C/E/F/N/W/T+I39K/R+I98V+K106V/T/Q+K112E/R+I223V, H14R+E27K+E34N/G/L/D/S+Y35W/K+I39K/R+I98V+K106V/T/Q+K112E/R+I223V, H14R+E27K+E34N/G/L/D/S+I39K/R+I98V+K106V/T/Q+K112E/R+K123D/I/Q/S+I223V,H14R+E27 K+E34N/G/L/D+I39K/R+I58A/C/R/S/T/V/Y+I98V+K106V/T/Q+K112E/R+I223V and H14R+E27K+E34N/G/L/D/S+I39K/R+I98V+K106V/T/Q+K112E/R+I118F/V/R+I223V, wherein '/' represents 'or'.

3. A method for producing an L-hydroxyproline derivative, wherein the method comprises:

contacting an L-proline derivative substrate with the proline hydroxylase of claim 1 to catalyze hydroxylation of the L-proline derivative substrate, to obtain the L-hydroxyproline derivative as shown in general formula (I):

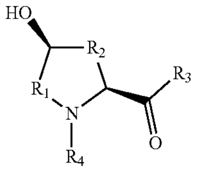

(I)

wherein $R_1$ is selected from $C_1$-$C_5$ alkylene or $C_2$-$C_5$ alkenylene; $R_2$ is selected form $C_0$-$C_4$ alkylene or $C_2$-$C_4$ alkenylene; $R_3$ is selected from hydroxyl, amino, $C_1$-$C_6$ alkoxy, aryloxy, $C_1$-$C_6$ alkyl sulfenyl or $C_1$-$C_6$ aryl sulfenyl; and $R_4$ is selected from hydrogen, $C_1$-$C_6$ alkyl, $C_2$-$C_6$ alkenyl or $C_2$-$C_6$ alkynyl.

4. The method of claim 3, wherein the method further comprises: adding a-oxoglutarate and $O_2$ as a common substrate and adding iron ions as a cofactor.

5. The method of claim 3, wherein the L-hydroxyproline derivative is cis-4-hydroxy-L-proline or (2S,5S)-5-hydroxypiperidine-2-carboxylic acid.

6. The method of claim 3, wherein the proline hydroxylase catalyzes hydroxylation of the L-proline derivative substrate in a temperature of 5-45° C.

* * * * *

SEQUENCE LISTING

```
<160> NUMBER OF SEQ ID NOS: 292

<210> SEQ ID NO 1
<211> LENGTH: 831
<212> TYPE: DNA
<213> ORGANISM: Kordia jejudonensis

<400> SEQUENCE: 1

atggaatcaa aaataatagg caaagtaaat tttgaagaac acttactgga caaagagctg      60

aaattgatag atactttcga attcaatgat tcgtacagtg aatatgcatc aggaatttgg     120

aaaacatgca tgctttggaa tcgctccgga cagaaagatg atcatttatc tatagaacat     180

gatacgtatg taaaaccgac agaatatggt aaacaacttg catatgtcaa tgaaattata     240

gcaaatactt tcaaaaaaga gcatataaaa acggttcgac tttttatgtg tattaacgga     300

ttaattattc cacataaaga ctatttagaa tttaaaaaag gatttacacg aattcacatt     360

ccgcttaaaa ttaacgaaca tgcgcttact tccgaagaag atgttgtgta caatatgcaa     420

aaaggcgaaa tatggtttat agaaggaaga aaaattcaca gtgccgccaa cttttcaaaa     480

gtaaagcgga tcaatttagt gattgacttt gctcctgata ttccgtttga agaattattt     540

ctaaactcgg aaaattacca accaaatttg attccaaaaa ttagccaacg aacacagcta     600

aaagaagaag aattaggcta tataaaagga ttatctaaga tcattaatga aatgaacttt     660

gacgatattt tatcaatact ctccaaaata catttttata gaaatgtgtc tagcgaactg     720

gttttcggtt ggttagatga aattgcaact gcttctaaca attataacat tcaacgaaaa     780

gcacaagaag tgaccgattt attaataaga aaaggaccaa taaataatta a              831


<210> SEQ ID NO 2
<211> LENGTH: 276
<212> TYPE: PRT
<213> ORGANISM: Kordia jejudonensis

<400> SEQUENCE: 2

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
```

-continued

```
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 3
<211> LENGTH: 831
<212> TYPE: DNA
<213> ORGANISM: Artificial Sequence
<220> FEATURE:
<223> OTHER INFORMATION: condon-optimizated DNA sequence

<400> SEQUENCE: 3

```
atggaatcca agatcatcgg taaagtcaac ttcgaggagc atctgctgga taaagagctg     60

aaactgatcg acactttcga gttcaacgac agctacagcg aatacgcttc tggtatttgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780
```

-continued gcgcaggaag taaccgatct gctgattcgc aaaggcccga ttaataacta a 831

<210> SEQ ID NO 4
<211> LENGTH: 276
<212> TYPE: PRT
<213> ORGANISM: Artificial Sequence
<220> FEATURE:
<223> OTHER INFORMATION: condon-optimizated sequence drived from Kordia jejudonensis

<400> SEQUENCE: 4

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 5
<211> LENGTH: 831
<212> TYPE: DNA
<213> ORGANISM: Artificial Sequence
<220> FEATURE:
<223> OTHER INFORMATION: gene sequence of H14R mutant

<400> SEQUENCE: 5
atggaatcca agatcatcgg taaagtcaac ttcgaggagc gtctgctgga taaagagctg 60

-continued

```
aaactgatcg acactttcga gttcaacgac agctacagcg aatacgcttc tggtatttgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 6
<211> LENGTH: 276
<212> TYPE: PRT
<213> ORGANISM: Artificial Sequence
<220> FEATURE:
<223> OTHER INFORMATION: amino acid sequence of H14R mutant

<400> SEQUENCE: 6

```
Met Glu Ser Lys Ile Ile Gly Lys Val Asn Phe Glu Glu Arg Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220
```

-continued

Ser Ile Leu Ser Lys Ile His Phe Tyr Arg Asn Val Ser Ser Glu Leu
225 230 235 240

Val Phe Gly Trp Leu Asp Glu Ile Ala Thr Ala Ser Asn Asn Tyr Asn
245 250 255

Ile Gln Arg Lys Ala Gln Glu Val Thr Asp Leu Leu Ile Arg Lys Gly
260 265 270

Pro Ile Asn Asn
275

<210> SEQ ID NO 7
<211> LENGTH: 831
<212> TYPE: DNA
<213> ORGANISM: Artificial Sequence
<220> FEATURE:
<223> OTHER INFORMATION: gene sequence of S16N mutant

<400> SEQUENCE: 7
atggaatcca agatcatcgg taaagtcaac ttcgaggagc atctgaatga taaagagctg 60
aaactgatcg acactttcga gttcaacgac agctacagcg aatacgcttc tggtatttgg 120
aagacttgca tgctgtggaa ccgttctggt cagaaagatg accatctgtc tattgaacat 180
gatacctacg tgaaacctac tgaatacggc aaacagctgg catacgtaaa cgaaatcatc 240
gctaacacct ttaagaaaga acacatcaag acggtgcgtc tgttcatgtg tatcaacggc 300
ctgatcatcc cacacaaaga ctacctggaa ttcaagaaag gcttcacccg tatccacatc 360
ccgctgaaaa tcaacgaaca cgcactgacc tctgaagaag atgttgttta caacatgcag 420
aaaggtgaaa tttggttcat cgaaggccgt aaaatccaca gcgctgccaa tttcagcaaa 480
gtgaaacgta tcaacctggt catcgacttc gcgccggata ttccgtttga agaactgttc 540
ctgaattctg agaactatca accgaacctg atcccgaaaa tctctcaacg tacccagctg 600
aaagaagaag agctgggtta tatcaaaggt ctgtctaaaa ttatcaatga aatgaacttt 660
gacgacatcc tgtccattct gagcaaaatt cacttctatc gcaacgtttc ctccgaactg 720
gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 8
<211> LENGTH: 276
<212> TYPE: PRT
<213> ORGANISM: Artificial Sequence
<220> FEATURE:
<223> OTHER INFORMATION: amino acid of S16N mutant

<400> SEQUENCE: 8

Met Glu Ser Lys Ile Ile Gly Lys Val Asn Phe Glu Glu His Leu Asn
1 5 10 15

Asp Lys Glu Leu Lys Leu Ile Asp Thr Phe Glu Phe Asn Asp Ser Tyr
20 25 30

Ser Glu Tyr Ala Ser Gly Ile Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys

```
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 9
<211> LENGTH: 831
<212> TYPE: DNA
<213> ORGANISM: Artificial Sequence
<220> FEATURE:
<223> OTHER INFORMATION: gene sequence of T25G mutant

<400> SEQUENCE: 9

atggaatcca agatcatcgg taaagtcaac ttcgaggagc atctgctgga taaagagctg     60

aaactgatcg acggtttcga gttcaacgac agctacagcg aatacgcttc tggtatttgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831


<210> SEQ ID NO 10
<211> LENGTH: 276
<212> TYPE: PRT
<213> ORGANISM: Artificial Sequence
<220> FEATURE:
```

-continued

<223> OTHER INFORMATION: amino acid sequence of T25G mutant

<400> SEQUENCE: 10

```
Met Glu Ser Lys Ile Ile Gly Lys Val Asn Phe Glu Glu His Leu Leu
1               5                   10                  15

Asp Lys Glu Leu Lys Leu Ile Asp Gly Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 11
<211> LENGTH: 831
<212> TYPE: DNA
<213> ORGANISM: Artificial Sequence
<220> FEATURE:
<223> OTHER INFORMATION: gene sequence of T25R mutant

<400> SEQUENCE: 11

```
atggaatcca agatcatcgg taaagtcaac ttcgaggagc atctgctgga taaagagctg      60

aaactgatcg accgtttcga gttcaacgac agctacagcg aatacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360
```

-continued

```
ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

```
<210> SEQ ID NO 12
<211> LENGTH: 276
<212> TYPE: PRT
<213> ORGANISM: Artificial Sequence
<220> FEATURE:
<223> OTHER INFORMATION: amino acid sequence of T25R mutant

<400> SEQUENCE: 12

Met Glu Ser Lys Ile Ile Gly Lys Val Asn Phe Glu Glu His Leu Leu
1               5                   10                  15

Asp Lys Glu Leu Lys Leu Ile Asp Arg Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
```

275

<210> SEQ ID NO 13
<211> LENGTH: 831
<212> TYPE: DNA
<213> ORGANISM: Artificial Sequence
<220> FEATURE:
<223> OTHER INFORMATION: genge sequence of F26L mutant

<400> SEQUENCE: 13

```
atggaatcca agatcatcgg taaagtcaac ttcgaggagc atctgctgga taaagagctg      60

aaactgatcg acactctgga gttcaacgac agctacagcg aatacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831
```

<210> SEQ ID NO 14
<211> LENGTH: 276
<212> TYPE: PRT
<213> ORGANISM: Artificial Sequence
<220> FEATURE:
<223> OTHER INFORMATION: amino acid sequence of F26L mutant

<400> SEQUENCE: 14

```
Met Glu Ser Lys Ile Ile Gly Lys Val Asn Phe Glu Glu His Leu Leu
1               5                   10                  15

Asp Lys Glu Leu Lys Leu Ile Asp Thr Leu Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160
```

```
Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 15
<211> LENGTH: 831
<212> TYPE: DNA
<213> ORGANISM: Artificial Sequence
<220> FEATURE:
<223> OTHER INFORMATION: gene sequence of E27K mutant

<400> SEQUENCE: 15

atggaatcca agatcatcgg taaagtcaac ttcgaggagc atctgctgga taaagagctg     60

aaactgatcg acactttcaa attcaacgac agctacagcg aatacgcttc tggtatttgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831


<210> SEQ ID NO 16
<211> LENGTH: 276
<212> TYPE: PRT
<213> ORGANISM: Artificial Sequence
<220> FEATURE:
<223> OTHER INFORMATION: amino acid sequence of E27K mutant

<400> SEQUENCE: 16

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30
```

-continued

```
Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 17
<211> LENGTH: 831
<212> TYPE: DNA
<213> ORGANISM: Artificial Sequence
<220> FEATURE:
<223> OTHER INFORMATION: gene sequence of D30S mutant

<400> SEQUENCE: 17

```
atggaatcca agatcatcgg taaagtcaac ttcgaggagc atctgctgga taaagagctg     60

aaactgatcg acactttcga gttcaacagc agctacagcg aatacgcttc tggtatttgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660
```

gacgacatcc tgtccattct gagcaaaatt cacttctatc gcaacgtttc ctccgaactg 720
gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 18
<211> LENGTH: 276
<212> TYPE: PRT
<213> ORGANISM: Artificial Sequence
<220> FEATURE:
<223> OTHER INFORMATION: amino acid sequence of D30S mutant

<400> SEQUENCE: 18

Met Glu Ser Lys Ile Ile Gly Lys Val Asn Phe Glu Glu His Leu Leu
1 5 10 15

Asp Lys Glu Leu Lys Leu Ile Asp Thr Phe Glu Phe Asn Ser Ser Tyr
20 25 30

Ser Glu Tyr Ala Ser Gly Ile Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys
100 105 110

Lys Gly Phe Thr Arg Ile His Ile Pro Leu Lys Ile Asn Glu His Ala
115 120 125

Leu Thr Ser Glu Glu Asp Val Val Tyr Asn Met Gln Lys Gly Glu Ile
130 135 140

Trp Phe Ile Glu Gly Arg Lys Ile His Ser Ala Ala Asn Phe Ser Lys
145 150 155 160

Val Lys Arg Ile Asn Leu Val Ile Asp Phe Ala Pro Asp Ile Pro Phe
165 170 175

Glu Glu Leu Phe Leu Asn Ser Glu Asn Tyr Gln Pro Asn Leu Ile Pro
180 185 190

Lys Ile Ser Gln Arg Thr Gln Leu Lys Glu Glu Glu Leu Gly Tyr Ile
195 200 205

Lys Gly Leu Ser Lys Ile Ile Asn Glu Met Asn Phe Asp Asp Ile Leu
210 215 220

Ser Ile Leu Ser Lys Ile His Phe Tyr Arg Asn Val Ser Ser Glu Leu
225 230 235 240

Val Phe Gly Trp Leu Asp Glu Ile Ala Thr Ala Ser Asn Asn Tyr Asn
245 250 255

Ile Gln Arg Lys Ala Gln Glu Val Thr Asp Leu Leu Ile Arg Lys Gly
260 265 270

Pro Ile Asn Asn
275

<210> SEQ ID NO 19
<211> LENGTH: 831
<212> TYPE: DNA
<213> ORGANISM: Artificial Sequence
<220> FEATURE:
<223> OTHER INFORMATION: gene sequence of S33N mutant

<400> SEQUENCE: 19

```
atggaatcca agatcatcgg taaagtcaac ttcgaggagc atctgctgga taaagagctg     60
aaactgatcg acactttcga gttcaacgac agctacaatg aatacgcttc tggtatttgg    120
aagacttgca tgctgtggaa ccgttctggt cagaaagatg accatctgtc tattgaacat    180
gatacctacg tgaaacctac tgaatacggc aaacagctgg catacgtaaa cgaaatcatc    240
gctaacacct ttaagaaaga acacatcaag acggtgcgtc tgttcatgtg tatcaacggc    300
ctgatcatcc cacacaaaga ctacctggaa ttcaagaaag gcttcacccg tatccacatc    360
ccgctgaaaa tcaacgaaca cgcactgacc tctgaagaag atgttgttta caacatgcag    420
aaaggtgaaa tttggttcat cgaaggccgt aaaatccaca gcgctgccaa tttcagcaaa    480
gtgaaacgta tcaacctggt catcgacttc gcgccggata ttccgtttga agaactgttc    540
ctgaattctg agaactatca accgaacctg atcccgaaaa tctctcaacg tacccagctg    600
aaagaagaag agctgggtta tatcaaaggt ctgtctaaaa ttatcaatga aatgaacttt    660
gacgacatcc tgtccattct gagcaaaatt cacttctatc gcaacgtttc ctccgaactg    720
gtttttggct ggctggacga aattgccacg gcgtccaaca actataacat tcagcgcaaa    780
gcgcaggaag taaccgatct gctgattcgc aaaggcccga ttaataacta a             831
```

<210> SEQ ID NO 20
<211> LENGTH: 276
<212> TYPE: PRT
<213> ORGANISM: Artificial Sequence
<220> FEATURE:
<223> OTHER INFORMATION: amino acid sequence of S33N mutant

<400> SEQUENCE: 20

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Asn Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205
```

-continued

```
Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 21
<211> LENGTH: 831
<212> TYPE: DNA
<213> ORGANISM: Artificial Sequence
<220> FEATURE:
<223> OTHER INFORMATION: gene sequence of E34N mutant

<400> SEQUENCE: 21

atggaatcca agatcatcgg taaagtcaac ttcgaggagc atctgctgga taaagagctg      60

aaactgatcg acactttcga gttcaacgac agctacagca attacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 22
<211> LENGTH: 276
<212> TYPE: PRT
<213> ORGANISM: Artificial Sequence
<220> FEATURE:
<223> OTHER INFORMATION: amino acid sequence of E34N mutant

<400> SEQUENCE: 22

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Asn Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
```

```
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 23
<211> LENGTH: 831
<212> TYPE: DNA
<213> ORGANISM: Artificial Sequence
<220> FEATURE:
<223> OTHER INFORMATION: gene sequence of E34G mutant

<400> SEQUENCE: 23

atggaatcca agatcatcgg taaagtcaac ttcgaggagc atctgctgga taaagagctg      60

aaactgatcg acactttcga gttcaacgac agctacagcg gttacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 24
<211> LENGTH: 276
```

<212> TYPE: PRT
<213> ORGANISM: Artificial Sequence
<220> FEATURE:
<223> OTHER INFORMATION: amino acid sequence of E34G mutant

<400> SEQUENCE: 24

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Gly Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 25
<211> LENGTH: 831
<212> TYPE: DNA
<213> ORGANISM: Artificial Sequence
<220> FEATURE:
<223> OTHER INFORMATION: gene sequence of E34L mutant

<400> SEQUENCE: 25

```
atggaatcca agatcatcgg taaagtcaac ttcgaggagc atctgctgga taaagagctg      60

aaactgatcg acactttcga gttcaacgac agctacagcc tgtacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240
```

```
gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 26
<211> LENGTH: 276
<212> TYPE: PRT
<213> ORGANISM: Artificial Sequence
<220> FEATURE:
<223> OTHER INFORMATION: amino acid sequence of E34L mutant

<400> SEQUENCE: 26

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Leu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
```

260 265 270

Pro Ile Asn Asn
275

<210> SEQ ID NO 27
<211> LENGTH: 831
<212> TYPE: DNA
<213> ORGANISM: Artificial Sequence
<220> FEATURE:
<223> OTHER INFORMATION: gene sequence of E34D mutant

<400> SEQUENCE: 27
atggaatcca agatcatcgg taaagtcaac ttcgaggagc atctgctgga taaagagctg 60
aaactgatcg acactttcga gttcaacgac agctacagcg attacgcttc tggtatttgg 120
aagacttgca tgctgtggaa ccgttctggt cagaaagatg accatctgtc tattgaacat 180
gatacctacg tgaaacctac tgaatacggc aaacagctgg catacgtaaa cgaaatcatc 240
gctaacacct ttaagaaaga acacatcaag acggtgcgtc tgttcatgtg tatcaacggc 300
ctgatcatcc cacacaaaga ctacctggaa ttcaagaaag gcttcacccg tatccacatc 360
ccgctgaaaa tcaacgaaca cgcactgacc tctgaagaag atgttgttta caacatgcag 420
aaaggtgaaa tttggttcat cgaaggccgt aaaatccaca gcgctgccaa tttcagcaaa 480
gtgaaacgta tcaacctggt catcgacttc gcgccggata ttccgtttga agaactgttc 540
ctgaattctg agaactatca accgaacctg atcccgaaaa tctctcaacg tacccagctg 600
aaagaagaag agctgggtta tatcaaaggt ctgtctaaaa ttatcaatga aatgaacttt 660
gacgacatcc tgtccattct gagcaaaatt cacttctatc gcaacgtttc ctccgaactg 720
gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 28
<211> LENGTH: 276
<212> TYPE: PRT
<213> ORGANISM: Artificial Sequence
<220> FEATURE:
<223> OTHER INFORMATION: amino acid sequence of E34D mutant

<400> SEQUENCE: 28

Met Glu Ser Lys Ile Ile Gly Lys Val Asn Phe Glu Glu His Leu Leu
1 5 10 15

Asp Lys Glu Leu Lys Leu Ile Asp Thr Phe Glu Phe Asn Asp Ser Tyr
20 25 30

Ser Asp Tyr Ala Ser Gly Ile Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys
100 105 110

Lys Gly Phe Thr Arg Ile His Ile Pro Leu Lys Ile Asn Glu His Ala
115 120 125

Leu Thr Ser Glu Glu Asp Val Val Tyr Asn Met Gln Lys Gly Glu Ile
130 135 140

-continued

Trp Phe Ile Glu Gly Arg Lys Ile His Ser Ala Ala Asn Phe Ser Lys
145 150 155 160

Val Lys Arg Ile Asn Leu Val Ile Asp Phe Ala Pro Asp Ile Pro Phe
165 170 175

Glu Glu Leu Phe Leu Asn Ser Glu Asn Tyr Gln Pro Asn Leu Ile Pro
180 185 190

Lys Ile Ser Gln Arg Thr Gln Leu Lys Glu Glu Glu Leu Gly Tyr Ile
195 200 205

Lys Gly Leu Ser Lys Ile Ile Asn Glu Met Asn Phe Asp Asp Ile Leu
210 215 220

Ser Ile Leu Ser Lys Ile His Phe Tyr Arg Asn Val Ser Ser Glu Leu
225 230 235 240

Val Phe Gly Trp Leu Asp Glu Ile Ala Thr Ala Ser Asn Asn Tyr Asn
245 250 255

Ile Gln Arg Lys Ala Gln Glu Val Thr Asp Leu Leu Ile Arg Lys Gly
260 265 270

Pro Ile Asn Asn
275

<210> SEQ ID NO 29
<211> LENGTH: 831
<212> TYPE: DNA
<213> ORGANISM: Artificial Sequence
<220> FEATURE:
<223> OTHER INFORMATION: gene sequence of E34S mutant

<400> SEQUENCE: 29
atggaatcca agatcatcgg taaagtcaac ttcgaggagc atctgctgga taaagagctg 60
aaactgatcg acactttcga gttcaacgac agctacagca gctacgcttc tggtatttgg 120
aagacttgca tgctgtggaa ccgttctggt cagaaagatg accatctgtc tattgaacat 180
gatacctacg tgaaacctac tgaatacggc aaacagctgg catacgtaaa cgaaatcatc 240
gctaacacct ttaagaaaga acacatcaag acggtgcgtc tgttcatgtg tatcaacggc 300
ctgatcatcc cacacaaaga ctacctggaa ttcaagaaag gcttcacccg tatccacatc 360
ccgctgaaaa tcaacgaaca cgcactgacc tctgaagaag atgttgttta caacatgcag 420
aaaggtgaaa tttggttcat cgaaggccgt aaaatccaca gcgctgccaa tttcagcaaa 480
gtgaaacgta tcaacctggt catcgacttc gcgccggata ttccgtttga agaactgttc 540
ctgaattctg agaactatca accgaacctg atcccgaaaa tctctcaacg tacccagctg 600
aaagaagaag agctgggtta tatcaaaggt ctgtctaaaa ttatcaatga aatgaacttt 660
gacgacatcc tgtccattct gagcaaaatt cacttctatc gcaacgtttc ctccgaactg 720
gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 30
<211> LENGTH: 276
<212> TYPE: PRT
<213> ORGANISM: Artificial Sequence
<220> FEATURE:
<223> OTHER INFORMATION: amino acid sequence of E34S mutant

<400> SEQUENCE: 30

Met Glu Ser Lys Ile Ile Gly Lys Val Asn Phe Glu Glu His Leu Leu
1 5 10 15

-continued

```
Asp Lys Glu Leu Lys Leu Ile Asp Thr Phe Glu Phe Asn Asp Ser Tyr
            20                  25                  30

Ser Ser Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 31
<211> LENGTH: 831
<212> TYPE: DNA
<213> ORGANISM: Artificial Sequence
<220> FEATURE:
<223> OTHER INFORMATION: gene sequence of Y35W mutant

<400> SEQUENCE: 31

```
atggaatcca agatcatcgg taaagtcaac ttcgaggagc atctgctgga taaagagctg      60

aaactgatcg acactttcga gttcaacgac agctacagcg aatgggcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540
```

-continued

```
ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 32
<211> LENGTH: 276
<212> TYPE: PRT
<213> ORGANISM: Artificial Sequence
<220> FEATURE:
<223> OTHER INFORMATION: amino acid sequence of Y35W mutant

<400> SEQUENCE: 32

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Trp Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 33
<211> LENGTH: 831
<212> TYPE: DNA
<213> ORGANISM: Artificial Sequence
<220> FEATURE:
<223> OTHER INFORMATION: gene sequence of Y35K mutant

<400> SEQUENCE: 33

```
atggaatcca agatcatcgg taaagtcaac ttcgaggagc atctgctgga taaagagctg      60
aaactgatcg acactttcga gttcaacgac agctacagcg aaaaagcttc tggtatttgg     120
aagacttgca tgctgtggaa ccgttctggt cagaaagatg accatctgtc tattgaacat     180
gatacctacg tgaaacctac tgaatacggc aaacagctgg catacgtaaa cgaaatcatc     240
gctaacacct ttaagaaaga acacatcaag acggtgcgtc tgttcatgtg tatcaacggc     300
ctgatcatcc cacacaaaga ctacctggaa ttcaagaaag gcttcacccg tatccacatc     360
ccgctgaaaa tcaacgaaca cgcactgacc tctgaagaag atgttgttta caacatgcag     420
aaaggtgaaa tttggttcat cgaaggccgt aaaatccaca gcgctgccaa tttcagcaaa     480
gtgaaacgta tcaacctggt catcgacttc gcgccggata ttccgtttga agaactgttc     540
ctgaattctg agaactatca accgaacctg atcccgaaaa tctctcaacg tacccagctg     600
aaagaagaag agctgggtta tatcaaaggt ctgtctaaaa ttatcaatga aatgaacttt     660
gacgacatcc tgtccattct gagcaaaatt cacttctatc gcaacgtttc ctccgaactg     720
gtttttggct ggctggacga aattgccacg gcgtccaaca actataacat tcagcgcaaa     780
gcgcaggaag taaccgatct gctgattcgc aaaggcccga ttaataacta a              831
```

<210> SEQ ID NO 34
<211> LENGTH: 276
<212> TYPE: PRT
<213> ORGANISM: Artificial Sequence
<220> FEATURE:
<223> OTHER INFORMATION: amino acid sequence of Y35K mutant

<400> SEQUENCE: 34

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Lys Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190
```

```
Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 35
<211> LENGTH: 831
<212> TYPE: DNA
<213> ORGANISM: Artificial Sequence
<220> FEATURE:
<223> OTHER INFORMATION: gene sequence of S37W mutant

<400> SEQUENCE: 35

atggaatcca agatcatcgg taaagtcaac ttcgaggagc atctgctgga taaagagctg      60

aaactgatcg acactttcga gttcaacgac agctacagcg aatacgcttg ggtatttgg      120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 36
<211> LENGTH: 276
<212> TYPE: PRT
<213> ORGANISM: Artificial Sequence
<220> FEATURE:
<223> OTHER INFORMATION: amino acid sequence of S37W mutant

<400> SEQUENCE: 36

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Trp Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
```

-continued

```
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 37
<211> LENGTH: 831
<212> TYPE: DNA
<213> ORGANISM: Artificial Sequence
<220> FEATURE:
<223> OTHER INFORMATION: gene sequence of S37F mutant

<400> SEQUENCE: 37

atggaatcca agatcatcgg taaagtcaac ttcgaggagc atctgctgga taaagagctg      60

aaactgatcg acactttcga gttcaacgac agctacagcg aatacgcttt tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831
```

<210> SEQ ID NO 38
<211> LENGTH: 276
<212> TYPE: PRT
<213> ORGANISM: Artificial Sequence
<220> FEATURE:
<223> OTHER INFORMATION: amino acid sequence of S37F mutant

<400> SEQUENCE: 38

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Phe Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 39
<211> LENGTH: 831
<212> TYPE: DNA
<213> ORGANISM: Artificial Sequence
<220> FEATURE:
<223> OTHER INFORMATION: gene sequence of S37E mutant

<400> SEQUENCE: 39

```
atggaatcca agatcatcgg taaagtcaac ttcgaggagc atctgctgga taaagagctg      60

aaactgatcg acactttcga gttcaacgac agctacagcg aatacgctga aggtatttgg     120

aagacttgca tgctgtggaa ccgttctggt cagaaagatg accatctgtc tattgaacat     180
```

-continued

```
gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

```
<210> SEQ ID NO 40
<211> LENGTH: 276
<212> TYPE: PRT
<213> ORGANISM: Artificial Sequence
<220> FEATURE:
<223> OTHER INFORMATION: amino acid sequence of S37E mutant

<400> SEQUENCE: 40

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Glu Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
```

```
            245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 41
<211> LENGTH: 831
<212> TYPE: DNA
<213> ORGANISM: Artificial Sequence
<220> FEATURE:
<223> OTHER INFORMATION: gene sequence of S37N mutant

<400> SEQUENCE: 41

atggaatcca agatcatcgg taaagtcaac ttcgaggagc atctgctgga taaagagctg      60

aaactgatcg acactttcga gttcaacgac agctacagcg aatacgctaa tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 42
<211> LENGTH: 276
<212> TYPE: PRT
<213> ORGANISM: Artificial Sequence
<220> FEATURE:
<223> OTHER INFORMATION: amino acid sequence of S37N mutant

<400> SEQUENCE: 42

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Asn Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125
```

```
Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 43
<211> LENGTH: 831
<212> TYPE: DNA
<213> ORGANISM: Artificial Sequence
<220> FEATURE:
<223> OTHER INFORMATION: gene sequence of S37T mutant

<400> SEQUENCE: 43

```
atggaatcca agatcatcgg taaagtcaac ttcgaggagc atctgctgga taaagagctg     60

aaactgatcg acactttcga gttcaacgac agctacagcg aatacgctac cggtatttgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 44
<211> LENGTH: 276
<212> TYPE: PRT
<213> ORGANISM: Artificial Sequence
<220> FEATURE:
<223> OTHER INFORMATION: amino acid sequence of S37T mutant

<400> SEQUENCE: 44

-continued

Met Glu Ser Lys Ile Ile Gly Lys Val Asn Phe Glu Glu His Leu Leu
1 5 10 15

Asp Lys Glu Leu Lys Leu Ile Asp Thr Phe Glu Phe Asn Asp Ser Tyr
20 25 30

Ser Glu Tyr Ala Thr Gly Ile Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys
100 105 110

Lys Gly Phe Thr Arg Ile His Ile Pro Leu Lys Ile Asn Glu His Ala
115 120 125

Leu Thr Ser Glu Glu Asp Val Val Tyr Asn Met Gln Lys Gly Glu Ile
130 135 140

Trp Phe Ile Glu Gly Arg Lys Ile His Ser Ala Ala Asn Phe Ser Lys
145 150 155 160

Val Lys Arg Ile Asn Leu Val Ile Asp Phe Ala Pro Asp Ile Pro Phe
165 170 175

Glu Glu Leu Phe Leu Asn Ser Glu Asn Tyr Gln Pro Asn Leu Ile Pro
180 185 190

Lys Ile Ser Gln Arg Thr Gln Leu Lys Glu Glu Glu Leu Gly Tyr Ile
195 200 205

Lys Gly Leu Ser Lys Ile Ile Asn Glu Met Asn Phe Asp Asp Ile Leu
210 215 220

Ser Ile Leu Ser Lys Ile His Phe Tyr Arg Asn Val Ser Ser Glu Leu
225 230 235 240

Val Phe Gly Trp Leu Asp Glu Ile Ala Thr Ala Ser Asn Asn Tyr Asn
245 250 255

Ile Gln Arg Lys Ala Gln Glu Val Thr Asp Leu Leu Ile Arg Lys Gly
260 265 270

Pro Ile Asn Asn
275

<210> SEQ ID NO 45
<211> LENGTH: 831
<212> TYPE: DNA
<213> ORGANISM: Artificial Sequence
<220> FEATURE:
<223> OTHER INFORMATION: gene sequence of S37C mutant

<400> SEQUENCE: 45
atggaatcca agatcatcgg taaagtcaac ttcgaggagc atctgctgga taaagagctg 60
aaactgatcg acactttcga gttcaacgac agctacagcg aatacgcttg tggtatttgg 120
aagacttgca tgctgtggaa ccgttctggt cagaaagatg accatctgtc tattgaacat 180
gatacctacg tgaaacctac tgaatacggc aaacagctgg catacgtaaa cgaaatcatc 240
gctaacacct ttaagaaaga acacatcaag acggtgcgtc tgttcatgtg tatcaacggc 300
ctgatcatcc cacacaaaga ctacctggaa ttcaagaaag gcttcacccg tatccacatc 360
ccgctgaaaa tcaacgaaca cgcactgacc tctgaagaag atgttgttta caacatgcag 420
aaaggtgaaa tttggttcat cgaaggccgt aaaatccaca gcgctgccaa tttcagcaaa 480

```
gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 46
<211> LENGTH: 276
<212> TYPE: PRT
<213> ORGANISM: Artificial Sequence
<220> FEATURE:
<223> OTHER INFORMATION: amino acid sequence of S37C mutant

<400> SEQUENCE: 46

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Cys Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 47

<211> LENGTH: 831
<212> TYPE: DNA
<213> ORGANISM: Artificial Sequence
<220> FEATURE:
<223> OTHER INFORMATION: gene sequence of I39K mutant

<400> SEQUENCE: 47
atggaatcca agatcatcgg taaagtcaac ttcgaggagc atctgctgga taaagagctg 60
aaactgatcg acactttcga gttcaacgac agctacagcg aatacgcttc tggtaaatgg 120
aagacttgca tgctgtggaa ccgttctggt cagaaagatg accatctgtc tattgaacat 180
gatacctacg tgaaacctac tgaatacggc aaacagctgg catacgtaaa cgaaatcatc 240
gctaacacct ttaagaaaga acacatcaag acggtgcgtc tgttcatgtg tatcaacggc 300
ctgatcatcc cacacaaaga ctacctggaa ttcaagaaag gcttcacccg tatccacatc 360
ccgctgaaaa tcaacgaaca cgcactgacc tctgaagaag atgttgttta caacatgcag 420
aaaggtgaaa tttggttcat cgaaggccgt aaaatccaca gcgctgccaa tttcagcaaa 480
gtgaaacgta tcaacctggt catcgacttc gcgccggata ttccgtttga agaactgttc 540
ctgaattctg agaactatca accgaacctg atcccgaaaa tctctcaacg tacccagctg 600
aaagaagaag agctgggtta tatcaaaggt ctgtctaaaa ttatcaatga aatgaacttt 660
gacgacatcc tgtccattct gagcaaaatt cacttctatc gcaacgtttc ctccgaactg 720
gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 48
<211> LENGTH: 276
<212> TYPE: PRT
<213> ORGANISM: Artificial Sequence
<220> FEATURE:
<223> OTHER INFORMATION: amino acid sequence of I39K mutant

<400> SEQUENCE: 48

Met Glu Ser Lys Ile Ile Gly Lys Val Asn Phe Glu Glu His Leu Leu
1 5 10 15

Asp Lys Glu Leu Lys Leu Ile Asp Thr Phe Glu Phe Asn Asp Ser Tyr
20 25 30

Ser Glu Tyr Ala Ser Gly Lys Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys
100 105 110

Lys Gly Phe Thr Arg Ile His Ile Pro Leu Lys Ile Asn Glu His Ala
115 120 125

Leu Thr Ser Glu Glu Asp Val Val Tyr Asn Met Gln Lys Gly Glu Ile
130 135 140

Trp Phe Ile Glu Gly Arg Lys Ile His Ser Ala Ala Asn Phe Ser Lys
145 150 155 160

Val Lys Arg Ile Asn Leu Val Ile Asp Phe Ala Pro Asp Ile Pro Phe
165 170 175

```
Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 49
<211> LENGTH: 831
<212> TYPE: DNA
<213> ORGANISM: Artificial Sequence
<220> FEATURE:
<223> OTHER INFORMATION: gene sequence of I39R mutant

<400> SEQUENCE: 49

```
atggaatcca agatcatcgg taaagtcaac ttcgaggagc atctgctgga taaagagctg      60

aaactgatcg acactttcga gttcaacgac agctacagcg aatacgcttc tggtcgttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831
```

<210> SEQ ID NO 50
<211> LENGTH: 276
<212> TYPE: PRT
<213> ORGANISM: Artificial Sequence
<220> FEATURE:
<223> OTHER INFORMATION: amino acid sequence of I39R mutant

<400> SEQUENCE: 50

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Arg Trp Lys Thr Cys Met Leu Trp Asn Arg
        35                  40                  45

Ser Gly Gln Lys Asp Asp His Leu Ser Ile Glu His Asp Thr Tyr Val
```

```
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 51
<211> LENGTH: 831
<212> TYPE: DNA
<213> ORGANISM: Artificial Sequence
<220> FEATURE:
<223> OTHER INFORMATION: gene sequence of W40F mutant

<400> SEQUENCE: 51

```
atggaatcca agatcatcgg taaagtcaac ttcgaggagc atctgctgga taaagagctg      60

aaactgatcg acactttcga gttcaacgac agctacagcg aatacgcttc tggtattttt     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780
```

```
gcgcaggaag taaccgatct gctgattcgc aaaggcccga ttaataacta a            831


<210> SEQ ID NO 52
<211> LENGTH: 276
<212> TYPE: PRT
<213> ORGANISM: Artificial Sequence
<220> FEATURE:
<223> OTHER INFORMATION: amino acid sequence of W40F mutant

<400> SEQUENCE: 52

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Phe Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 53
<211> LENGTH: 831
<212> TYPE: DNA
<213> ORGANISM: Artificial Sequence
<220> FEATURE:
<223> OTHER INFORMATION: gene sequence of K41E mutant

<400> SEQUENCE: 53

atggaatcca agatcatcgg taaagtcaac ttcgaggagc atctgctgga taaagagctg      60
```

-continued

```
aaactgatcg acactttcga gttcaacgac agctacagcg aatacgcttc tggtatttgg    120

gaaacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

```
<210> SEQ ID NO 54
<211> LENGTH: 276
<212> TYPE: PRT
<213> ORGANISM: Artificial Sequence
<220> FEATURE:
<223> OTHER INFORMATION: amino acid sequence of K41E mutant

<400> SEQUENCE: 54

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Glu Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
```

-continued

```
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 55
<211> LENGTH: 831
<212> TYPE: DNA
<213> ORGANISM: Artificial Sequence
<220> FEATURE:
<223> OTHER INFORMATION: gene sequence of D54G mutant

<400> SEQUENCE: 55

atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg gtcatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 56
<211> LENGTH: 276
<212> TYPE: PRT
<213> ORGANISM: Artificial Sequence
<220> FEATURE:
<223> OTHER INFORMATION: amino acid sequence of D54G mutant

<400> SEQUENCE: 56

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Gly His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110
```

```
Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 57
<211> LENGTH: 831
<212> TYPE: DNA
<213> ORGANISM: Artificial Sequence
<220> FEATURE:
<223> OTHER INFORMATION: gene sequence of H55Q mutant

<400> SEQUENCE: 57

```
atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg accagctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831
```

<210> SEQ ID NO 58
<211> LENGTH: 276
<212> TYPE: PRT
<213> ORGANISM: Artificial Sequence
<220> FEATURE:
<223> OTHER INFORMATION: amino acid sequence of H55Q mutant

<400> SEQUENCE: 58

Met Glu Ser Lys Ile Ile Gly Lys Val Asn Phe Glu Glu His Leu Leu
1 5 10 15

Asp Lys Glu Leu Lys Leu Ile Asp Thr Phe Glu Phe Asn Asp Ser Tyr
20 25 30

Ser Glu Tyr Ala Ser Gly Ile Trp Lys Thr Cys Met Leu Trp Asn Arg
35 40 45

Ser Gly Gln Lys Asp Asp Gln Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys
100 105 110

Lys Gly Phe Thr Arg Ile His Ile Pro Leu Lys Ile Asn Glu His Ala
115 120 125

Leu Thr Ser Glu Glu Asp Val Val Tyr Asn Met Gln Lys Gly Glu Ile
130 135 140

Trp Phe Ile Glu Gly Arg Lys Ile His Ser Ala Ala Asn Phe Ser Lys
145 150 155 160

Val Lys Arg Ile Asn Leu Val Ile Asp Phe Ala Pro Asp Ile Pro Phe
165 170 175

Glu Glu Leu Phe Leu Asn Ser Glu Asn Tyr Gln Pro Asn Leu Ile Pro
180 185 190

Lys Ile Ser Gln Arg Thr Gln Leu Lys Glu Glu Glu Leu Gly Tyr Ile
195 200 205

Lys Gly Leu Ser Lys Ile Ile Asn Glu Met Asn Phe Asp Asp Ile Leu
210 215 220

Ser Ile Leu Ser Lys Ile His Phe Tyr Arg Asn Val Ser Ser Glu Leu
225 230 235 240

Val Phe Gly Trp Leu Asp Glu Ile Ala Thr Ala Ser Asn Asn Tyr Asn
245 250 255

Ile Gln Arg Lys Ala Gln Glu Val Thr Asp Leu Leu Ile Arg Lys Gly
260 265 270

Pro Ile Asn Asn
275

<210> SEQ ID NO 59
<211> LENGTH: 831
<212> TYPE: DNA
<213> ORGANISM: Artificial Sequence
<220> FEATURE:
<223> OTHER INFORMATION: gene sequence of S57L mutant

<400> SEQUENCE: 59
atggaatcca agatcatcgg taaagtcaac ttcgaggagc atctgctgga taaagagctg 60
aaactgatcg acactttcga gttcaacgac agctacagcg aatacgcttc tggtatttgg 120
aagacttgca tgctgtggaa ccgttctggt cagaaagatg accatctgct gattgaacat 180
gatacctacg tgaaacctac tgaatacggc aaacagctgg catacgtaaa cgaaatcatc 240
gctaacacct ttaagaaaga acacatcaag acggtgcgtc tgttcatgtg tatcaacggc 300
ctgatcatcc cacacaaaga ctacctggaa ttcaagaaag gcttcacccg tatccacatc 360

-continued

```
ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831


<210> SEQ ID NO 60
<211> LENGTH: 276
<212> TYPE: PRT
<213> ORGANISM: Artificial Sequence
<220> FEATURE:
<223> OTHER INFORMATION: amino acid sequence of S57L mutant

<400> SEQUENCE: 60

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Leu Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 61
<211> LENGTH: 831
<212> TYPE: DNA
<213> ORGANISM: Artificial Sequence
<220> FEATURE:
<223> OTHER INFORMATION: gene sequence of I58T mutant

<400> SEQUENCE: 61

```
atggaatcca agatcatcgg taaagtcaac ttcgaggagc atctgctgga taaagagctg     60

aaactgatcg acactttcga gttcaacgac agctacagcg aatacgcttc tggtatttgg    120

aagacttgca tgctgtggaa ccgttctggt cagaaagatg accatctgtc taccgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 62
<211> LENGTH: 276
<212> TYPE: PRT
<213> ORGANISM: Artificial Sequence
<220> FEATURE:
<223> OTHER INFORMATION: amino acid sequence of I58T mutant

<400> SEQUENCE: 62

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Thr Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160
```

```
Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 63
<211> LENGTH: 831
<212> TYPE: DNA
<213> ORGANISM: Artificial Sequence
<220> FEATURE:
<223> OTHER INFORMATION: gene sequence of I58Y mutant

<400> SEQUENCE: 63

atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg accatctgtc ttatgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 64
<211> LENGTH: 276
<212> TYPE: PRT
<213> ORGANISM: Artificial Sequence
<220> FEATURE:
<223> OTHER INFORMATION: amino acid sequence of I58Y mutant

<400> SEQUENCE: 64

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
```

-continued

```
        35                  40                  45

Ser Gly Gln Lys Asp Asp His Leu Ser Tyr Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 65
<211> LENGTH: 831
<212> TYPE: DNA
<213> ORGANISM: Artificial Sequence
<220> FEATURE:
<223> OTHER INFORMATION: gene sequence of I58A mutant

<400> SEQUENCE: 65

atggaatcca agatcatcgg taaagtcaac ttcgaggagc atctgctgga taaagagctg     60

aaactgatcg acactttcga gttcaacgac agctacagcg aatacgcttc tggtatttgg    120

aagacttgca tgctgtggaa ccgttctggt cagaaagatg accatctgtc tgcagaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660
```

gacgacatcc tgtccattct gagcaaaatt cacttctatc gcaacgtttc ctccgaactg 720
gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 66
<211> LENGTH: 276
<212> TYPE: PRT
<213> ORGANISM: Artificial Sequence
<220> FEATURE:
<223> OTHER INFORMATION: amino acid sequence of I58A mutant

<400> SEQUENCE: 66

Met Glu Ser Lys Ile Ile Gly Lys Val Asn Phe Glu Glu His Leu Leu
1 5 10 15

Asp Lys Glu Leu Lys Leu Ile Asp Thr Phe Glu Phe Asn Asp Ser Tyr
20 25 30

Ser Glu Tyr Ala Ser Gly Ile Trp Lys Thr Cys Met Leu Trp Asn Arg
35 40 45

Ser Gly Gln Lys Asp Asp His Leu Ser Ala Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys
100 105 110

Lys Gly Phe Thr Arg Ile His Ile Pro Leu Lys Ile Asn Glu His Ala
115 120 125

Leu Thr Ser Glu Glu Asp Val Val Tyr Asn Met Gln Lys Gly Glu Ile
130 135 140

Trp Phe Ile Glu Gly Arg Lys Ile His Ser Ala Ala Asn Phe Ser Lys
145 150 155 160

Val Lys Arg Ile Asn Leu Val Ile Asp Phe Ala Pro Asp Ile Pro Phe
165 170 175

Glu Glu Leu Phe Leu Asn Ser Glu Asn Tyr Gln Pro Asn Leu Ile Pro
180 185 190

Lys Ile Ser Gln Arg Thr Gln Leu Lys Glu Glu Glu Leu Gly Tyr Ile
195 200 205

Lys Gly Leu Ser Lys Ile Ile Asn Glu Met Asn Phe Asp Asp Ile Leu
210 215 220

Ser Ile Leu Ser Lys Ile His Phe Tyr Arg Asn Val Ser Ser Glu Leu
225 230 235 240

Val Phe Gly Trp Leu Asp Glu Ile Ala Thr Ala Ser Asn Asn Tyr Asn
245 250 255

Ile Gln Arg Lys Ala Gln Glu Val Thr Asp Leu Leu Ile Arg Lys Gly
260 265 270

Pro Ile Asn Asn
275

<210> SEQ ID NO 67
<211> LENGTH: 831
<212> TYPE: DNA
<213> ORGANISM: Artificial Sequence
<220> FEATURE:
<223> OTHER INFORMATION: gene sequence of I58R mutant

<400> SEQUENCE: 67

```
atggaatcca agatcatcgg taaagtcaac ttcgaggagc atctgctgga taaagagctg     60

aaactgatcg acactttcga gttcaacgac agctacagcg aatacgcttc tggtatttgg    120

aagacttgca tgctgtggaa ccgttctggt cagaaagatg accatctgtc tcgtgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831


<210> SEQ ID NO 68
<211> LENGTH: 276
<212> TYPE: PRT
<213> ORGANISM: Artificial Sequence
<220> FEATURE:
<223> OTHER INFORMATION: amino acid sequence of I58R mutant

<400> SEQUENCE: 68

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Arg Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
```

```
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 69
<211> LENGTH: 831
<212> TYPE: DNA
<213> ORGANISM: Artificial Sequence
<220> FEATURE:
<223> OTHER INFORMATION: gene sequence of I58V mutant

<400> SEQUENCE: 69

atggaatcca agatcatcgg taaagtcaac ttcgaggagc atctgctgga taaagagctg     60

aaactgatcg acactttcga gttcaacgac agctacagcg aatacgcttc tggtatttgg    120

aagacttgca tgctgtggaa ccgttctggt cagaaagatg accatctgtc tgttgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831


<210> SEQ ID NO 70
<211> LENGTH: 276
<212> TYPE: PRT
<213> ORGANISM: Artificial Sequence
<220> FEATURE:
<223> OTHER INFORMATION: amino acid sequence of I58V mutant

<400> SEQUENCE: 70

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Val Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95
```

```
Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 71
<211> LENGTH: 831
<212> TYPE: DNA
<213> ORGANISM: Artificial Sequence
<220> FEATURE:
<223> OTHER INFORMATION: gene sequence of I58S mutant

<400> SEQUENCE: 71

```
atggaatcca agatcatcgg taaagtcaac ttcgaggagc atctgctgga taaagagctg     60

aaactgatcg acactttcga gttcaacgac agctacagcg aatacgcttc tggtatttgg    120

aagacttgca tgctgtggaa ccgttctggt cagaaagatg accatctgtc tagcgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 72
<211> LENGTH: 276
<212> TYPE: PRT

-continued

<213> ORGANISM: Artificial Sequence
<220> FEATURE:
<223> OTHER INFORMATION: amino acid sequence of I58S mutant

<400> SEQUENCE: 72

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ser Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 73
<211> LENGTH: 831
<212> TYPE: DNA
<213> ORGANISM: Artificial Sequence
<220> FEATURE:
<223> OTHER INFORMATION: gene sequence of I58C mutant

<400> SEQUENCE: 73

```
atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg accatctgtc ttgtgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300
```

```
ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 74
<211> LENGTH: 276
<212> TYPE: PRT
<213> ORGANISM: Artificial Sequence
<220> FEATURE:
<223> OTHER INFORMATION: amino acid sequence of I58C mutant

<400> SEQUENCE: 74

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Cys Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270
```

Pro Ile Asn Asn
275

<210> SEQ ID NO 75
<211> LENGTH: 831
<212> TYPE: DNA
<213> ORGANISM: Artificial Sequence
<220> FEATURE:
<223> OTHER INFORMATION: gene sequence of K86P mutant

<400> SEQUENCE: 75
atggaatcca agatcatcgg taaagtcaac ttcgaggagc atctgctgga taaagagctg 60
aaactgatcg acactttcga gttcaacgac agctacagcg aatacgcttc tggtatttgg 120
aagacttgca tgctgtggaa ccgttctggt cagaaagatg accatctgtc tattgaacat 180
gatacctacg tgaaacctac tgaatacggc aaacagctgg catacgtaaa cgaaatcatc 240
gctaacacct ttaagccgga acacatcaag acggtgcgtc tgttcatgtg tatcaacggc 300
ctgatcatcc cacacaaaga ctacctggaa ttcaagaaag gcttcacccg tatccacatc 360
ccgctgaaaa tcaacgaaca cgcactgacc tctgaagaag atgttgttta caacatgcag 420
aaaggtgaaa tttggttcat cgaaggccgt aaaatccaca gcgctgccaa tttcagcaaa 480
gtgaaacgta tcaacctggt catcgacttc gcgccggata ttccgtttga agaactgttc 540
ctgaattctg agaactatca accgaacctg atcccgaaaa tctctcaacg tacccagctg 600
aaagaagaag agctgggtta tatcaaaggt ctgtctaaaa ttatcaatga aatgaacttt 660
gacgacatcc tgtccattct gagcaaaatt cacttctatc gcaacgtttc ctccgaactg 720
gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 76
<211> LENGTH: 276
<212> TYPE: PRT
<213> ORGANISM: Artificial Sequence
<220> FEATURE:
<223> OTHER INFORMATION: amino acid sequence of K86P mutant

<400> SEQUENCE: 76

Met Glu Ser Lys Ile Ile Gly Lys Val Asn Phe Glu Glu His Leu Leu
1 5 10 15

Asp Lys Glu Leu Lys Leu Ile Asp Thr Phe Glu Phe Asn Asp Ser Tyr
20 25 30

Ser Glu Tyr Ala Ser Gly Ile Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Pro Glu His Ile Lys Thr Val Arg Leu Phe Met
85 90 95

Cys Ile Asn Gly Leu Ile Ile Pro His Lys Asp Tyr Leu Glu Phe Lys
100 105 110

Lys Gly Phe Thr Arg Ile His Ile Pro Leu Lys Ile Asn Glu His Ala
115 120 125

Leu Thr Ser Glu Glu Asp Val Val Tyr Asn Met Gln Lys Gly Glu Ile
130 135 140

```
Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 77
<211> LENGTH: 831
<212> TYPE: DNA
<213> ORGANISM: Artificial Sequence
<220> FEATURE:
<223> OTHER INFORMATION: gene sequence of T91A mutant

<400> SEQUENCE: 77

atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag gcagtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 78
<211> LENGTH: 276
<212> TYPE: PRT
<213> ORGANISM: Artificial Sequence
<220> FEATURE:
<223> OTHER INFORMATION: amino acid sequence of T91A mutant

<400> SEQUENCE: 78

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
```

```
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Ala Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 79
<211> LENGTH: 831
<212> TYPE: DNA
<213> ORGANISM: Artificial Sequence
<220> FEATURE:
<223> OTHER INFORMATION: gene sequence of F95Y mutant

<400> SEQUENCE: 79

atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgtatatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600
```

```
aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 80
<211> LENGTH: 276
<212> TYPE: PRT
<213> ORGANISM: Artificial Sequence
<220> FEATURE:
<223> OTHER INFORMATION: amino acid sequence of F95Y mutant

<400> SEQUENCE: 80

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Tyr Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 81
<211> LENGTH: 831
<212> TYPE: DNA
<213> ORGANISM: Artificial Sequence
<220> FEATURE:

<223> OTHER INFORMATION: gene sequence of C97Y mutant

<400> SEQUENCE: 81

```
atggaatcca agatcatcgg taaagtcaac ttcgaggagc atctgctgga taaagagctg     60
aaactgatcg acactttcga gttcaacgac agctacagcg aatacgcttc tggtatttgg    120
aagacttgca tgctgtggaa ccgttctggt cagaaagatg accatctgtc tattgaacat    180
gatacctacg tgaaacctac tgaatacggc aaacagctgg catacgtaaa cgaaatcatc    240
gctaacacct ttaagaaaga acacatcaag acggtgcgtc tgttcatgta tatcaacggc    300
ctgatcatcc cacacaaaga ctacctggaa ttcaagaaag gcttcacccg tatccacatc    360
ccgctgaaaa tcaacgaaca cgcactgacc tctgaagaag atgttgttta caacatgcag    420
aaaggtgaaa tttggttcat cgaaggccgt aaaatccaca gcgctgccaa tttcagcaaa    480
gtgaaacgta tcaacctggt catcgacttc gcgccggata ttccgtttga agaactgttc    540
ctgaattctg agaactatca accgaacctg atcccgaaaa tctctcaacg tacccagctg    600
aaagaagaag agctgggtta tatcaaaggt ctgtctaaaa ttatcaatga aatgaacttt    660
gacgacatcc tgtccattct gagcaaaatt cacttctatc gcaacgtttc ctccgaactg    720
gtttttggct ggctggacga aattgccacg gcgtccaaca actataacat tcagcgcaaa    780
gcgcaggaag taaccgatct gctgattcgc aaaggcccga ttaataacta a             831
```

<210> SEQ ID NO 82
<211> LENGTH: 276
<212> TYPE: PRT
<213> ORGANISM: Artificial Sequence
<220> FEATURE:
<223> OTHER INFORMATION: amino acid sequence of C97Y mutant

<400> SEQUENCE: 82

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Tyr Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
```

```
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 83
<211> LENGTH: 831
<212> TYPE: DNA
<213> ORGANISM: Artificial Sequence
<220> FEATURE:
<223> OTHER INFORMATION: gene sequence of I98V mutant

<400> SEQUENCE: 83

```
atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tgttaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831
```

<210> SEQ ID NO 84
<211> LENGTH: 276
<212> TYPE: PRT
<213> ORGANISM: Artificial Sequence
<220> FEATURE:
<223> OTHER INFORMATION: amino acid sequence of I98V mutant

<400> SEQUENCE: 84

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80
```

```
Ala Asn Thr Phe Lys Lys Glu His Ile Lys Thr Val Arg Leu Phe Met
                85                  90                  95

Cys Val Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 85
<211> LENGTH: 831
<212> TYPE: DNA
<213> ORGANISM: Artificial Sequence
<220> FEATURE:
<223> OTHER INFORMATION: gene sequence of K106V mutant

<400> SEQUENCE: 85

```
atggaatcca agatcatcgg taaagtcaac ttcgaggagc atctgctgga taaagagctg     60

aaactgatcg acactttcga gttcaacgac agctacagcg aatacgcttc tggtatttgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacgttga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

```
<210> SEQ ID NO 86
<211> LENGTH: 276
<212> TYPE: PRT
<213> ORGANISM: Artificial Sequence
<220> FEATURE:
<223> OTHER INFORMATION: amino acid sequence of K106V mutant

<400> SEQUENCE: 86

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Val Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 87
<211> LENGTH: 831
<212> TYPE: DNA
<213> ORGANISM: Artificial Sequence
<220> FEATURE:
<223> OTHER INFORMATION: gene sequence of K106T mutant

<400> SEQUENCE: 87

atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg accatctgtc tattgaacat     180
```

-continued gatacctacg tgaaacctac tgaatacggc aaacagctgg catacgtaaa cgaaatcatc 240
gctaacacct ttaagaaaga acacatcaag acggtgcgtc tgttcatgtg tatcaacggc 300
ctgatcatcc cacacaccga ctacctggaa ttcaagaaag gcttcacccg tatccacatc 360
ccgctgaaaa tcaacgaaca cgcactgacc tctgaagaag atgttgttta caacatgcag 420
aaaggtgaaa tttggttcat cgaaggccgt aaaatccaca gcgctgccaa tttcagcaaa 480
gtgaaacgta tcaacctggt catcgacttc gcgccggata ttccgtttga agaactgttc 540
ctgaattctg agaactatca accgaacctg atcccgaaaa tctctcaacg tacccagctg 600
aaagaagaag agctgggtta tatcaaaggt ctgtctaaaa ttatcaatga aatgaacttt 660
gacgacatcc tgtccattct gagcaaaatt cacttctatc gcaacgtttc ctccgaactg 720
gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 88
<211> LENGTH: 276
<212> TYPE: PRT
<213> ORGANISM: Artificial Sequence
<220> FEATURE:
<223> OTHER INFORMATION: amino acid sequence of K106T mutant

<400> SEQUENCE: 88

Met Glu Ser Lys Ile Ile Gly Lys Val Asn Phe Glu Glu His Leu Leu
1 5 10 15

Asp Lys Glu Leu Lys Leu Ile Asp Thr Phe Glu Phe Asn Asp Ser Tyr
20 25 30

Ser Glu Tyr Ala Ser Gly Ile Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Thr Asp Tyr Leu Glu Phe Lys
100 105 110

Lys Gly Phe Thr Arg Ile His Ile Pro Leu Lys Ile Asn Glu His Ala
115 120 125

Leu Thr Ser Glu Glu Asp Val Val Tyr Asn Met Gln Lys Gly Glu Ile
130 135 140

Trp Phe Ile Glu Gly Arg Lys Ile His Ser Ala Ala Asn Phe Ser Lys
145 150 155 160

Val Lys Arg Ile Asn Leu Val Ile Asp Phe Ala Pro Asp Ile Pro Phe
165 170 175

Glu Glu Leu Phe Leu Asn Ser Glu Asn Tyr Gln Pro Asn Leu Ile Pro
180 185 190

Lys Ile Ser Gln Arg Thr Gln Leu Lys Glu Glu Glu Leu Gly Tyr Ile
195 200 205

Lys Gly Leu Ser Lys Ile Ile Asn Glu Met Asn Phe Asp Asp Ile Leu
210 215 220

Ser Ile Leu Ser Lys Ile His Phe Tyr Arg Asn Val Ser Ser Glu Leu
225 230 235 240

Val Phe Gly Trp Leu Asp Glu Ile Ala Thr Ala Ser Asn Asn Tyr Asn
245 250 255

```
Ile Gln Arg Lys Ala Gln Glu Val Thr Asp Leu Leu Ile Arg Lys Gly
            260                 265                 270

Pro Ile Asn Asn
        275


<210> SEQ ID NO 89
<211> LENGTH: 831
<212> TYPE: DNA
<213> ORGANISM: Artificial Sequence
<220> FEATURE:
<223> OTHER INFORMATION: gene sequence of K106Q mutant

<400> SEQUENCE: 89

atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacaccagga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 90
<211> LENGTH: 276
<212> TYPE: PRT
<213> ORGANISM: Artificial Sequence
<220> FEATURE:
<223> OTHER INFORMATION: amino acid sequence of K106Q mutant

<400> SEQUENCE: 90

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Gln Asp Tyr Leu Glu Phe Lys
            100                 105                 110

Lys Gly Phe Thr Arg Ile His Ile Pro Leu Lys Ile Asn Glu His Ala
        115                 120                 125
```

```
Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 91
<211> LENGTH: 831
<212> TYPE: DNA
<213> ORGANISM: Artificial Sequence
<220> FEATURE:
<223> OTHER INFORMATION: gene sequence of F111S mutant

<400> SEQUENCE: 91

atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa agcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 92
<211> LENGTH: 276
<212> TYPE: PRT
<213> ORGANISM: Artificial Sequence
<220> FEATURE:
<223> OTHER INFORMATION: amino acid sequence of F111S mutant

<400> SEQUENCE: 92

Met Glu Ser Lys Ile Ile Gly Lys Val Asn Phe Glu Glu His Leu Leu
```

-continued

```
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Ser Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 93
<211> LENGTH: 831
<212> TYPE: DNA
<213> ORGANISM: Artificial Sequence
<220> FEATURE:
<223> OTHER INFORMATION: gene sequence of K112E mutant

<400> SEQUENCE: 93

```
atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcgaaaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480
```

-continued

```
gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 94
<211> LENGTH: 276
<212> TYPE: PRT
<213> ORGANISM: Artificial Sequence
<220> FEATURE:
<223> OTHER INFORMATION: amino acid sequence of K112E mutant

<400> SEQUENCE: 94

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Glu
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 95
<211> LENGTH: 831

<212> TYPE: DNA
<213> ORGANISM: Artificial Sequence
<220> FEATURE:
<223> OTHER INFORMATION: gene sequence of I118F mutant

<400> SEQUENCE: 95
atggaatcca agatcatcgg taaagtcaac ttcgaggagc atctgctgga taaagagctg 60
aaactgatcg acactttcga gttcaacgac agctacagcg aatacgcttc tggtatttgg 120
aagacttgca tgctgtggaa ccgttctggt cagaaagatg accatctgtc tattgaacat 180
gatacctacg tgaaacctac tgaatacggc aaacagctgg catacgtaaa cgaaatcatc 240
gctaacacct ttaagaaaga acacatcaag acggtgcgtc tgttcatgtg tatcaacggc 300
ctgatcatcc cacacaaaga ctacctggaa ttcaagaaag gcttcacccg ttttcacatc 360
ccgctgaaaa tcaacgaaca cgcactgacc tctgaagaag atgttgttta caacatgcag 420
aaaggtgaaa tttggttcat cgaaggccgt aaaatccaca gcgctgccaa tttcagcaaa 480
gtgaaacgta tcaacctggt catcgacttc gcgccggata ttccgtttga agaactgttc 540
ctgaattctg agaactatca accgaacctg atcccgaaaa tctctcaacg tacccagctg 600
aaagaagaag agctgggtta tatcaaaggt ctgtctaaaa ttatcaatga aatgaacttt 660
gacgacatcc tgtccattct gagcaaaatt cacttctatc gcaacgtttc ctccgaactg 720
gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 96
<211> LENGTH: 276
<212> TYPE: PRT
<213> ORGANISM: Artificial Sequence
<220> FEATURE:
<223> OTHER INFORMATION: amino acid sequence of I118F mutant

<400> SEQUENCE: 96

Met Glu Ser Lys Ile Ile Gly Lys Val Asn Phe Glu Glu His Leu Leu
1 5 10 15

Asp Lys Glu Leu Lys Leu Ile Asp Thr Phe Glu Phe Asn Asp Ser Tyr
20 25 30

Ser Glu Tyr Ala Ser Gly Ile Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys
100 105 110

Lys Gly Phe Thr Arg Phe His Ile Pro Leu Lys Ile Asn Glu His Ala
115 120 125

Leu Thr Ser Glu Glu Asp Val Val Tyr Asn Met Gln Lys Gly Glu Ile
130 135 140

Trp Phe Ile Glu Gly Arg Lys Ile His Ser Ala Ala Asn Phe Ser Lys
145 150 155 160

Val Lys Arg Ile Asn Leu Val Ile Asp Phe Ala Pro Asp Ile Pro Phe
165 170 175

Glu Glu Leu Phe Leu Asn Ser Glu Asn Tyr Gln Pro Asn Leu Ile Pro

```
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 97
<211> LENGTH: 831
<212> TYPE: DNA
<213> ORGANISM: Artificial Sequence
<220> FEATURE:
<223> OTHER INFORMATION: gene sequence of H119R mutant

<400> SEQUENCE: 97

atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccgtatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 98
<211> LENGTH: 276
<212> TYPE: PRT
<213> ORGANISM: Artificial Sequence
<220> FEATURE:
<223> OTHER INFORMATION: amino acid sequence of H119R mutant

<400> SEQUENCE: 98

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60
```

-continued

```
Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile Arg Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 99
<211> LENGTH: 831
<212> TYPE: DNA
<213> ORGANISM: Artificial Sequence
<220> FEATURE:
<223> OTHER INFORMATION: gene sequence of H119F mutant

<400> SEQUENCE: 99

```
atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatctttatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780
```

gcgcaggaag taaccgatct gctgattcgc aaaggcccga ttaataacta a 831

<210> SEQ ID NO 100
<211> LENGTH: 276
<212> TYPE: PRT
<213> ORGANISM: Artificial Sequence
<220> FEATURE:
<223> OTHER INFORMATION: amino acid sequence of H119F mutant

<400> SEQUENCE: 100

Met Glu Ser Lys Ile Ile Gly Lys Val Asn Phe Glu Glu His Leu Leu
1 5 10 15

Asp Lys Glu Leu Lys Leu Ile Asp Thr Phe Glu Phe Asn Asp Ser Tyr
20 25 30

Ser Glu Tyr Ala Ser Gly Ile Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys
100 105 110

Lys Gly Phe Thr Arg Ile Phe Ile Pro Leu Lys Ile Asn Glu His Ala
115 120 125

Leu Thr Ser Glu Glu Asp Val Val Tyr Asn Met Gln Lys Gly Glu Ile
130 135 140

Trp Phe Ile Glu Gly Arg Lys Ile His Ser Ala Ala Asn Phe Ser Lys
145 150 155 160

Val Lys Arg Ile Asn Leu Val Ile Asp Phe Ala Pro Asp Ile Pro Phe
165 170 175

Glu Glu Leu Phe Leu Asn Ser Glu Asn Tyr Gln Pro Asn Leu Ile Pro
180 185 190

Lys Ile Ser Gln Arg Thr Gln Leu Lys Glu Glu Glu Leu Gly Tyr Ile
195 200 205

Lys Gly Leu Ser Lys Ile Ile Asn Glu Met Asn Phe Asp Asp Ile Leu
210 215 220

Ser Ile Leu Ser Lys Ile His Phe Tyr Arg Asn Val Ser Ser Glu Leu
225 230 235 240

Val Phe Gly Trp Leu Asp Glu Ile Ala Thr Ala Ser Asn Asn Tyr Asn
245 250 255

Ile Gln Arg Lys Ala Gln Glu Val Thr Asp Leu Leu Ile Arg Lys Gly
260 265 270

Pro Ile Asn Asn
275

<210> SEQ ID NO 101
<211> LENGTH: 831
<212> TYPE: DNA
<213> ORGANISM: Artificial Sequence
<220> FEATURE:
<223> OTHER INFORMATION: gene sequence of I120V mutant

<400> SEQUENCE: 101
atggaatcca agatcatcgg taaagtcaac ttcgaggagc atctgctgga taaagagctg 60
aaactgatcg acactttcga gttcaacgac agctacagcg aatacgcttc tggtatttgg 120

```
aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacgtt    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 102
<211> LENGTH: 276
<212> TYPE: PRT
<213> ORGANISM: Artificial Sequence
<220> FEATURE:
<223> OTHER INFORMATION: amino acid sequence of I120V mutant

<400> SEQUENCE: 102

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Val Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240
```

Val Phe Gly Trp Leu Asp Glu Ile Ala Thr Ala Ser Asn Asn Tyr Asn
245 250 255

Ile Gln Arg Lys Ala Gln Glu Val Thr Asp Leu Leu Ile Arg Lys Gly
260 265 270

Pro Ile Asn Asn
275

<210> SEQ ID NO 103
<211> LENGTH: 831
<212> TYPE: DNA
<213> ORGANISM: Artificial Sequence
<220> FEATURE:
<223> OTHER INFORMATION: gene sequence of K123D mutant

<400> SEQUENCE: 103
atggaatcca agatcatcgg taaagtcaac ttcgaggagc atctgctgga taaagagctg 60
aaactgatcg acactttcga gttcaacgac agctacagcg aatacgcttc tggtatttgg 120
aagacttgca tgctgtggaa ccgttctggt cagaaagatg accatctgtc tattgaacat 180
gatacctacg tgaaacctac tgaatacggc aaacagctgg catacgtaaa cgaaatcatc 240
gctaacacct ttaagaaaga acacatcaag acggtgcgtc tgttcatgtg tatcaacggc 300
ctgatcatcc cacacaaaga ctacctggaa ttcaagaaag gcttcacccg tatccacatc 360
ccgctggata tcaacgaaca cgcactgacc tctgaagaag atgttgttta caacatgcag 420
aaaggtgaaa tttggttcat cgaaggccgt aaaatccaca gcgctgccaa tttcagcaaa 480
gtgaaacgta tcaacctggt catcgacttc gcgccggata ttccgtttga agaactgttc 540
ctgaattctg agaactatca accgaacctg atcccgaaaa tctctcaacg tacccagctg 600
aaagaagaag agctgggtta tatcaaaggt ctgtctaaaa ttatcaatga aatgaacttt 660
gacgacatcc tgtccattct gagcaaaatt cacttctatc gcaacgtttc ctccgaactg 720
gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 104
<211> LENGTH: 276
<212> TYPE: PRT
<213> ORGANISM: Artificial Sequence
<220> FEATURE:
<223> OTHER INFORMATION: amino acid sequence of K123D mutant

<400> SEQUENCE: 104

Met Glu Ser Lys Ile Ile Gly Lys Val Asn Phe Glu Glu His Leu Leu
1 5 10 15

Asp Lys Glu Leu Lys Leu Ile Asp Thr Phe Glu Phe Asn Asp Ser Tyr
20 25 30

Ser Glu Tyr Ala Ser Gly Ile Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys
100 105 110

-continued

```
Lys Gly Phe Thr Arg Ile His Ile Pro Leu Asp Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 105
<211> LENGTH: 831
<212> TYPE: DNA
<213> ORGANISM: Artificial Sequence
<220> FEATURE:
<223> OTHER INFORMATION: gene sequence of K123N mutant

<400> SEQUENCE: 105

```
atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaata tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831
```

<210> SEQ ID NO 106
<211> LENGTH: 276
<212> TYPE: PRT
<213> ORGANISM: Artificial Sequence
<220> FEATURE:
<223> OTHER INFORMATION: amino acid sequence of K123N mutant

<400> SEQUENCE: 106

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Asn Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275

<210> SEQ ID NO 107
<211> LENGTH: 831
<212> TYPE: DNA
<213> ORGANISM: Artificial Sequence
<220> FEATURE:
<223> OTHER INFORMATION: gene sequence of K123Q mutant

<400> SEQUENCE: 107
atggaatcca agatcatcgg taaagtcaac ttcgaggagc atctgctgga taaagagctg 60
aaactgatcg acactttcga gttcaacgac agctacagcg aatacgcttc tggtatttgg 120
aagacttgca tgctgtggaa ccgttctggt cagaaagatg accatctgtc tattgaacat 180
gatacctacg tgaaacctac tgaatacggc aaacagctgg catacgtaaa cgaaatcatc 240
gctaacacct ttaagaaaga acacatcaag acggtgcgtc tgttcatgtg tatcaacggc 300
ctgatcatcc cacacaaaga ctacctggaa ttcaagaaag gcttcacccg tatccacatc 360
ccgctgcaga tcaacgaaca cgcactgacc tctgaagaag atgttgttta caacatgcag 420

```
aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

```
<210> SEQ ID NO 108
<211> LENGTH: 276
<212> TYPE: PRT
<213> ORGANISM: Artificial Sequence
<220> FEATURE:
<223> OTHER INFORMATION: amino acid sequence of K123Q mutant

<400> SEQUENCE: 108

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Gln Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 109
<211> LENGTH: 831
<212> TYPE: DNA
<213> ORGANISM: Artificial Sequence
<220> FEATURE:
<223> OTHER INFORMATION: gene sequence of K123S mutant

<400> SEQUENCE: 109
atggaatcca agatcatcgg taaagtcaac ttcgaggagc atctgctgga taaagagctg 60
aaactgatcg acactttcga gttcaacgac agctacagcg aatacgcttc tggtatttgg 120
aagacttgca tgctgtggaa ccgttctggt cagaaagatg accatctgtc tattgaacat 180
gatacctacg tgaaacctac tgaatacggc aaacagctgg catacgtaaa cgaaatcatc 240
gctaacacct ttaagaaaga acacatcaag acggtgcgtc tgttcatgtg tatcaacggc 300
ctgatcatcc cacacaaaga ctacctggaa ttcaagaaag gcttcacccg tatccacatc 360
ccgctgagca tcaacgaaca cgcactgacc tctgaagaag atgttgttta caacatgcag 420
aaaggtgaaa tttggttcat cgaaggccgt aaaatccaca gcgctgccaa tttcagcaaa 480
gtgaaacgta tcaacctggt catcgacttc gcgccggata ttccgtttga agaactgttc 540
ctgaattctg agaactatca accgaacctg atcccgaaaa tctctcaacg tacccagctg 600
aaagaagaag agctgggtta tatcaaaggt ctgtctaaaa ttatcaatga aatgaacttt 660
gacgacatcc tgtccattct gagcaaaatt cacttctatc gcaacgtttc ctccgaactg 720
gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 110
<211> LENGTH: 276
<212> TYPE: PRT
<213> ORGANISM: Artificial Sequence
<220> FEATURE:
<223> OTHER INFORMATION: amino acid sequence of K123S mutant

<400> SEQUENCE: 110

Met Glu Ser Lys Ile Ile Gly Lys Val Asn Phe Glu Glu His Leu Leu
1 5 10 15

Asp Lys Glu Leu Lys Leu Ile Asp Thr Phe Glu Phe Asn Asp Ser Tyr
20 25 30

Ser Glu Tyr Ala Ser Gly Ile Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys
100 105 110

Lys Gly Phe Thr Arg Ile His Ile Pro Leu Ser Ile Asn Glu His Ala
115 120 125

Leu Thr Ser Glu Glu Asp Val Val Tyr Asn Met Gln Lys Gly Glu Ile
130 135 140

Trp Phe Ile Glu Gly Arg Lys Ile His Ser Ala Ala Asn Phe Ser Lys
145 150 155 160

Val Lys Arg Ile Asn Leu Val Ile Asp Phe Ala Pro Asp Ile Pro Phe

```
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 111
<211> LENGTH: 831
<212> TYPE: DNA
<213> ORGANISM: Artificial Sequence
<220> FEATURE:
<223> OTHER INFORMATION: gene sequence of K123I mutant

<400> SEQUENCE: 111

```
atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgatta tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831
```

<210> SEQ ID NO 112
<211> LENGTH: 276
<212> TYPE: PRT
<213> ORGANISM: Artificial Sequence
<220> FEATURE:
<223> OTHER INFORMATION: amino acid sequence of K123I mutant

<400> SEQUENCE: 112

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45
```

```
Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Ile Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 113
<211> LENGTH: 831
<212> TYPE: DNA
<213> ORGANISM: Artificial Sequence
<220> FEATURE:
<223> OTHER INFORMATION: gene sequence of K123T mutant

<400> SEQUENCE: 113

```
atggaatcca agatcatcgg taaagtcaac ttcgaggagc atctgctgga taaagagctg     60

aaactgatcg acactttcga gttcaacgac agctacagcg aatacgcttc tggtatttgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgacca tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720
```

gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 114
<211> LENGTH: 276
<212> TYPE: PRT
<213> ORGANISM: Artificial Sequence
<220> FEATURE:
<223> OTHER INFORMATION: amino acid sequence of K123T mutant

<400> SEQUENCE: 114

Met Glu Ser Lys Ile Ile Gly Lys Val Asn Phe Glu Glu His Leu Leu
1 5 10 15

Asp Lys Glu Leu Lys Leu Ile Asp Thr Phe Glu Phe Asn Asp Ser Tyr
20 25 30

Ser Glu Tyr Ala Ser Gly Ile Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys
100 105 110

Lys Gly Phe Thr Arg Ile His Ile Pro Leu Thr Ile Asn Glu His Ala
115 120 125

Leu Thr Ser Glu Glu Asp Val Val Tyr Asn Met Gln Lys Gly Glu Ile
130 135 140

Trp Phe Ile Glu Gly Arg Lys Ile His Ser Ala Ala Asn Phe Ser Lys
145 150 155 160

Val Lys Arg Ile Asn Leu Val Ile Asp Phe Ala Pro Asp Ile Pro Phe
165 170 175

Glu Glu Leu Phe Leu Asn Ser Glu Asn Tyr Gln Pro Asn Leu Ile Pro
180 185 190

Lys Ile Ser Gln Arg Thr Gln Leu Lys Glu Glu Glu Leu Gly Tyr Ile
195 200 205

Lys Gly Leu Ser Lys Ile Ile Asn Glu Met Asn Phe Asp Asp Ile Leu
210 215 220

Ser Ile Leu Ser Lys Ile His Phe Tyr Arg Asn Val Ser Ser Glu Leu
225 230 235 240

Val Phe Gly Trp Leu Asp Glu Ile Ala Thr Ala Ser Asn Asn Tyr Asn
245 250 255

Ile Gln Arg Lys Ala Gln Glu Val Thr Asp Leu Leu Ile Arg Lys Gly
260 265 270

Pro Ile Asn Asn
275

<210> SEQ ID NO 115
<211> LENGTH: 831
<212> TYPE: DNA
<213> ORGANISM: Artificial Sequence
<220> FEATURE:
<223> OTHER INFORMATION: gene sequence of T130N mutant

<400> SEQUENCE: 115

-continued

```
atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgaat tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831
```

<210> SEQ ID NO 116
<211> LENGTH: 276
<212> TYPE: PRT
<213> ORGANISM: Artificial Sequence
<220> FEATURE:
<223> OTHER INFORMATION: amino acid sequence of T130N mutant

<400> SEQUENCE: 116

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Asn Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220
```

```
Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 117
<211> LENGTH: 831
<212> TYPE: DNA
<213> ORGANISM: Artificial Sequence
<220> FEATURE:
<223> OTHER INFORMATION: gene sequence of D134G mutant

<400> SEQUENCE: 117

atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag gtgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 118
<211> LENGTH: 276
<212> TYPE: PRT
<213> ORGANISM: Artificial Sequence
<220> FEATURE:
<223> OTHER INFORMATION: amino acid sequence of D134G mutant

<400> SEQUENCE: 118

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95
```

```
Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Gly Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 119
<211> LENGTH: 831
<212> TYPE: DNA
<213> ORGANISM: Artificial Sequence
<220> FEATURE:
<223> OTHER INFORMATION: gene sequence of V135K mutant

<400> SEQUENCE: 119

atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag ataaagttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 120
<211> LENGTH: 276
<212> TYPE: PRT
<213> ORGANISM: Artificial Sequence
```

<220> FEATURE:
<223> OTHER INFORMATION: amino acid sequence of V135K mutant

<400> SEQUENCE: 120

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Lys Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275

<210> SEQ ID NO 121
<211> LENGTH: 831
<212> TYPE: DNA
<213> ORGANISM: Artificial Sequence
<220> FEATURE:
<223> OTHER INFORMATION: gene sequence of N165H mutant

<400> SEQUENCE: 121
atggaatcca agatcatcgg taaagtcaac ttcgaggagc atctgctgga taaagagctg 60
aaactgatcg acactttcga gttcaacgac agctacagcg aatacgcttc tggtatttgg 120
aagacttgca tgctgtggaa ccgttctggt cagaaagatg accatctgtc tattgaacat 180
gatacctacg tgaaacctac tgaatacggc aaacagctgg catacgtaaa cgaaatcatc 240
gctaacacct ttaagaaaga acacatcaag acggtgcgtc tgttcatgtg tatcaacggc 300

-continued

```
ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tccatctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 122
<211> LENGTH: 276
<212> TYPE: PRT
<213> ORGANISM: Artificial Sequence
<220> FEATURE:
<223> OTHER INFORMATION: amino acid sequence of N165H mutant

<400> SEQUENCE: 122

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile His Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270
```

```
Pro Ile Asn Asn
        275


<210> SEQ ID NO 123
<211> LENGTH: 831
<212> TYPE: DNA
<213> ORGANISM: Artificial Sequence
<220> FEATURE:
<223> OTHER INFORMATION: gene sequence of K209R mutant

<400> SEQUENCE: 123

atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatccgtggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 124
<211> LENGTH: 276
<212> TYPE: PRT
<213> ORGANISM: Artificial Sequence
<220> FEATURE:
<223> OTHER INFORMATION: amino acid sequence of K209R mutant

<400> SEQUENCE: 124

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
```

145 150 155 160

Val Lys Arg Ile Asn Leu Val Ile Asp Phe Ala Pro Asp Ile Pro Phe
165 170 175

Glu Glu Leu Phe Leu Asn Ser Glu Asn Tyr Gln Pro Asn Leu Ile Pro
180 185 190

Lys Ile Ser Gln Arg Thr Gln Leu Lys Glu Glu Glu Leu Gly Tyr Ile
195 200 205

Arg Gly Leu Ser Lys Ile Ile Asn Glu Met Asn Phe Asp Asp Ile Leu
210 215 220

Ser Ile Leu Ser Lys Ile His Phe Tyr Arg Asn Val Ser Ser Glu Leu
225 230 235 240

Val Phe Gly Trp Leu Asp Glu Ile Ala Thr Ala Ser Asn Asn Tyr Asn
245 250 255

Ile Gln Arg Lys Ala Gln Glu Val Thr Asp Leu Leu Ile Arg Lys Gly
260 265 270

Pro Ile Asn Asn
275

<210> SEQ ID NO 125
<211> LENGTH: 831
<212> TYPE: DNA
<213> ORGANISM: Artificial Sequence
<220> FEATURE:
<223> OTHER INFORMATION: gene sequence of I223V mutant

<400> SEQUENCE: 125
atggaatcca agatcatcgg taaagtcaac ttcgaggagc atctgctgga taaagagctg 60
aaactgatcg acactttcga gttcaacgac agctacagcg aatacgcttc tggtatttgg 120
aagacttgca tgctgtggaa ccgttctggt cagaaagatg accatctgtc tattgaacat 180
gatacctacg tgaaacctac tgaatacggc aaacagctgg catacgtaaa cgaaatcatc 240
gctaacacct ttaagaaaga acacatcaag acggtgcgtc tgttcatgtg tatcaacggc 300
ctgatcatcc cacacaaaga ctacctggaa ttcaagaaag gcttcacccg tatccacatc 360
ccgctgaaaa tcaacgaaca cgcactgacc tctgaagaag atgttgttta caacatgcag 420
aaaggtgaaa tttggttcat cgaaggccgt aaaatccaca gcgctgccaa tttcagcaaa 480
gtgaaacgta tcaacctggt catcgacttc gcgccggata ttccgtttga agaactgttc 540
ctgaattctg agaactatca accgaacctg atcccgaaaa tctctcaacg tacccagctg 600
aaagaagaag agctgggtta tatcaaaggt ctgtctaaaa ttatcaatga aatgaacttt 660
gacgacgttc tgtccattct gagcaaaatt cacttctatc gcaacgtttc ctccgaactg 720
gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 126
<211> LENGTH: 276
<212> TYPE: PRT
<213> ORGANISM: Artificial Sequence
<220> FEATURE:
<223> OTHER INFORMATION: amino acid sequence of I223V mutant

<400> SEQUENCE: 126

Met Glu Ser Lys Ile Ile Gly Lys Val Asn Phe Glu Glu His Leu Leu
1 5 10 15

Asp Lys Glu Leu Lys Leu Ile Asp Thr Phe Glu Phe Asn Asp Ser Tyr
20 25 30

```
Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 127
<211> LENGTH: 831
<212> TYPE: DNA
<213> ORGANISM: Artificial Sequence
<220> FEATURE:
<223> OTHER INFORMATION: gene sequence of E27K+ K123D mutant

<400> SEQUENCE: 127

```
atggaatcca agatcatcgg taaagtcaac ttcgaggagc atctgctgga taaagagctg      60

aaactgatcg acactttcaa attcaacgac agctacagcg aatacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctggata tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600
```

```
aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 128
<211> LENGTH: 276
<212> TYPE: PRT
<213> ORGANISM: Artificial Sequence
<220> FEATURE:
<223> OTHER INFORMATION: amino acid sequence of E27K+ K123D mutant

<400> SEQUENCE: 128

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Asp Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 129
<211> LENGTH: 831
<212> TYPE: DNA
<213> ORGANISM: Artificial Sequence
<220> FEATURE:
<223> OTHER INFORMATION: gene sequence of E27K+ I39K mutant

<400> SEQUENCE: 129

```
atggaatcca agatcatcgg taaagtcaac ttcgaggagc atctgctgga taaagagctg     60
aaactgatcg acactttcaa attcaacgac agctacagcg aatacgcttc tggtaaatgg    120
aagacttgca tgctgtggaa ccgttctggt cagaaagatg accatctgtc tattgaacat    180
gatacctacg tgaaacctac tgaatacggc aaacagctgg catacgtaaa cgaaatcatc    240
gctaacacct ttaagaaaga acacatcaag acggtgcgtc tgttcatgtg tatcaacggc    300
ctgatcatcc cacacaaaga ctacctggaa ttcaagaaag gcttcacccg tatccacatc    360
ccgctgaaaa tcaacgaaca cgcactgacc tctgaagaag atgttgttta caacatgcag    420
aaaggtgaaa tttggttcat cgaaggccgt aaaatccaca gcgctgccaa tttcagcaaa    480
gtgaaacgta tcaacctggt catcgacttc gcgccggata ttccgtttga agaactgttc    540
ctgaattctg agaactatca accgaacctg atcccgaaaa tctctcaacg tacccagctg    600
aaagaagaag agctgggtta tatcaaaggt ctgtctaaaa ttatcaatga aatgaacttt    660
gacgacatcc tgtccattct gagcaaaatt cacttctatc gcaacgtttc ctccgaactg    720
gtttttggct ggctggacga aattgccacg gcgtccaaca actataacat tcagcgcaaa    780
gcgcaggaag taaccgatct gctgattcgc aaaggcccga ttaataacta a             831
```

<210> SEQ ID NO 130
<211> LENGTH: 276
<212> TYPE: PRT
<213> ORGANISM: Artificial Sequence
<220> FEATURE:
<223> OTHER INFORMATION: amino acid sequence of E27K+I39K mutant

<400> SEQUENCE: 130

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205
```

```
Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 131
<211> LENGTH: 831
<212> TYPE: DNA
<213> ORGANISM: Artificial Sequence
<220> FEATURE:
<223> OTHER INFORMATION: gene sequence of I39K+K123Q mutant

<400> SEQUENCE: 131

atggaatcca agatcatcgg taaagtcaac ttcgaggagc atctgctgga taaagagctg     60

aaactgatcg acactttcga gttcaacgac agctacagcg aatacgcttc tggtaaatgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctggata tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacaa aattgccacg gcgtccaaca actataacat tcagcgcaaa    780

gcgcaggaag taaccgatct gctgattcgc aaaggcccga ttaataacta a             831


<210> SEQ ID NO 132
<211> LENGTH: 276
<212> TYPE: PRT
<213> ORGANISM: Artificial Sequence
<220> FEATURE:
<223> OTHER INFORMATION: amino acid sequence of I39K+K123Q mutant

<400> SEQUENCE: 132

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80
```

```
Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Asp Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Lys Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 133
<211> LENGTH: 831
<212> TYPE: DNA
<213> ORGANISM: Artificial Sequence
<220> FEATURE:
<223> OTHER INFORMATION: gene sequence of I39K+ K123D mutant

<400> SEQUENCE: 133

```
atggaatcca agatcatcgg taaagtcaac ttcgaggagc atctgctgga taaagagctg     60

aaactgatcg acactttcga gttcaacgac agctacagcg aatacgcttc tggtaaatgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctggata tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 134

<211> LENGTH: 276
<212> TYPE: PRT
<213> ORGANISM: Artificial Sequence
<220> FEATURE:
<223> OTHER INFORMATION: amino acid sequence of I39K+ K123D mutant

<400> SEQUENCE: 134

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Asp Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 135
<211> LENGTH: 831
<212> TYPE: DNA
<213> ORGANISM: Artificial Sequence
<220> FEATURE:
<223> OTHER INFORMATION: gene sequence of S37C+I223V+ K123D mutant

<400> SEQUENCE: 135

```
atggaatcca agatcatcgg taaagtcaac ttcgaggagc atctgctgga taaagagctg     60

aaactgatcg acactttcga gttcaacgac agctacagcg aatacgcttg tggtatttgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240
```

-continued

```
gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctggata tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacgttc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 136
<211> LENGTH: 276
<212> TYPE: PRT
<213> ORGANISM: Artificial Sequence
<220> FEATURE:
<223> OTHER INFORMATION: amino acid sequence of S37C+I223V+ K123D mutant

<400> SEQUENCE: 136

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Cys Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Asp Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255
```

```
Ile Gln Arg Lys Ala Gln Glu Val Thr Asp Leu Leu Ile Arg Lys Gly
            260                 265                 270

Pro Ile Asn Asn
        275


<210> SEQ ID NO 137
<211> LENGTH: 831
<212> TYPE: DNA
<213> ORGANISM: Artificial Sequence
<220> FEATURE:
<223> OTHER INFORMATION: gene sequence of K123D+N165H mutant

<400> SEQUENCE: 137

atggaatcca agatcatcgg taaagtcaac ttcgaggagc atctgctgga taaagagctg      60

aaactgatcg acactttcga gttcaacgac agctacagcg aatacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctggata tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tccatctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 138
<211> LENGTH: 276
<212> TYPE: PRT
<213> ORGANISM: Artificial Sequence
<220> FEATURE:
<223> OTHER INFORMATION: amino acid sequence of K123D+N165H mutant

<400> SEQUENCE: 138

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Asp Ile Asn Glu His Ala
        115                 120                 125

Leu Thr Ser Glu Glu Asp Val Val Tyr Asn Met Gln Lys Gly Glu Ile
```

```
    130                 135                 140

Trp Phe Ile Glu Gly Arg Lys Ile His Ser Ala Ala Asn Phe Ser Lys
145                 150                 155                 160

Val Lys Arg Ile His Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 139
<211> LENGTH: 831
<212> TYPE: DNA
<213> ORGANISM: Artificial Sequence
<220> FEATURE:
<223> OTHER INFORMATION: gene sequence of I39R+K123D mutant

<400> SEQUENCE: 139

atggaatcca agatcatcgg taaagtcaac ttcgaggagc atctgctgga taaagagctg      60

aaactgatcg acactttcga gttcaacgac agctacagcg aatacgcttc tggtcgttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctggata tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 140
<211> LENGTH: 276
<212> TYPE: PRT
<213> ORGANISM: Artificial Sequence
<220> FEATURE:
<223> OTHER INFORMATION: amino acid sequence of I39R+K123D mutant

<400> SEQUENCE: 140

Met Glu Ser Lys Ile Ile Gly Lys Val Asn Phe Glu Glu His Leu Leu
1               5                   10                  15
```

```
Asp Lys Glu Leu Lys Leu Ile Asp Thr Phe Glu Phe Asn Asp Ser Tyr
            20                  25                  30

Ser Glu Tyr Ala Ser Gly Arg Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Asp Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 141
<211> LENGTH: 831
<212> TYPE: DNA
<213> ORGANISM: Artificial Sequence
<220> FEATURE:
<223> OTHER INFORMATION: gene sequence of E27K+I39K+K123D mutant

<400> SEQUENCE: 141

atggaatcca agatcatcgg taaagtcaac ttcgaggagc atctgctgga taaagagctg      60

aaactgatcg acactttcaa attcaacgac agctacagcg aatacgcttc tggtaaatgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctggata tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540
```

```
ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831


<210> SEQ ID NO 142
<211> LENGTH: 276
<212> TYPE: PRT
<213> ORGANISM: Artificial Sequence
<220> FEATURE:
<223> OTHER INFORMATION: amino acid sequence of E27K+I39K+K123D mutant

<400> SEQUENCE: 142

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Asp Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 143
<211> LENGTH: 831
<212> TYPE: DNA
```

-continued

<213> ORGANISM: Artificial Sequence
<220> FEATURE:
<223> OTHER INFORMATION: gene sequence of E27K+ I39R mutant

<400> SEQUENCE: 143

```
atggaatcca agatcatcgg taaagtcaac ttcgaggagc atctgctgga taaagagctg     60

aaactgatcg acactttcaa attcaacgac agctacagcg aatacgcttc tggtcgttgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 144
<211> LENGTH: 276
<212> TYPE: PRT
<213> ORGANISM: Artificial Sequence
<220> FEATURE:
<223> OTHER INFORMATION: amino acid sequence of E27K+ I39R mutant

<400> SEQUENCE: 144

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Ser Gly Arg Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190
```

```
Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 145
<211> LENGTH: 831
<212> TYPE: DNA
<213> ORGANISM: Artificial Sequence
<220> FEATURE:
<223> OTHER INFORMATION: gene sequence of I39R+N165H mutant

<400> SEQUENCE: 145

atggaatcca agatcatcgg taaagtcaac ttcgaggagc atctgctgga taaagagctg     60

aaactgatcg acactttcga gttcaacgac agctacagcg aatacgcttc tggtcgttgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tccatctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831


<210> SEQ ID NO 146
<211> LENGTH: 276
<212> TYPE: PRT
<213> ORGANISM: Artificial Sequence
<220> FEATURE:
<223> OTHER INFORMATION: amino acid sequence of I39R+N165H mutant

<400> SEQUENCE: 146

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Arg Trp Lys Thr Cys Met Leu Trp Asn Arg
        35                  40                  45

Ser Gly Gln Lys Asp Asp His Leu Ser Ile Glu His Asp Thr Tyr Val
    50                  55                  60
```

-continued

```
Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile His Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 147
<211> LENGTH: 831
<212> TYPE: DNA
<213> ORGANISM: Artificial Sequence
<220> FEATURE:
<223> OTHER INFORMATION: gene sequence of I39K+N165H mutant

<400> SEQUENCE: 147

atggaatcca agatcatcgg taaagtcaac ttcgaggagc atctgctgga taaagagctg      60

aaactgatcg acactttcga gttcaacgac agctacagcg aatacgcttc tggtaaatgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tccatctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831
```

<210> SEQ ID NO 148
<211> LENGTH: 276
<212> TYPE: PRT
<213> ORGANISM: Artificial Sequence
<220> FEATURE:
<223> OTHER INFORMATION: amino acid sequence of I39K+N165H mutant

<400> SEQUENCE: 148

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile His Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 149
<211> LENGTH: 831
<212> TYPE: DNA
<213> ORGANISM: Artificial Sequence
<220> FEATURE:
<223> OTHER INFORMATION: gene sequence of E27K+ I39K+K123D mutant

<400> SEQUENCE: 149

```
atggaatcca agatcatcgg taaagtcaac ttcgaggagc atctgctgga taaagagctg      60

aaactgatcg acactttcaa attcaacgac agctacagcg aatacgcttc tggtaaatgg     120
```

```
aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctggata tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831


<210> SEQ ID NO 150
<211> LENGTH: 276
<212> TYPE: PRT
<213> ORGANISM: Artificial Sequence
<220> FEATURE:
<223> OTHER INFORMATION: amino acid sequence of E27K+ I39K+K123D mutant

<400> SEQUENCE: 150

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Asp Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240
```

```
Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 151
<211> LENGTH: 831
<212> TYPE: DNA
<213> ORGANISM: Artificial Sequence
<220> FEATURE:
<223> OTHER INFORMATION: gene sequence of S37C+I223V+N165H mutant

<400> SEQUENCE: 151

atggaatcca agatcatcgg taaagtcaac ttcgaggagc atctgctgga taaagagctg      60

aaactgatcg acactttcga gttcaacgac agctacagcg aatacgcttg tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tccatctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacgttc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 152
<211> LENGTH: 276
<212> TYPE: PRT
<213> ORGANISM: Artificial Sequence
<220> FEATURE:
<223> OTHER INFORMATION: amino acid sequence of S37C+I223V+N165H mutant

<400> SEQUENCE: 152

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Cys Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
```

```
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile His Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 153
<211> LENGTH: 831
<212> TYPE: DNA
<213> ORGANISM: Artificial Sequence
<220> FEATURE:
<223> OTHER INFORMATION: gene sequence of K123D+W40F mutant

<400> SEQUENCE: 153

```
atggaatcca agatcatcgg taaagtcaac ttcgaggagc atctgctgga taaagagctg      60

aaactgatcg acactttcga gttcaacgac agctacagcg aatacgcttc tggtattttt     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctggata tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a             831
```

<210> SEQ ID NO 154
<211> LENGTH: 276
<212> TYPE: PRT
<213> ORGANISM: Artificial Sequence
<220> FEATURE:
<223> OTHER INFORMATION: amino acid sequence of K123D+W40F mutant

<400> SEQUENCE: 154

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Phe Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Asp Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 155
<211> LENGTH: 831
<212> TYPE: DNA
<213> ORGANISM: Artificial Sequence
<220> FEATURE:
<223> OTHER INFORMATION: gene sequence of E27K+N165H mutant

<400> SEQUENCE: 155

```
atggaatcca agatcatcgg taaagtcaac ttcgaggagc atctgctgga taaagagctg      60

aaactgatcg acactttcaa attcaacgac agctacagcg aatacgcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420
```

```
aaaggtgaaa tttggttcat cgaaggccgt aaaatccaca gcgctgccaa tttcagcaaa    480

gtgaaacgta tccatctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831


<210> SEQ ID NO 156
<211> LENGTH: 276
<212> TYPE: PRT
<213> ORGANISM: Artificial Sequence
<220> FEATURE:
<223> OTHER INFORMATION: amino acid sequence of E27K+N165H mutant

<400> SEQUENCE: 156

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile His Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 157
<211> LENGTH: 831
<212> TYPE: DNA
<213> ORGANISM: Artificial Sequence
<220> FEATURE:
<223> OTHER INFORMATION: gene sequence of E27K+ S37C+I223V+ K123D mutant

<400> SEQUENCE: 157

```
atggaatcca agatcatcgg taaagtcaac ttcgaggagc atctgctgga taaagagctg      60

aaactgatcg acactttcaa attcaacgac agctacagcg aatacgcttg tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctggata tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacgttc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831
```

<210> SEQ ID NO 158
<211> LENGTH: 276
<212> TYPE: PRT
<213> ORGANISM: Artificial Sequence
<220> FEATURE:
<223> OTHER INFORMATION: amino acid sequence of E27K+ S37C+I223V+ K123D mutant

<400> SEQUENCE: 158

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Cys Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Asp Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
```

```
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 159
<211> LENGTH: 831
<212> TYPE: DNA
<213> ORGANISM: Artificial Sequence
<220> FEATURE:
<223> OTHER INFORMATION: gene sequence of S37C+I39K+I223V+ K123D mutant

<400> SEQUENCE: 159

atggaatcca agatcatcgg taaagtcaac ttcgaggagc atctgctgga taaagagctg      60

aaactgatcg acactttcga gttcaacgac agctacagcg aatacgcttg tggtaaatgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctggata tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacgttc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 160
<211> LENGTH: 276
<212> TYPE: PRT
<213> ORGANISM: Artificial Sequence
<220> FEATURE:
<223> OTHER INFORMATION: amino acid sequence of S37C+I39K+I223V+ K123D
      mutant

<400> SEQUENCE: 160

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Cys Gly Lys Trp Lys Thr Cys Met Leu Trp Asn Arg
```

```
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Asp Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 161
<211> LENGTH: 831
<212> TYPE: DNA
<213> ORGANISM: Artificial Sequence
<220> FEATURE:
<223> OTHER INFORMATION: gene sequence of E27K+S37C+I39K+K123D+I98V
      mutant

<400> SEQUENCE: 161

atggaatcca agatcatcgg taaagtcaac ttcgaggagc atctgctgga taaagagctg     60

aaactgatcg acactttcaa attcaacgac agctacagcg aatacgcttg tggtaaatgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tgttaacggc    300

ctgatcatcc cacacaaaga ctacctggaa ttcaagaaag gcttcacccg tatccacatc    360

ccgctggata tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660
```

gacgacattc tgtccattct gagcaaaatt cacttctatc gcaacgtttc ctccgaactg 720
gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 162
<211> LENGTH: 276
<212> TYPE: PRT
<213> ORGANISM: Artificial Sequence
<220> FEATURE:
<223> OTHER INFORMATION: amino acid sequence of
E27K+S37C+I39K+K123D+I98V mutant

<400> SEQUENCE: 162

Met Glu Ser Lys Ile Ile Gly Lys Val Asn Phe Glu Glu His Leu Leu
1 5 10 15

Asp Lys Glu Leu Lys Leu Ile Asp Thr Phe Lys Phe Asn Asp Ser Tyr
20 25 30

Ser Glu Tyr Ala Cys Gly Lys Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Val Asn Gly Leu Ile Ile Pro His Lys Asp Tyr Leu Glu Phe Lys
100 105 110

Lys Gly Phe Thr Arg Ile His Ile Pro Leu Asp Ile Asn Glu His Ala
115 120 125

Leu Thr Ser Glu Glu Asp Val Val Tyr Asn Met Gln Lys Gly Glu Ile
130 135 140

Trp Phe Ile Glu Gly Arg Lys Ile His Ser Ala Ala Asn Phe Ser Lys
145 150 155 160

Val Lys Arg Ile Asn Leu Val Ile Asp Phe Ala Pro Asp Ile Pro Phe
165 170 175

Glu Glu Leu Phe Leu Asn Ser Glu Asn Tyr Gln Pro Asn Leu Ile Pro
180 185 190

Lys Ile Ser Gln Arg Thr Gln Leu Lys Glu Glu Glu Leu Gly Tyr Ile
195 200 205

Lys Gly Leu Ser Lys Ile Ile Asn Glu Met Asn Phe Asp Asp Ile Leu
210 215 220

Ser Ile Leu Ser Lys Ile His Phe Tyr Arg Asn Val Ser Ser Glu Leu
225 230 235 240

Val Phe Gly Trp Leu Asp Glu Ile Ala Thr Ala Ser Asn Asn Tyr Asn
245 250 255

Ile Gln Arg Lys Ala Gln Glu Val Thr Asp Leu Leu Ile Arg Lys Gly
260 265 270

Pro Ile Asn Asn
275

<210> SEQ ID NO 163
<211> LENGTH: 831
<212> TYPE: DNA
<213> ORGANISM: Artificial Sequence
<220> FEATURE:
<223> OTHER INFORMATION: gene sequence of E27K+S37C+I39K+K123D+I223V mutant

<400> SEQUENCE: 163

```
atggaatcca agatcatcgg taaagtcaac ttcgaggagc atctgctgga taaagagctg      60
aaactgatcg acactttcaa attcaacgac agctacagcg aatacgcttg tggtaaatgg     120
aagacttgca tgctgtggaa ccgttctggt cagaaagatg accatctgtc tattgaacat     180
gatacctacg tgaaacctac tgaatacggc aaacagctgg catacgtaaa cgaaatcatc     240
gctaacacct ttaagaaaga acacatcaag acggtgcgtc tgttcatgtg tatcaacggc     300
ctgatcatcc cacacaaaga ctacctggaa ttcaagaaag gcttcacccg tatccacatc     360
ccgctggata tcaacgaaca cgcactgacc tctgaagaag atgttgttta caacatgcag     420
aaaggtgaaa tttggttcat cgaaggccgt aaaatccaca gcgctgccaa tttcagcaaa     480
gtgaaacgta tcaacctggt catcgacttc gcgccggata ttccgtttga agaactgttc     540
ctgaattctg agaactatca accgaacctg atcccgaaaa tctctcaacg tacccagctg     600
aaagaagaag agctgggtta tatcaaaggt ctgtctaaaa ttatcaatga aatgaacttt     660
gacgacgttc tgtccattct gagcaaaatt cacttctatc gcaacgtttc ctccgaactg     720
gtttttggct ggctggacga aattgccacg gcgtccaaca actataacat tcagcgcaaa     780
gcgcaggaag taaccgatct gctgattcgc aaaggcccga ttaataacta a              831
```

```
<210> SEQ ID NO 164
<211> LENGTH: 276
<212> TYPE: PRT
<213> ORGANISM: Artificial Sequence
<220> FEATURE:
<223> OTHER INFORMATION: amino acid sequence of
      E27K+S37C+I39K+K123D+I223V mutant

<400> SEQUENCE: 164

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Cys Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Asp Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190
```

```
Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 165
<211> LENGTH: 831
<212> TYPE: DNA
<213> ORGANISM: Artificial Sequence
<220> FEATURE:
<223> OTHER INFORMATION: gene sequence of F26L+E27K+I39K+K123D mutant

<400> SEQUENCE: 165

```
atggaatcca agatcatcgg taaagtcaac ttcgaggagc atctgctgga taaagagctg     60

aaactgatcg acactctgaa attcaacgac agctacagcg aatacgcttc tggtaaatgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctggata tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 166
<211> LENGTH: 276
<212> TYPE: PRT
<213> ORGANISM: Artificial Sequence
<220> FEATURE:
<223> OTHER INFORMATION: amino acid sequence of F26L+E27K+I39K+K123D mutant

<400> SEQUENCE: 166

```
Met Glu Ser Lys Ile Ile Gly Lys Val Asn Phe Glu Glu His Leu Leu
1               5                   10                  15

Asp Lys Glu Leu Lys Leu Ile Asp Thr Leu Lys Phe Asn Asp Ser Tyr
            20                  25                  30

Ser Glu Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60
```

```
Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Asp Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 167
<211> LENGTH: 831
<212> TYPE: DNA
<213> ORGANISM: Artificial Sequence
<220> FEATURE:
<223> OTHER INFORMATION: gene sequence of I223V+S37C+E27K+I39K mutant

<400> SEQUENCE: 167

```
atggaatcca agatcatcgg taaagtcaac ttcgaggagc atctgctgga taaagagctg     60

aaactgatcg acactttcaa attcaacgac agctacagcg aatacgcttg tggtaaatgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacgttc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 168
<211> LENGTH: 276
<212> TYPE: PRT
<213> ORGANISM: Artificial Sequence
<220> FEATURE:
<223> OTHER INFORMATION: amino acid sequence of I223V+S37C+E27K+I39K
      mutant

<400> SEQUENCE: 168

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Cys Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 169
<211> LENGTH: 831
<212> TYPE: DNA
<213> ORGANISM: Artificial Sequence
<220> FEATURE:
<223> OTHER INFORMATION: gene sequence of I223V+S37C+E27K+N165H mutant

<400> SEQUENCE: 169

```
atggaatcca agatcatcgg taaagtcaac ttcgaggagc atctgctgga taaagagctg     60

aaactgatcg acactttcaa attcaacgac agctacagcg aatacgcttg tggtatttgg    120
```

```
aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tccatctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacgttc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831


<210> SEQ ID NO 170
<211> LENGTH: 276
<212> TYPE: PRT
<213> ORGANISM: Artificial Sequence
<220> FEATURE:
<223> OTHER INFORMATION: amino acid sequence of I223V+S37C+E27K+N165H
      mutant

<400> SEQUENCE: 170

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Cys Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile His Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
```

-continued

```
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 171
<211> LENGTH: 831
<212> TYPE: DNA
<213> ORGANISM: Artificial Sequence
<220> FEATURE:
<223> OTHER INFORMATION: gene sequence of K123D+Y35W mutant

<400> SEQUENCE: 171

atggaatcca agatcatcgg taaagtcaac ttcgaggagc atctgctgga taaagagctg      60

aaactgatcg acactttcga gttcaacgac agctacagcg aatgggcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctggata tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 172
<211> LENGTH: 276
<212> TYPE: PRT
<213> ORGANISM: Artificial Sequence
<220> FEATURE:
<223> OTHER INFORMATION: amino acid sequence of K123D+Y35W mutant

<400> SEQUENCE: 172

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Trp Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110
```

```
Lys Gly Phe Thr Arg Ile His Ile Pro Leu Asp Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 173
<211> LENGTH: 831
<212> TYPE: DNA
<213> ORGANISM: Artificial Sequence
<220> FEATURE:
<223> OTHER INFORMATION: gene sequence of K123D+Y35W+I120V mutant

<400> SEQUENCE: 173

```
atggaatcca agatcatcgg taaagtcaac ttcgaggagc atctgctgga taaagagctg      60

aaactgatcg acactttcga gttcaacgac agctacagcg aatgggcttc tggtatttgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacgtg     360

ccgctggata tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831
```

<210> SEQ ID NO 174
<211> LENGTH: 276
<212> TYPE: PRT
<213> ORGANISM: Artificial Sequence
<220> FEATURE:
<223> OTHER INFORMATION: amino acid sequence of K123D+Y35W+I120V mutant

<400> SEQUENCE: 174

Met Glu Ser Lys Ile Ile Gly Lys Val Asn Phe Glu Glu His Leu Leu
1 5 10 15

Asp Lys Glu Leu Lys Leu Ile Asp Thr Phe Glu Phe Asn Asp Ser Tyr
20 25 30

Ser Glu Trp Ala Ser Gly Ile Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys
100 105 110

Lys Gly Phe Thr Arg Ile His Val Pro Leu Asp Ile Asn Glu His Ala
115 120 125

Leu Thr Ser Glu Glu Asp Val Val Tyr Asn Met Gln Lys Gly Glu Ile
130 135 140

Trp Phe Ile Glu Gly Arg Lys Ile His Ser Ala Ala Asn Phe Ser Lys
145 150 155 160

Val Lys Arg Ile Asn Leu Val Ile Asp Phe Ala Pro Asp Ile Pro Phe
165 170 175

Glu Glu Leu Phe Leu Asn Ser Glu Asn Tyr Gln Pro Asn Leu Ile Pro
180 185 190

Lys Ile Ser Gln Arg Thr Gln Leu Lys Glu Glu Glu Leu Gly Tyr Ile
195 200 205

Lys Gly Leu Ser Lys Ile Ile Asn Glu Met Asn Phe Asp Asp Ile Leu
210 215 220

Ser Ile Leu Ser Lys Ile His Phe Tyr Arg Asn Val Ser Ser Glu Leu
225 230 235 240

Val Phe Gly Trp Leu Asp Glu Ile Ala Thr Ala Ser Asn Asn Tyr Asn
245 250 255

Ile Gln Arg Lys Ala Gln Glu Val Thr Asp Leu Leu Ile Arg Lys Gly
260 265 270

Pro Ile Asn Asn
275

<210> SEQ ID NO 175
<211> LENGTH: 831
<212> TYPE: DNA
<213> ORGANISM: Artificial Sequence
<220> FEATURE:
<223> OTHER INFORMATION: gene sequence of E27K+Y35W mutant

<400> SEQUENCE: 175
atggaatcca agatcatcgg taaagtcaac ttcgaggagc atctgctgga taaagagctg 60
aaactgatcg acactttcaa attcaacgac agctacagcg aatgggcttc tggtatttgg 120
aagacttgca tgctgtggaa ccgttctggt cagaaagatg accatctgtc tattgaacat 180
gatacctacg tgaaacctac tgaatacggc aaacagctgg catacgtaaa cgaaatcatc 240
gctaacacct ttaagaaaga acacatcaag acggtgcgtc tgttcatgtg tatcaacggc 300
ctgatcatcc cacacaaaga ctacctggaa ttcaagaaag gcttcacccg tatccacatc 360

-continued

```
ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831


<210> SEQ ID NO 176
<211> LENGTH: 276
<212> TYPE: PRT
<213> ORGANISM: Artificial Sequence
<220> FEATURE:
<223> OTHER INFORMATION: amino acid sequence of E27K+Y35W mutant

<400> SEQUENCE: 176

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Trp Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 177
<211> LENGTH: 831
<212> TYPE: DNA
<213> ORGANISM: Artificial Sequence
<220> FEATURE:
<223> OTHER INFORMATION: gene sequence of I39R+Y35W mutant

<400> SEQUENCE: 177
atggaatcca agatcatcgg taaagtcaac ttcgaggagc atctgctgga taaagagctg 60
aaactgatcg acactttcga gttcaacgac agctacagcg aatgggcttc tggtcgttgg 120
aagacttgca tgctgtggaa ccgttctggt cagaaagatg accatctgtc tattgaacat 180
gatacctacg tgaaacctac tgaatacggc aaacagctgg catacgtaaa cgaaatcatc 240
gctaacacct ttaagaaaga acacatcaag acggtgcgtc tgttcatgtg tatcaacggc 300
ctgatcatcc cacacaaaga ctacctggaa ttcaagaaag gcttcacccg tatccacatc 360
ccgctgaaaa tcaacgaaca cgcactgacc tctgaagaag atgttgttta caacatgcag 420
aaaggtgaaa tttggttcat cgaaggccgt aaaatccaca gcgctgccaa tttcagcaaa 480
gtgaaacgta tcaacctggt catcgacttc gcgccggata ttccgtttga agaactgttc 540
ctgaattctg agaactatca accgaacctg atcccgaaaa tctctcaacg tacccagctg 600
aaagaagaag agctgggtta tatcaaaggt ctgtctaaaa ttatcaatga aatgaacttt 660
gacgacatcc tgtccattct gagcaaaatt cacttctatc gcaacgtttc ctccgaactg 720
gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 178
<211> LENGTH: 276
<212> TYPE: PRT
<213> ORGANISM: Artificial Sequence
<220> FEATURE:
<223> OTHER INFORMATION: amino acid sequence of I39R+Y35W mutant

<400> SEQUENCE: 178

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Trp Ala Ser Gly Arg Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

```
Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 179
<211> LENGTH: 831
<212> TYPE: DNA
<213> ORGANISM: Artificial Sequence
<220> FEATURE:
<223> OTHER INFORMATION: gene sequence of S37C+I223V mutant

<400> SEQUENCE: 179

atggaatcca agatcatcgg taaagtcaac ttcgaggagc atctgctgga taaagagctg     60

aaactgatcg acactttcga gttcaacgac agctacagcg aatacgcttg tggtatttgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacgttc tgtccattct gagcaaaatt cacttctatc gcaacgtttc ctccgaactg    720

gtttttggct ggctggacga aattgccacg gcgtccaaca actataacat tcagcgcaaa    }780

gcgcaggaag taaccgatct gctgattcgc aaaggcccga ttaataacta a            831


<210> SEQ ID NO 180
<211> LENGTH: 276
<212> TYPE: PRT
<213> ORGANISM: Artificial Sequence
<220> FEATURE:
<223> OTHER INFORMATION: amino acid sequence of S37C+I223V mutant

<400> SEQUENCE: 180

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Cys Gly Ile Trp Lys Thr Cys Met Leu Trp Asn Arg
```

```
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 181
<211> LENGTH: 831
<212> TYPE: DNA
<213> ORGANISM: Artificial Sequence
<220> FEATURE:
<223> OTHER INFORMATION: gene sequence of E27K+I39K+Y35W mutant

<400> SEQUENCE: 181

atggaatcca agatcatcgg taaagtcaac ttcgaggagc atctgctgga taaagagctg      60

aaactgatcg acactttcaa attcaacgac agctacagcg aatgggcttc tggtaaatgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660
```

```
gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 182
<211> LENGTH: 276
<212> TYPE: PRT
<213> ORGANISM: Artificial Sequence
<220> FEATURE:
<223> OTHER INFORMATION: amino acid sequence of E27K+I39K+Y35W mutant

<400> SEQUENCE: 182

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Trp Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 183
<211> LENGTH: 831
<212> TYPE: DNA
<213> ORGANISM: Artificial Sequence
<220> FEATURE:
<223> OTHER INFORMATION: gene sequence of
      E27K+S37C+I39K+I98V+K123D+I223V mutant

<400> SEQUENCE: 183
atggaatcca agatcatcgg taaagtcaac ttcgaggagc atctgctgga taaagagctg 60
aaactgatcg acactttcaa attcaacgac agctacagcg aatacgcttg tggtaaatgg 120
aagacttgca tgctgtggaa ccgttctggt cagaaagatg accatctgtc tattgaacat 180
gatacctacg tgaaacctac tgaatacggc aaacagctgg catacgtaaa cgaaatcatc 240
gctaacacct ttaagaaaga acacatcaag acggtgcgtc tgttcatgtg tgttaacggc 300
ctgatcatcc cacacaaaga ctacctggaa ttcaagaaag gcttcacccg tatccacatc 360
ccgctggata tcaacgaaca cgcactgacc tctgaagaag atgttgttta caacatgcag 420
aaaggtgaaa tttggttcat cgaaggccgt aaaatccaca gcgctgccaa tttcagcaaa 480
gtgaaacgta tcaacctggt catcgacttc gcgccggata ttccgtttga agaactgttc 540
ctgaattctg agaactatca accgaacctg atcccgaaaa tctctcaacg tacccagctg 600
aaagaagaag agctgggtta tatcaaaggt ctgtctaaaa ttatcaatga aatgaacttt 660
gacgacgttc tgtccattct gagcaaaatt cacttctatc gcaacgtttc ctccgaactg 720
gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 184
<211> LENGTH: 276
<212> TYPE: PRT
<213> ORGANISM: Artificial Sequence
<220> FEATURE:
<223> OTHER INFORMATION: amino acid sequence of
E27K+S37C+I39K+I98V+K123D+I223V mutant

<400> SEQUENCE: 184

Met Glu Ser Lys Ile Ile Gly Lys Val Asn Phe Glu Glu His Leu Leu
1 5 10 15

Asp Lys Glu Leu Lys Leu Ile Asp Thr Phe Lys Phe Asn Asp Ser Tyr
20 25 30

Ser Glu Tyr Ala Cys Gly Lys Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Val Asn Gly Leu Ile Ile Pro His Lys Asp Tyr Leu Glu Phe Lys
100 105 110

Lys Gly Phe Thr Arg Ile His Ile Pro Leu Asp Ile Asn Glu His Ala
115 120 125

Leu Thr Ser Glu Glu Asp Val Val Tyr Asn Met Gln Lys Gly Glu Ile
130 135 140

Trp Phe Ile Glu Gly Arg Lys Ile His Ser Ala Ala Asn Phe Ser Lys
145 150 155 160

Val Lys Arg Ile Asn Leu Val Ile Asp Phe Ala Pro Asp Ile Pro Phe
165 170 175

Glu Glu Leu Phe Leu Asn Ser Glu Asn Tyr Gln Pro Asn Leu Ile Pro
180 185 190

Lys Ile Ser Gln Arg Thr Gln Leu Lys Glu Glu Glu Leu Gly Tyr Ile
195 200 205

```
Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 185
<211> LENGTH: 831
<212> TYPE: DNA
<213> ORGANISM: Artificial Sequence
<220> FEATURE:
<223> OTHER INFORMATION: gene sequence of E27K+I39K+K123D+N165H mutant

<400> SEQUENCE: 185

```
atggaatcca agatcatcgg taaagtcaac ttcgaggagc atctgctgga taaagagctg      60

aaactgatcg acactttcaa attcaacgac agctacagcg aatacgcttc tggtaaatgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctggata tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tccatctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831
```

<210> SEQ ID NO 186
<211> LENGTH: 276
<212> TYPE: PRT
<213> ORGANISM: Artificial Sequence
<220> FEATURE:
<223> OTHER INFORMATION: amino acid sequence of E27K+I39K+K123D+N165H mutant

<400> SEQUENCE: 186

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80
```

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys
100 105 110

Lys Gly Phe Thr Arg Ile His Ile Pro Leu Asp Ile Asn Glu His Ala
115 120 125

Leu Thr Ser Glu Glu Asp Val Val Tyr Asn Met Gln Lys Gly Glu Ile
130 135 140

Trp Phe Ile Glu Gly Arg Lys Ile His Ser Ala Ala Asn Phe Ser Lys
145 150 155 160

Val Lys Arg Ile His Leu Val Ile Asp Phe Ala Pro Asp Ile Pro Phe
165 170 175

Glu Glu Leu Phe Leu Asn Ser Glu Asn Tyr Gln Pro Asn Leu Ile Pro
180 185 190

Lys Ile Ser Gln Arg Thr Gln Leu Lys Glu Glu Glu Leu Gly Tyr Ile
195 200 205

Lys Gly Leu Ser Lys Ile Ile Asn Glu Met Asn Phe Asp Asp Ile Leu
210 215 220

Ser Ile Leu Ser Lys Ile His Phe Tyr Arg Asn Val Ser Ser Glu Leu
225 230 235 240

Val Phe Gly Trp Leu Asp Glu Ile Ala Thr Ala Ser Asn Asn Tyr Asn
245 250 255

Ile Gln Arg Lys Ala Gln Glu Val Thr Asp Leu Leu Ile Arg Lys Gly
260 265 270

Pro Ile Asn Asn
275

<210> SEQ ID NO 187
<211> LENGTH: 831
<212> TYPE: DNA
<213> ORGANISM: Artificial Sequence
<220> FEATURE:
<223> OTHER INFORMATION: gene sequence of E27K+I39R+Y35W mutant

<400> SEQUENCE: 187
atggaatcca agatcatcgg taaagtcaac ttcgaggagc atctgctgga taaagagctg 60
aaactgatcg acactttcaa attcaacgac agctacagcg aatgggcttc tggtcgttgg 120
aagacttgca tgctgtggaa ccgttctggt cagaaagatg accatctgtc tattgaacat 180
gatacctacg tgaaacctac tgaatacggc aaacagctgg catacgtaaa cgaaatcatc 240
gctaacacct ttaagaaaga acacatcaag acggtgcgtc tgttcatgtg tatcaacggc 300
ctgatcatcc cacacaaaga ctacctggaa ttcaagaaag gcttcacccg tatccacatc 360
ccgctgaaaa tcaacgaaca cgcactgacc tctgaagaag atgttgttta caacatgcag 420
aaaggtgaaa tttggttcat cgaaggccgt aaaatccaca gcgctgccaa tttcagcaaa 480
gtgaaacgta tcaacctggt catcgacttc gcgccggata ttccgtttga agaactgttc 540
ctgaattctg agaactatca accgaacctg atcccgaaaa tctctcaacg tacccagctg 600
aaagaagaag agctgggtta tatcaaaggt ctgtctaaaa ttatcaatga aatgaacttt 660
gacgacatcc tgtccattct gagcaaaatt cacttctatc gcaacgtttc ctccgaactg 720
gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 188
<211> LENGTH: 276
<212> TYPE: PRT
<213> ORGANISM: Artificial Sequence
<220> FEATURE:
<223> OTHER INFORMATION: amino acid sequence of E27K+I39R+Y35W mutant

<400> SEQUENCE: 188

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Trp Ala Ser Gly Arg Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 189
<211> LENGTH: 831
<212> TYPE: DNA
<213> ORGANISM: Artificial Sequence
<220> FEATURE:
<223> OTHER INFORMATION: gene sequence of S37C+I39K+N165H mutant

<400> SEQUENCE: 189

```
atggaatcca agatcatcgg taaagtcaac ttcgaggagc atctgctgga taaagagctg      60

aaactgatta tcactttcga gttcaacgac agctacagcg aatacgcttc tggtatttgg     120

aagacttgca tgctgtggaa ccgttctggt cagaaagatg accatctgtc tattgaacat     180
```

```
gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcggtaaa    480

gtgaaacgta tcgttctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 190
<211> LENGTH: 276
<212> TYPE: PRT
<213> ORGANISM: Artificial Sequence
<220> FEATURE:
<223> OTHER INFORMATION: amino acid sequence of S37C+I39K+N165H mutant

<400> SEQUENCE: 190

```
Met Glu Ser Lys Ile Ile Gly Lys Val Asn Phe Glu Glu His Leu Leu
1               5                   10                  15

Asp Lys Glu Leu Lys Leu Ile Ile Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Gly Lys
145                 150                 155                 160

Val Lys Arg Ile Val Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255
```

```
Ile Gln Arg Lys Ala Gln Glu Val Thr Asp Leu Leu Ile Arg Lys Gly
            260                 265                 270

Pro Ile Asn Asn
        275


<210> SEQ ID NO 191
<211> LENGTH: 831
<212> TYPE: DNA
<213> ORGANISM: Artificial Sequence
<220> FEATURE:
<223> OTHER INFORMATION: gene sequence of E27K+ I39K+D30S mutant

<400> SEQUENCE: 191

atggaatcca agatcatcgg taaagtcaac ttcgaggagc atctgctgga taaagagctg      60

aaactgatcg acactttcaa attcaacagc agctacagcg aatacgcttc tggtaaatgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 192
<211> LENGTH: 276
<212> TYPE: PRT
<213> ORGANISM: Artificial Sequence
<220> FEATURE:
<223> OTHER INFORMATION: amino acid sequence of E27K+ I39K+D30S mutant

<400> SEQUENCE: 192

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Ser Ser Tyr
            20                  25                  30

Ser Glu Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125
```

```
Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 193
<211> LENGTH: 831
<212> TYPE: DNA
<213> ORGANISM: Artificial Sequence
<220> FEATURE:
<223> OTHER INFORMATION: gene sequence of E27K+I39K+E34N mutant

<400> SEQUENCE: 193

```
atggaatcca agatcatcgg taaagtcaac ttcgaggagc atctgctgga taaagagctg      60

aaactgatcg acactttcaa attcaacgac agctacagca attacgcttc tggtaaatgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831
```

<210> SEQ ID NO 194
<211> LENGTH: 276
<212> TYPE: PRT
<213> ORGANISM: Artificial Sequence
<220> FEATURE:
<223> OTHER INFORMATION: amino acid sequence of E27K+I39K+E34N mutant

<400> SEQUENCE: 194

```
Met Glu Ser Lys Ile Ile Gly Lys Val Asn Phe Glu Glu His Leu Leu
```

-continued

```
1               5                   10                  15

Asp Lys Glu Leu Lys Leu Ile Asp Thr Phe Lys Phe Asn Asp Ser Tyr
            20                  25                  30

Ser Asn Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 195
<211> LENGTH: 831
<212> TYPE: DNA
<213> ORGANISM: Artificial Sequence
<220> FEATURE:
<223> OTHER INFORMATION: gene sequence of E27K+I39K+E34G mutant

<400> SEQUENCE: 195

atggaatcca agatcatcgg taaagtcaac ttcgaggagc atctgctgga taaagagctg      60

aaactgatcg acactttcaa attcaacgac agctacagcg gttacgcttc tggtaaatgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480
```

```
gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 196
<211> LENGTH: 276
<212> TYPE: PRT
<213> ORGANISM: Artificial Sequence
<220> FEATURE:
<223> OTHER INFORMATION: amino acid sequence of E27K+I39K+E34G mutant

<400> SEQUENCE: 196

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Gly Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 197
<211> LENGTH: 831

<212> TYPE: DNA
<213> ORGANISM: Artificial Sequence
<220> FEATURE:
<223> OTHER INFORMATION: gene sequence of E27K+I39K+S37W mutant

<400> SEQUENCE: 197

```
atggaatcca agatcatcgg taaagtcaac ttcgaggagc atctgctgga taaagagctg     60

aaactgatcg acactttcaa attcaacgac agctacagcg aatacgcttg ggtaaatgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 198
<211> LENGTH: 276
<212> TYPE: PRT
<213> ORGANISM: Artificial Sequence
<220> FEATURE:
<223> OTHER INFORMATION: amino acid sequence of E27K+I39K+S37W mutant

<400> SEQUENCE: 198

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Trp Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
```

180 185 190

Lys Ile Ser Gln Arg Thr Gln Leu Lys Glu Glu Glu Leu Gly Tyr Ile
195 200 205

Lys Gly Leu Ser Lys Ile Ile Asn Glu Met Asn Phe Asp Asp Ile Leu
210 215 220

Ser Ile Leu Ser Lys Ile His Phe Tyr Arg Asn Val Ser Ser Glu Leu
225 230 235 240

Val Phe Gly Trp Leu Asp Glu Ile Ala Thr Ala Ser Asn Asn Tyr Asn
245 250 255

Ile Gln Arg Lys Ala Gln Glu Val Thr Asp Leu Leu Ile Arg Lys Gly
260 265 270

Pro Ile Asn Asn
275

<210> SEQ ID NO 199
<211> LENGTH: 831
<212> TYPE: DNA
<213> ORGANISM: Artificial Sequence
<220> FEATURE:
<223> OTHER INFORMATION: gene sequence of E27K+I39K+S37E mutant

<400> SEQUENCE: 199
atggaatcca agatcatcgg taaagtcaac ttcgaggagc atctgctgga taaagagctg 60
aaactgatcg acactttcaa attcaacgac agctacagcg aatacgctga aggtaaatgg 120
aagacttgca tgctgtggaa ccgttctggt cagaaagatg accatctgtc tattgaacat 180
gatacctacg tgaaacctac tgaatacggc aaacagctgg catacgtaaa cgaaatcatc 240
gctaacacct ttaagaaaga acacatcaag acggtgcgtc tgttcatgtg tatcaacggc 300
ctgatcatcc cacacaaaga ctacctggaa ttcaagaaag gcttcacccg tatccacatc 360
ccgctgaaaa tcaacgaaca cgcactgacc tctgaagaag atgttgttta caacatgcag 420
aaaggtgaaa tttggttcat cgaaggccgt aaaatccaca gcgctgccaa tttcagcaaa 480
gtgaaacgta tcaacctggt catcgacttc gcgccggata ttccgtttga agaactgttc 540
ctgaattctg agaactatca accgaacctg atcccgaaaa tctctcaacg tacccagctg 600
aaagaagaag agctgggtta tatcaaaggt ctgtctaaaa ttatcaatga aatgaacttt 660
gacgacatcc tgtccattct gagcaaaatt cacttctatc gcaacgtttc ctccgaactg 720
gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 200
<211> LENGTH: 276
<212> TYPE: PRT
<213> ORGANISM: Artificial Sequence
<220> FEATURE:
<223> OTHER INFORMATION: amino acid sequence of E27K+I39K+S37E mutant

<400> SEQUENCE: 200

Met Glu Ser Lys Ile Ile Gly Lys Val Asn Phe Glu Glu His Leu Leu
1 5 10 15

Asp Lys Glu Leu Lys Leu Ile Asp Thr Phe Lys Phe Asn Asp Ser Tyr
20 25 30

Ser Glu Tyr Ala Glu Gly Lys Trp Lys Thr Cys Met Leu Trp Asn Arg
35 40 45

Ser Gly Gln Lys Asp Asp His Leu Ser Ile Glu His Asp Thr Tyr Val
50 55 60

```
Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 201
<211> LENGTH: 831
<212> TYPE: DNA
<213> ORGANISM: Artificial Sequence
<220> FEATURE:
<223> OTHER INFORMATION: gene sequence of E27K+I39K+Y35K mutant

<400> SEQUENCE: 201

```
atggaatcca agatcatcgg taaagtcaac ttcgaggagc atctgctgga taaagagctg     60

aaactgatcg acactttcaa attcaacgac agctacagcg aaaaagcttc tggtaaatgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780
```

gcgcaggaag taaccgatct gctgattcgc aaaggcccga ttaataacta a 831

<210> SEQ ID NO 202
<211> LENGTH: 276
<212> TYPE: PRT
<213> ORGANISM: Artificial Sequence
<220> FEATURE:
<223> OTHER INFORMATION: amino acid sequence of E27K+I39K+Y35K mutant

<400> SEQUENCE: 202

Met Glu Ser Lys Ile Ile Gly Lys Val Asn Phe Glu Glu His Leu Leu
1 5 10 15

Asp Lys Glu Leu Lys Leu Ile Asp Thr Phe Lys Phe Asn Asp Ser Tyr
20 25 30

Ser Glu Lys Ala Ser Gly Lys Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys
100 105 110

Lys Gly Phe Thr Arg Ile His Ile Pro Leu Lys Ile Asn Glu His Ala
115 120 125

Leu Thr Ser Glu Glu Asp Val Val Tyr Asn Met Gln Lys Gly Glu Ile
130 135 140

Trp Phe Ile Glu Gly Arg Lys Ile His Ser Ala Ala Asn Phe Ser Lys
145 150 155 160

Val Lys Arg Ile Asn Leu Val Ile Asp Phe Ala Pro Asp Ile Pro Phe
165 170 175

Glu Glu Leu Phe Leu Asn Ser Glu Asn Tyr Gln Pro Asn Leu Ile Pro
180 185 190

Lys Ile Ser Gln Arg Thr Gln Leu Lys Glu Glu Glu Leu Gly Tyr Ile
195 200 205

Lys Gly Leu Ser Lys Ile Ile Asn Glu Met Asn Phe Asp Asp Ile Leu
210 215 220

Ser Ile Leu Ser Lys Ile His Phe Tyr Arg Asn Val Ser Ser Glu Leu
225 230 235 240

Val Phe Gly Trp Leu Asp Glu Ile Ala Thr Ala Ser Asn Asn Tyr Asn
245 250 255

Ile Gln Arg Lys Ala Gln Glu Val Thr Asp Leu Leu Ile Arg Lys Gly
260 265 270

Pro Ile Asn Asn
275

<210> SEQ ID NO 203
<211> LENGTH: 831
<212> TYPE: DNA
<213> ORGANISM: Artificial Sequence
<220> FEATURE:
<223> OTHER INFORMATION: gene sequence of E27K+I39K+S37N mutant

<400> SEQUENCE: 203
atggaatcca agatcatcgg taaagtcaac ttcgaggagc atctgctgga taaagagctg 60
aaactgatcg acactttcaa attcaacgac agctacagcg aatacgctaa tggtaaatgg 120

```
aagacttgca tgctgtggaa ccgttctggt cagaaagatg accatctgtc tattgaacat    180
gatacctacg tgaaacctac tgaatacggc aaacagctgg catacgtaaa cgaaatcatc    240
gctaacacct ttaagaaaga acacatcaag acggtgcgtc tgttcatgtg tatcaacggc    300
ctgatcatcc cacacaaaga ctacctggaa ttcaagaaag gcttcacccg tatccacatc    360
ccgctgaaaa tcaacgaaca cgcactgacc tctgaagaag atgttgttta caacatgcag    420
aaaggtgaaa tttggttcat cgaaggccgt aaaatccaca gcgctgccaa tttcagcaaa    480
gtgaaacgta tcaacctggt catcgacttc gcgccggata ttccgtttga agaactgttc    540
ctgaattctg agaactatca accgaacctg atcccgaaaa tctctcaacg tacccagctg    600
aaagaagaag agctgggtta tatcaaaggt ctgtctaaaa ttatcaatga aatgaacttt    660
gacgacatcc tgtccattct gagcaaaatt cacttctatc gcaacgtttc ctccgaactg    720
gtttttggct ggctggacga aattgccacg gcgtccaaca actataacat tcagcgcaaa    780
gcgcaggaag taaccgatct gctgattcgc aaaggcccga ttaataacta a             831
```

<210> SEQ ID NO 204
<211> LENGTH: 276
<212> TYPE: PRT
<213> ORGANISM: Artificial Sequence
<220> FEATURE:
<223> OTHER INFORMATION: amino acid sequence of E27K+I39K+S37N mutant

<400> SEQUENCE: 204

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Asn Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240
```

Val Phe Gly Trp Leu Asp Glu Ile Ala Thr Ala Ser Asn Asn Tyr Asn
245 250 255

Ile Gln Arg Lys Ala Gln Glu Val Thr Asp Leu Leu Ile Arg Lys Gly
260 265 270

Pro Ile Asn Asn
275

<210> SEQ ID NO 205
<211> LENGTH: 831
<212> TYPE: DNA
<213> ORGANISM: Artificial Sequence
<220> FEATURE:
<223> OTHER INFORMATION: gene sequence of E27K+I39K+K123Q mutant

<400> SEQUENCE: 205
atggaatcca agatcatcgg taaagtcaac ttcgaggagc atctgctgga taaagagctg 60
aaactgatcg acactttcaa attcaacgac agctacagcg aatacgcttc tggtaaatgg 120
aagacttgca tgctgtggaa ccgttctggt cagaaagatg accatctgtc tattgaacat 180
gatacctacg tgaaacctac tgaatacggc aaacagctgg catacgtaaa cgaaatcatc 240
gctaacacct ttaagaaaga acacatcaag acggtgcgtc tgttcatgtg tatcaacggc 300
ctgatcatcc cacacaaaga ctacctggaa ttcaagaaag gcttcacccg tatccacatc 360
ccgctgcaga tcaacgaaca cgcactgacc tctgaagaag atgttgttta caacatgcag 420
aaaggtgaaa tttggttcat cgaaggccgt aaaatccaca gcgctgccaa tttcagcaaa 480
gtgaaacgta tcaacctggt catcgacttc gcgccggata ttccgtttga agaactgttc 540
ctgaattctg agaactatca accgaacctg atcccgaaaa tctctcaacg tacccagctg 600
aaagaagaag agctgggtta tatcaaaggt ctgtctaaaa ttatcaatga aatgaacttt 660
gacgacatcc tgtccattct gagcaaaatt cacttctatc gcaacgtttc ctccgaactg 720
gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 206
<211> LENGTH: 276
<212> TYPE: PRT
<213> ORGANISM: Artificial Sequence
<220> FEATURE:
<223> OTHER INFORMATION: amino acid sequence of E27K+I39K+K123Q mutant

<400> SEQUENCE: 206

Met Glu Ser Lys Ile Ile Gly Lys Val Asn Phe Glu Glu His Leu Leu
1 5 10 15

Asp Lys Glu Leu Lys Leu Ile Asp Thr Phe Lys Phe Asn Asp Ser Tyr
20 25 30

Ser Glu Tyr Ala Ser Gly Lys Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys
100 105 110

```
Lys Gly Phe Thr Arg Ile His Ile Pro Leu Gln Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 207
<211> LENGTH: 831
<212> TYPE: DNA
<213> ORGANISM: Artificial Sequence
<220> FEATURE:
<223> OTHER INFORMATION: gene sequence of E27K+I39K+K123S mutant

<400> SEQUENCE: 207

```
atggaatcca agatcatcgg taaagtcaac ttcgaggagc atctgctgga taaagagctg     60

aaactgatcg acactttcaa attcaacgac agctacagcg aatacgcttc tggtaaatgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgagca tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 208
<211> LENGTH: 276
<212> TYPE: PRT
<213> ORGANISM: Artificial Sequence
<220> FEATURE:
<223> OTHER INFORMATION: amino acid sequence of E27K+I39K+K123S mutant

<400> SEQUENCE: 208

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Ser Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 209
<211> LENGTH: 831
<212> TYPE: DNA
<213> ORGANISM: Artificial Sequence
<220> FEATURE:
<223> OTHER INFORMATION: gene sequence of E27K+I39K+K106Q+K112E mutant

<400> SEQUENCE: 209

```
atggaatcca agatcatcgg taaagtcaac ttcgaggagc atctgctgga taaagagctg     60

aaactgatcg acactttcaa attcaacgac agctacagcg aatacgcttc tggtaaatgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacaccagga ctacctggaa ttcgaaaaag gcttcacccg tatccacatc    360

ccgctgaaaa tcaacgaaca cgcactgacc tctgaagaag atgttgttta caacatgcag    420
```

```
aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

```
<210> SEQ ID NO 210
<211> LENGTH: 276
<212> TYPE: PRT
<213> ORGANISM: Artificial Sequence
<220> FEATURE:
<223> OTHER INFORMATION: amino acid sequence of E27K+I39K+K106Q+K112E
      mutant

<400> SEQUENCE: 210

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Gln Asp Tyr Leu Glu Phe Glu
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 211
<211> LENGTH: 831
<212> TYPE: DNA
<213> ORGANISM: Artificial Sequence
<220> FEATURE:
<223> OTHER INFORMATION: gene sequence of I98V+E27K+I39K mutant

<400> SEQUENCE: 211

```
atggaatcca agatcatcgg taaagtcaac ttcgaggagc atctgctgga taaagagctg     60

aaactgatcg acactttcaa attcaacgac agctacagcg aatacgcttc tggtaaatgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tgttaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 212
<211> LENGTH: 276
<212> TYPE: PRT
<213> ORGANISM: Artificial Sequence
<220> FEATURE:
<223> OTHER INFORMATION: amino acid sequence of I98V+E27K+I39K mutant

<400> SEQUENCE: 212

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Val Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160
```

```
Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 213
<211> LENGTH: 831
<212> TYPE: DNA
<213> ORGANISM: Artificial Sequence
<220> FEATURE:
<223> OTHER INFORMATION: gene sequence of E27K+I39K+I118F mutant

<400> SEQUENCE: 213

atggaatcca agatcatcgg taaagtcaac ttcgaggagc atctgctgga taaagagctg      60

aaactgatcg acactttcaa attcaacgac agctacagcg aatacgcttc tggtaaatgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg ttttcacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 214
<211> LENGTH: 276
<212> TYPE: PRT
<213> ORGANISM: Artificial Sequence
<220> FEATURE:
<223> OTHER INFORMATION: amino acid sequence of E27K+I39K+I118F mutant

<400> SEQUENCE: 214

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Ser Gly Lys Trp Lys Thr Cys Met Leu Trp Asn Arg
```

```
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Phe His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 215
<211> LENGTH: 831
<212> TYPE: DNA
<213> ORGANISM: Artificial Sequence
<220> FEATURE:
<223> OTHER INFORMATION: gene sequence of E27K+I39K+S37T mutant

<400> SEQUENCE: 215

```
atggaatcca agatcatcgg taaagtcaac ttcgaggagc atctgctgga taaagagctg      60

aaactgatcg acactttcaa attcaacgac agctacagcg aatacgctac cggtaaatgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660
```

```
gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831


<210> SEQ ID NO 216
<211> LENGTH: 276
<212> TYPE: PRT
<213> ORGANISM: Artificial Sequence
<220> FEATURE:
<223> OTHER INFORMATION: amino acid sequence of E27K+I39K+S37T mutant

<400> SEQUENCE: 216

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Thr Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 217
<211> LENGTH: 831
<212> TYPE: DNA
<213> ORGANISM: Artificial Sequence
<220> FEATURE:
<223> OTHER INFORMATION: gene sequence of E27K+I39K+K123I mutant

<400> SEQUENCE: 217
```

```
atggaatcca agatcatcgg taaagtcaac ttcgaggagc atctgctgga taaagagctg     60

aaactgatcg acactttcaa attcaacgac agctacagcg aatacgcttc tggtaaatgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgatta tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a              831
```

```
<210> SEQ ID NO 218
<211> LENGTH: 276
<212> TYPE: PRT
<213> ORGANISM: Artificial Sequence
<220> FEATURE:
<223> OTHER INFORMATION: amino acid sequence of E27K+I39K+K123I mutant

<400> SEQUENCE: 218

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Ile Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
```

```
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 219
<211> LENGTH: 831
<212> TYPE: DNA
<213> ORGANISM: Artificial Sequence
<220> FEATURE:
<223> OTHER INFORMATION: gene sequence of K106Q+K112E+I223V mutant

<400> SEQUENCE: 219

```
atggaatcca agatcatcgg taaagtcaac ttcgaggagc atctgctgga taaagagctg     60

aaactgatcg acactttcga gttcaacgac agctacagcg aatacgcttc tggtatttgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacaccagga ctacctggaa ttcgaaaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacgttc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 220
<211> LENGTH: 276
<212> TYPE: PRT
<213> ORGANISM: Artificial Sequence
<220> FEATURE:
<223> OTHER INFORMATION: amino acid sequence of K106Q+K112E+I223V mutant

<400> SEQUENCE: 220

```
Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95
```

```
Cys Ile Asn Gly Leu Ile Ile Pro His Gln Asp Tyr Leu Glu Phe Glu
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 221
<211> LENGTH: 831
<212> TYPE: DNA
<213> ORGANISM: Artificial Sequence
<220> FEATURE:
<223> OTHER INFORMATION: gene sequence of H14R+E34G+K106Q+K112E+I223V mutant

<400> SEQUENCE: 221

```
atggaatcca agatcatcgg taaagtcaac ttcgaggagc gtctgctgga taaagagctg     60

aaactgatcg acactttcga gttcaacgac agctacagcg gttacgcttc tggtatttgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacaccagga ctacctggaa ttcgaaaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacgttc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 222
<211> LENGTH: 276

<212> TYPE: PRT
<213> ORGANISM: Artificial Sequence
<220> FEATURE:
<223> OTHER INFORMATION: amino acid sequence of
H14R+E34G+K106Q+K112E+I223V mutant

<400> SEQUENCE: 222

```
Met Glu Ser Lys Ile Ile Gly Lys Val Asn Phe Glu Glu Arg Leu Leu
1               5                   10                  15

Asp Lys Glu Leu Lys Leu Ile Asp Thr Phe Glu Phe Asn Asp Ser Tyr
            20                  25                  30

Ser Gly Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Gln Asp Tyr Leu Glu Phe Glu
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 223
<211> LENGTH: 831
<212> TYPE: DNA
<213> ORGANISM: Artificial Sequence
<220> FEATURE:
<223> OTHER INFORMATION: gene sequence of E27K+I39K+E34L mutant

<400> SEQUENCE: 223

```
atggaatcca agatcatcgg taaagtcaac ttcgaggagc atctgctgga taaagagctg     60

aaactgatcg acactttcaa attcaacgac agctacagcc tgtacgcttc tggtaaatgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240
```

```
gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 224
<211> LENGTH: 276
<212> TYPE: PRT
<213> ORGANISM: Artificial Sequence
<220> FEATURE:
<223> OTHER INFORMATION: amino acid sequence of E27K+I39K+E34L mutant

<400> SEQUENCE: 224

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Leu Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255
```

```
Ile Gln Arg Lys Ala Gln Glu Val Thr Asp Leu Leu Ile Arg Lys Gly
            260                 265                 270

Pro Ile Asn Asn
        275


<210> SEQ ID NO 225
<211> LENGTH: 831
<212> TYPE: DNA
<213> ORGANISM: Artificial Sequence
<220> FEATURE:
<223> OTHER INFORMATION: gene sequence of E27K+I39K+S37F+I58T mutant

<400> SEQUENCE: 225

atggaatcca agatcatcgg taaagtcaac ttcgaggagc atctgctgga taaagagctg      60

aaactgatcg acactttcaa attcaacgac agctacagcg aatacgcttt tggtaaatgg     120

aagacttgca tgctgtggaa ccgttctggt cagaaagatg accatctgtc taccgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 226
<211> LENGTH: 276
<212> TYPE: PRT
<213> ORGANISM: Artificial Sequence
<220> FEATURE:
<223> OTHER INFORMATION: amino acid sequence of E27K+I39K+S37F+I58T
      mutant

<400> SEQUENCE: 226

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Phe Gly Lys Trp Lys Thr Cys Met Leu Trp Asn Arg
        35                  40                  45

Ser Gly Gln Lys Asp Asp His Leu Ser Thr Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125
```

```
Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 227
<211> LENGTH: 831
<212> TYPE: DNA
<213> ORGANISM: Artificial Sequence
<220> FEATURE:
<223> OTHER INFORMATION: gene sequence of E27K+I39K+S37F+I58Y mutant

<400> SEQUENCE: 227

atggaatcca agatcatcgg taaagtcaac ttcgaggagc atctgctgga taaagagctg      60

aaactgatcg acactttcaa attcaacgac agctacagcg aatacgcttt tggtaaatgg     120

aagacttgca tgctgtggaa ccgttctggt cagaaagatg accatctgtc ttatgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 228
<211> LENGTH: 276
<212> TYPE: PRT
<213> ORGANISM: Artificial Sequence
<220> FEATURE:
<223> OTHER INFORMATION: amino acid sequence of E27K+I39K+S37F+I58Y
      mutant

<400> SEQUENCE: 228
```

-continued

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Phe Gly Lys Trp Lys Thr Cys Met Leu Trp Asn Arg
        35                  40                  45

Ser Gly Gln Lys Asp Asp His Leu Ser Tyr Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 229
<211> LENGTH: 831
<212> TYPE: DNA
<213> ORGANISM: Artificial Sequence
<220> FEATURE:
<223> OTHER INFORMATION: gene sequence of E27K+I39K+S37F+I58A mutant

<400> SEQUENCE: 229

```
atggaatcca agatcatcgg taaagtcaac ttcgaggagc atctgctgga taaagagctg      60

aaactgatcg acactttcaa attcaacgac agctacagcg aatacgcttt tggtaaatgg     120

aagacttgca tgctgtggaa ccgttctggt cagaaagatg accatctgtc tgcagaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480
```

```
gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

```
<210> SEQ ID NO 230
<211> LENGTH: 276
<212> TYPE: PRT
<213> ORGANISM: Artificial Sequence
<220> FEATURE:
<223> OTHER INFORMATION: amino acid sequence of E27K+I39K+S37F+I58A
      mutant

<400> SEQUENCE: 230

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Phe Gly Lys Trp Lys Thr Cys Met Leu Trp Asn Arg
        35                  40                  45

Ser Gly Gln Lys Asp Asp His Leu Ser Ala Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 231
<211> LENGTH: 831
<212> TYPE: DNA
<213> ORGANISM: Artificial Sequence
<220> FEATURE:
<223> OTHER INFORMATION: gene sequence of E27K+I39K+S37F+I58R mutant

<400> SEQUENCE: 231

```
atggaatcca agatcatcgg taaagtcaac ttcgaggagc atctgctgga taaagagctg      60

aaactgatcg acactttcaa attcaacgac agctacagcg aatacgcttt tggtaaatgg     120

aagacttgca tgctgtggaa ccgttctggt cagaaagatg accatctgtc tcgtgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831
```

<210> SEQ ID NO 232
<211> LENGTH: 276
<212> TYPE: PRT
<213> ORGANISM: Artificial Sequence
<220> FEATURE:
<223> OTHER INFORMATION: amino acid sequence of E27K+I39K+S37F+I58R mutant

<400> SEQUENCE: 232

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Phe Gly Lys Trp Lys Thr Cys Met Leu Trp Asn Arg
        35                  40                  45

Ser Gly Gln Lys Asp Asp His Leu Ser Arg Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
```

```
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 233
<211> LENGTH: 831
<212> TYPE: DNA
<213> ORGANISM: Artificial Sequence
<220> FEATURE:
<223> OTHER INFORMATION: gene sequence of E27K+I39K+S37F+I58V mutant

<400> SEQUENCE: 233

atggaatcca agatcatcgg taaagtcaac ttcgaggagc atctgctgga taaagagctg     60

aaactgatcg acactttcaa attcaacgac agctacagcg aatacgcttt tggtaaatgg    120

aagacttgca tgctgtggaa ccgttctggt cagaaagatg accatctgtc tgttgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831


<210> SEQ ID NO 234
<211> LENGTH: 276
<212> TYPE: PRT
<213> ORGANISM: Artificial Sequence
<220> FEATURE:
<223> OTHER INFORMATION: amino acid sequence of E27K+I39K+S37F+I58V
      mutant

<400> SEQUENCE: 234

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Phe Gly Lys Trp Lys Thr Cys Met Leu Trp Asn Arg
```

-continued

```
        35                  40                  45

Ser Gly Gln Lys Asp Asp His Leu Ser Val Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 235
<211> LENGTH: 831
<212> TYPE: DNA
<213> ORGANISM: Artificial Sequence
<220> FEATURE:
<223> OTHER INFORMATION: gene sequence of E27K+I39K+S37F+I58S mutant

<400> SEQUENCE: 235

```
atggaatcca agatcatcgg taaagtcaac ttcgaggagc atctgctgga taaagagctg     60

aaactgatcg acactttcaa attcaacgac agctacagcg aatacgcttt tggtaaatgg    120

aagacttgca tgctgtggaa ccgttctggt cagaaagatg accatctgtc tagtgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660
```

-continued

```
gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 236
<211> LENGTH: 276
<212> TYPE: PRT
<213> ORGANISM: Artificial Sequence
<220> FEATURE:
<223> OTHER INFORMATION: amino acid sequence of E27K+I39K+S37F+I58S mutant

<400> SEQUENCE: 236

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Phe Gly Lys Trp Lys Thr Cys Met Leu Trp Asn Arg
        35                  40                  45

Ser Gly Gln Lys Asp Asp His Leu Ser Ser Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 237
<211> LENGTH: 831
<212> TYPE: DNA
<213> ORGANISM: Artificial Sequence
<220> FEATURE:
<223> OTHER INFORMATION: gene sequence of E27K+I39K+S37N+I58C mutant

<400> SEQUENCE: 237

```
atggaatcca agatcatcgg taaagtcaac ttcgaggagc atctgctgga taaagagctg     60
aaactgatcg acactttcaa attcaacgac agctacagcg aatacgctaa tggtaaatgg    120
aagacttgca tgctgtggaa ccgttctggt cagaaagatg accatctgtc ttgtgaacat    180
gatacctacg tgaaacctac tgaatacggc aaacagctgg catacgtaaa cgaaatcatc    240
gctaacacct ttaagaaaga acacatcaag acggtgcgtc tgttcatgtg tatcaacggc    300
ctgatcatcc cacacaaaga ctacctggaa ttcaagaaag gcttcacccg tatccacatc    360
ccgctgaaaa tcaacgaaca cgcactgacc tctgaagaag atgttgttta caacatgcag    420
aaaggtgaaa tttggttcat cgaaggccgt aaaatccaca gcgctgccaa tttcagcaaa    480
gtgaaacgta tcaacctggt catcgacttc gcgccggata ttccgtttga agaactgttc    540
ctgaattctg agaactatca accgaacctg atcccgaaaa tctctcaacg tacccagctg    600
aaagaagaag agctgggtta tatcaaaggt ctgtctaaaa ttatcaatga aatgaacttt    660
gacgacatcc tgtccattct gagcaaaatt cacttctatc gcaacgtttc ctccgaactg    720
gtttttggct ggctggacga aattgccacg gcgtccaaca actataacat tcagcgcaaa    780
gcgcaggaag taaccgatct gctgattcgc aaaggcccga ttaataacta a             831
```

<210> SEQ ID NO 238
<211> LENGTH: 276
<212> TYPE: PRT
<213> ORGANISM: Artificial Sequence
<220> FEATURE:
<223> OTHER INFORMATION: amino acid sequence of E27K+I39K+S37N+I58C mutant

<400> SEQUENCE: 238

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Asn Gly Lys Trp Lys Thr Cys Met Leu Trp Asn Arg
        35                  40                  45

Ser Gly Gln Lys Asp Asp His Leu Ser Cys Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205
```

```
Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

```
<210> SEQ ID NO 239
<211> LENGTH: 831
<212> TYPE: DNA
<213> ORGANISM: Artificial Sequence
<220> FEATURE:
<223> OTHER INFORMATION: gene sequence of E27K+D30S+I39K+I58R+K112E
      mutant

<400> SEQUENCE: 239

atggaatcca agatcatcgg taaagtcaac ttcgaggagc atctgctgga taaagagctg      60

aaactgatcg acactttcaa attcaacagc agctacagcg aatacgcttc tggtaaatgg     120

aagacttgca tgctgtggaa ccgttctggt cagaaagatg accatctgtc tcgtgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcgagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831
```

```
<210> SEQ ID NO 240
<211> LENGTH: 276
<212> TYPE: PRT
<213> ORGANISM: Artificial Sequence
<220> FEATURE:
<223> OTHER INFORMATION: amino acid sequence of
      E27K+D30S+I39K+I58R+K112E mutant

<400> SEQUENCE: 240

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Ser Ser Tyr
            20                  25                  30

Ser Glu Tyr Ala Ser Gly Lys Trp Lys Thr Cys Met Leu Trp Asn Arg
        35                  40                  45

Ser Gly Gln Lys Asp Asp His Leu Ser Arg Glu His Asp Thr Tyr Val
    50                  55                  60

Lys Pro Thr Glu Tyr Gly Lys Gln Leu Ala Tyr Val Asn Glu Ile Ile
```

```
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Glu
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 241
<211> LENGTH: 831
<212> TYPE: DNA
<213> ORGANISM: Artificial Sequence
<220> FEATURE:
<223> OTHER INFORMATION: gene sequence of E27K+E34N+I39K+I58Y+I223V mutant

<400> SEQUENCE: 241

```
atggaatcca agatcatcgg taaagtcaac ttcgaggagc atctgctgga taaagagctg     60

aaactgatcg acactttcaa attcaacgac agctacagca attacgcttc tggtaaatgg    120

aagacttgca tgctgtggaa ccgttctggt cagaaagatg accatctgtc ttatgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacgttc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 242
<211> LENGTH: 276
<212> TYPE: PRT
<213> ORGANISM: Artificial Sequence
<220> FEATURE:
<223> OTHER INFORMATION: amino acid sequence of
E27K+E34N+I39K+I58Y+I223V mutant

<400> SEQUENCE: 242

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Asn Tyr Ala Ser Gly Lys Trp Lys Thr Cys Met Leu Trp Asn Arg
        35                  40                  45

Ser Gly Gln Lys Asp Asp His Leu Ser Tyr Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 243
<211> LENGTH: 831
<212> TYPE: DNA
<213> ORGANISM: Artificial Sequence
<220> FEATURE:
<223> OTHER INFORMATION: gene sequence of E27K+S37N+I39K+I58Y+D173G
mutant

<400> SEQUENCE: 243

```
atggaatcca agatcatcgg taaagtcaac ttcgaggagc atctgctgga taaagagctg      60
```

```
aaactgatcg acactttcaa attcaacgac agctacagca attacgcttc tggtaaatgg    120

aagacttgca tgctgtggaa ccgttctggt cagaaagatg accatctgtc ttatgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccgtata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

```
<210> SEQ ID NO 244
<211> LENGTH: 276
<212> TYPE: PRT
<213> ORGANISM: Artificial Sequence
<220> FEATURE:
<223> OTHER INFORMATION: amino acid sequence of
      E27K+S37N+I39K+I58Y+D173G mutant

<400> SEQUENCE: 244

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Asn Tyr Ala Ser Gly Lys Trp Lys Thr Cys Met Leu Trp Asn Arg
        35                  40                  45

Ser Gly Gln Lys Asp Asp His Leu Ser Tyr Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Tyr Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220
```

```
Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 245
<211> LENGTH: 831
<212> TYPE: DNA
<213> ORGANISM: Artificial Sequence
<220> FEATURE:
<223> OTHER INFORMATION: gene sequence of E27K+S37F+I39K+I58Y+D173G mutant

<400> SEQUENCE: 245

```
atggaatcca agatcatcgg taaagtcaac ttcgaggagc atctgctgga taaagagctg      60

aaactgatcg acactttcaa attcaacgac agctacagct tttacgcttc tggtaaatgg     120

aagacttgca tgctgtggaa ccgttctggt cagaaagatg accatctgtc ttatgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccgtata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831
```

<210> SEQ ID NO 246
<211> LENGTH: 276
<212> TYPE: PRT
<213> ORGANISM: Artificial Sequence
<220> FEATURE:
<223> OTHER INFORMATION: amino acid sequence of E27K+S37F+I39K+I58Y+D173G mutant

<400> SEQUENCE: 246

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Phe Tyr Ala Ser Gly Lys Trp Lys Thr Cys Met Leu Trp Asn Arg
        35                  40                  45

Ser Gly Gln Lys Asp Asp His Leu Ser Tyr Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95
```

```
Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Tyr Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 247
<211> LENGTH: 831
<212> TYPE: DNA
<213> ORGANISM: Artificial Sequence
<220> FEATURE:
<223> OTHER INFORMATION: gene sequence of E27K+I39K+S37N+I58A mutant

<400> SEQUENCE: 247

```
atggaatcca agatcatcgg taaagtcaac ttcgaggagc atctgctgga taaagagctg      60

aaactgatcg acactttcaa attcaacgac agctacagcg aatacgctaa tggtaaatgg     120

aagacttgca tgctgtggaa ccgttctggt cagaaagatg accatctgtc tgcagaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831
```

<210> SEQ ID NO 248
<211> LENGTH: 276
<212> TYPE: PRT

```
<213> ORGANISM: Artificial Sequence
<220> FEATURE:
<223> OTHER INFORMATION: amino acid sequence of E27K+I39K+S37N+I58A
      mutant

<400> SEQUENCE: 248

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Asn Gly Lys Trp Lys Thr Cys Met Leu Trp Asn Arg
        35                  40                  45

Ser Gly Gln Lys Asp Asp His Leu Ser Ala Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 249
<211> LENGTH: 831
<212> TYPE: DNA
<213> ORGANISM: Artificial Sequence
<220> FEATURE:
<223> OTHER INFORMATION: gene sequence of E27K+I39K+S37N+I58R+K123Q
      mutant

<400> SEQUENCE: 249

atggaatcca agatcatcgg taaagtcaac ttcgaggagc atctgctgga taaagagctg      60

aaactgatcg acactttcaa attcaacgac agctacagcg aatacgctaa tggtaaatgg     120

aagacttgca tgctgtggaa ccgttctggt cagaaagatg accatctgtc tcgtgaacat     180

gatacctacg tgaaacctac tgaatacggc aaacagctgg catacgtaaa cgaaatcatc     240
```

```
gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgcaga tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

```
<210> SEQ ID NO 250
<211> LENGTH: 276
<212> TYPE: PRT
<213> ORGANISM: Artificial Sequence
<220> FEATURE:
<223> OTHER INFORMATION: amino acid sequence of
      E27K+I39K+S37N+I58R+K123Q mutant

<400> SEQUENCE: 250

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Glu Tyr Ala Asn Gly Lys Trp Lys Thr Cys Met Leu Trp Asn Arg
        35                  40                  45

Ser Gly Gln Lys Asp Asp His Leu Ser Arg Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Gln Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255
```

```
Ile Gln Arg Lys Ala Gln Glu Val Thr Asp Leu Leu Ile Arg Lys Gly
            260                 265                 270

Pro Ile Asn Asn
        275


<210> SEQ ID NO 251
<211> LENGTH: 831
<212> TYPE: DNA
<213> ORGANISM: Artificial Sequence
<220> FEATURE:
<223> OTHER INFORMATION: sequence of E27K+S37F+I39K+I58Y+D173G+I118R
      mutant

<400> SEQUENCE: 251

atggaatcca agatcatcgg taaagtcaac ttcgaggagc atctgctgga taaagagctg      60

aaactgatcg acactttcaa attcaacgac agctacagct tttacgcttc tggtaaatgg     120

aagacttgca tgctgtggaa ccgttctggt cagaaagatg accatctgtc ttatgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tcgtcacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccgtata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacatcc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 252
<211> LENGTH: 276
<212> TYPE: PRT
<213> ORGANISM: Artificial Sequence
<220> FEATURE:
<223> OTHER INFORMATION: amino acid sequence of
      E27K+S37F+I39K+I58Y+D173G+I118R mutant

<400> SEQUENCE: 252

Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Phe Tyr Ala Ser Gly Lys Trp Lys Thr Cys Met Leu Trp Asn Arg
        35                  40                  45

Ser Gly Gln Lys Asp Asp His Leu Ser Tyr Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Arg His Ile Pro Leu Lys Ile Asn Glu His Ala
```

```
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Tyr Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 253
<211> LENGTH: 831
<212> TYPE: DNA
<213> ORGANISM: Artificial Sequence
<220> FEATURE:
<223> OTHER INFORMATION: gene sequence of E27K+E34L+S37N+I39K+I58R mutant

<400> SEQUENCE: 253

```
atggaatcca agatcatcgg taaagtcaac ttcgaggagc atctgctgga taaagagctg     60

aaactgatcg acactttcaa attcaacgac agctacagcc tgtacgctaa tggtaaatgg    120

aagacttgca tgctgtggaa ccgttctggt cagaaagatg accatctgtc tcgtgaacat    180

gatacctacg tgaaacctac tgaatacggc aaacagctgg catacgtaaa cgaaatcatc    240

gctaacacct ttaagaaaga acacatcaag acggtgcgtc tgttcatgtg tatcaacggc    300

ctgatcatcc cacacaaaga ctacctggaa ttcaagaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 254
<211> LENGTH: 276
<212> TYPE: PRT
<213> ORGANISM: Artificial Sequence
<220> FEATURE:
<223> OTHER INFORMATION: amino acid sequence of E27K+E34L+S37N+I39K+I58R mutant

<400> SEQUENCE: 254

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Leu Tyr Ala Asn Gly Lys Trp Lys Thr Cys Met Leu Trp Asn Arg
        35                  40                  45

Ser Gly Gln Lys Asp Asp His Leu Ser Arg Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 255
<211> LENGTH: 831
<212> TYPE: DNA
<213> ORGANISM: Artificial Sequence
<220> FEATURE:
<223> OTHER INFORMATION: gene sequence of E27K+E34L+S37N+I39K+I58Y+D173G mutant

<400> SEQUENCE: 255

```
atggaatcca agatcatcgg taaagtcaac ttcgaggagc atctgctgga taaagagctg      60

aaactgatcg acactttcaa attcaacgac agctacagcc tgtacgctaa tggtaaatgg     120

aagacttgca tgctgtggaa ccgttctggt cagaaagatg accatctgtc ttatgaacat     180

gatacctacg tgaaacctac tgaatacggc aaacagctgg catacgtaaa cgaaatcatc     240

gctaacacct ttaagaaaga acacatcaag acggtgcgtc tgttcatgtg tatcaacggc     300

ctgatcatcc cacacaaaga ctacctggaa ttcaagaaag gcttcacccg tcgtcacatc     360
```

```
ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacatcc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 256
<211> LENGTH: 276
<212> TYPE: PRT
<213> ORGANISM: Artificial Sequence
<220> FEATURE:
<223> OTHER INFORMATION: amino acid sequence of
E27K+E34L+S37N+I39K+I58Y+D173G mutant

<400> SEQUENCE: 256

```
Met Glu Ser Lys Ile Ile Gly Lys Val Asn Phe Glu Glu His Leu Leu
1               5                   10                  15

Asp Lys Glu Leu Lys Leu Ile Asp Thr Phe Lys Phe Asn Asp Ser Tyr
            20                  25                  30

Ser Leu Tyr Ala Asn Gly Lys Trp Lys Thr Cys Met Leu Trp Asn Arg
        35                  40                  45

Ser Gly Gln Lys Asp Asp His Leu Ser Tyr Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Arg His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270
```

Pro Ile Asn Asn
275

<210> SEQ ID NO 257
<211> LENGTH: 831
<212> TYPE: DNA
<213> ORGANISM: Artificial Sequence
<220> FEATURE:
<223> OTHER INFORMATION: gene sequence of
E27K+E34L+S37N+I39K+I58Y+D173G+K123Q mutant

<400> SEQUENCE: 257
atggaatcca agatcatcgg taaagtcaac ttcgaggagc atctgctgga taaagagctg 60
aaactgatcg acactttcaa attcaacgac agctacagcc tgtacgctaa tggtaaatgg 120
aagacttgca tgctgtggaa ccgttctggt cagaaagatg accatctgtc ttatgaacat 180
gatacctacg tgaaacctac tgaatacggc aaacagctgg catacgtaaa cgaaatcatc 240
gctaacacct ttaagaaaga acacatcaag acggtgcgtc tgttcatgtg tatcaacggc 300
ctgatcatcc cacacaaaga ctacctggaa ttcaagaaag gcttcacccg tcgtcacatc 360
ccgctgcaga tcaacgaaca cgcactgacc tctgaagaag atgttgttta caacatgcag 420
aaaggtgaaa tttggttcat cgaaggccgt aaaatccaca gcgctgccaa tttcagcaaa 480
gtgaaacgta tcaacctggt catcgacttc gcgccggata ttccgtttga agaactgttc 540
ctgaattctg agaactatca accgaacctg atcccgaaaa tctctcaacg tacccagctg 600
aaagaagaag agctgggtta tatcaaaggt ctgtctaaaa ttatcaatga aatgaacttt 660
gacgacatcc tgtccattct gagcaaaatt cacttctatc gcaacgtttc ctccgaactg 720
gtttttggct ggctggacga aattgccacg gcgtccaaca actataacat tcagcgcaaa 780
gcgcaggaag taaccgatct gctgattcgc aaaggcccga ttaataacta a 831

<210> SEQ ID NO 258
<211> LENGTH: 276
<212> TYPE: PRT
<213> ORGANISM: Artificial Sequence
<220> FEATURE:
<223> OTHER INFORMATION: sequence of
E27K+E34L+S37N+I39K+I58Y+D173G+K123Q mutant

<400> SEQUENCE: 258

Met Glu Ser Lys Ile Ile Gly Lys Val Asn Phe Glu Glu His Leu Leu
1 5 10 15

Asp Lys Glu Leu Lys Leu Ile Asp Thr Phe Lys Phe Asn Asp Ser Tyr
20 25 30

Ser Leu Tyr Ala Asn Gly Lys Trp Lys Thr Cys Met Leu Trp Asn Arg
35 40 45

Ser Gly Gln Lys Asp Asp His Leu Ser Tyr Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys
100 105 110

Lys Gly Phe Thr Arg Arg His Ile Pro Leu Gln Ile Asn Glu His Ala
115 120 125

Leu Thr Ser Glu Glu Asp Val Val Tyr Asn Met Gln Lys Gly Glu Ile
130 135 140

```
Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Ile Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 259
<211> LENGTH: 831
<212> TYPE: DNA
<213> ORGANISM: Artificial Sequence
<220> FEATURE:
<223> OTHER INFORMATION: H14R+E27K+D30S+E34G+I39K+I98V+K106Q+K112E+I223V mutant

<400> SEQUENCE: 259

```
atggaatcca agatcatcgg taaagtcaac ttcgaggagc gtctgctgga taaagagctg     60

aaactgatcg acactttcaa attcaacagc agctacagcg gttacgcttc tggtaaatgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tgttaacggc    300

ctgatcatcc cacaccagga ctacctggaa ttcgaaaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacgttc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 260
<211> LENGTH: 276
<212> TYPE: PRT
<213> ORGANISM: Artificial Sequence
<220> FEATURE:
<223> OTHER INFORMATION: H14R+E27K+D30S+E34G+I39K+I98V+K106Q+K112E+I223V mutant

<400> SEQUENCE: 260

```
Met Glu Ser Lys Ile Ile Gly Lys Val Asn Phe Glu Glu Arg Leu Leu
```

-continued

```
1               5                   10                  15

Asp Lys Glu Leu Lys Leu Ile Asp Thr Phe Lys Phe Asn Ser Ser Tyr
            20                  25                  30

Ser Gly Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Val Asn Gly Leu Ile Ile Pro His Gln Asp Tyr Leu Glu Phe Glu
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 261
<211> LENGTH: 831
<212> TYPE: DNA
<213> ORGANISM: Artificial Sequence
<220> FEATURE:
<223> OTHER INFORMATION: H14R+E27K+E34N+I39K+I98V+K106Q+K112E+I223V
      mutant

<400> SEQUENCE: 261

atggaatcca agatcatcgg taaagtcaac ttcgaggagc gtctgctgga taaagagctg      60

aaactgatcg acactttcaa attcaacgac agctacagca attacgcttc tggtaaatgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tgttaacggc     300

ctgatcatcc cacaccagga ctacctggaa ttcgaaaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480
```

```
gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacgttc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a            831
```

```
<210> SEQ ID NO 262
<211> LENGTH: 276
<212> TYPE: PRT
<213> ORGANISM: Artificial Sequence
<220> FEATURE:
<223> OTHER INFORMATION: H14R+E27K+E34N+I39K+I98V+K106Q+K112E+I223V
      mutant

<400> SEQUENCE: 262

Met Glu Ser Lys Ile Ile Gly Lys Val Asn Phe Glu Glu Arg Leu Leu
1               5                   10                  15

Asp Lys Glu Leu Lys Leu Ile Asp Thr Phe Lys Phe Asn Asp Ser Tyr
            20                  25                  30

Ser Asn Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Val Asn Gly Leu Ile Ile Pro His Gln Asp Tyr Leu Glu Phe Glu
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 263
<211> LENGTH: 831
<212> TYPE: DNA
<213> ORGANISM: Artificial Sequence
<220> FEATURE:
<223> OTHER INFORMATION: H14R+E27K+E34G+I39K+I98V+K106Q+K112E+I223V
mutant

<400> SEQUENCE: 263

```
atggaatcca agatcatcgg taaagtcaac ttcgaggagc gtctgctgga taaagagctg     60

aaactgatcg acactttcaa attcaacgac agctacagcg gttacgcttc tggtaaatgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tgttaacggc    300

ctgatcatcc cacaccagga ctacctggaa ttcgaaaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacgttc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 264
<211> LENGTH: 276
<212> TYPE: PRT
<213> ORGANISM: Artificial Sequence
<220> FEATURE:
<223> OTHER INFORMATION: H14R+E27K+E34G+I39K+I98V+K106Q+K112E+I223V
mutant

<400> SEQUENCE: 264

```
Met Glu Ser Lys Ile Ile Gly Lys Val Asn Phe Glu Glu Arg Leu Leu
1               5                   10                  15

Asp Lys Glu Leu Lys Leu Ile Asp Thr Phe Lys Phe Asn Asp Ser Tyr
            20                  25                  30

Ser Gly Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Val Asn Gly Leu Ile Ile Pro His Gln Asp Tyr Leu Glu Phe Glu
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160
```

```
Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 265
<211> LENGTH: 831
<212> TYPE: DNA
<213> ORGANISM: Artificial Sequence
<220> FEATURE:
<223> OTHER INFORMATION: H14R+E27K+E34G+S37W+I39K+I98V+K106Q+K112E+I223V
      mutant

<400> SEQUENCE: 265

atggaatcca agatcatcgg taaagtcaac ttcgaggagc gtctgctgga taaagagctg      60

aaactgatcg acactttcaa attcaacgac agctacagcg gttacgcttg ggtaaatgg      120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tgttaacggc     300

ctgatcatcc cacaccagga ctacctggaa ttcgaaaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacgttc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 266
<211> LENGTH: 276
<212> TYPE: PRT
<213> ORGANISM: Artificial Sequence
<220> FEATURE:
<223> OTHER INFORMATION: H14R+E27K+E34G+S37W+I39K+I98V+K106Q+K112E+I223V
      mutant

<400> SEQUENCE: 266

Met Glu Ser Lys Ile Ile Gly Lys Val Asn Phe Glu Glu Arg Leu Leu
1               5                   10                  15

Asp Lys Glu Leu Lys Leu Ile Asp Thr Phe Lys Phe Asn Asp Ser Tyr
            20                  25                  30
```

```
Ser Gly Tyr Ala Trp Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Val Asn Gly Leu Ile Ile Pro His Gln Asp Tyr Leu Glu Phe Glu
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 267
<211> LENGTH: 831
<212> TYPE: DNA
<213> ORGANISM: Artificial Sequence
<220> FEATURE:
<223> OTHER INFORMATION: H14R+E27K+E34G+S37F+I39K+I98V+K106Q+K112E+I223V
      mutant

<400> SEQUENCE: 267

```
atggaatcca agatcatcgg taaagtcaac ttcgaggagc gtctgctgga taaagagctg      60

aaactgatcg acactttcaa attcaacgac agctacagcg gttacgcttt tggtaaatgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tgttaacggc     300

ctgatcatcc cacaccagga ctacctggaa ttcgaaaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600
```

```
aaagaagaag agctgggtta tatcaaaggt ctgtctaaaa ttatcaatga aatgaacttt    660

gacgacgttc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 268
<211> LENGTH: 276
<212> TYPE: PRT
<213> ORGANISM: Artificial Sequence
<220> FEATURE:
<223> OTHER INFORMATION: H14R+E27K+E34G+S37F+I39K+I98V+K106Q+K112E+I223V
      mutant

<400> SEQUENCE: 268

```
Met Glu Ser Lys Ile Ile Gly Lys Val Asn Phe Glu Glu Arg Leu Leu
1               5                   10                  15

Asp Lys Glu Leu Lys Leu Ile Asp Thr Phe Lys Phe Asn Asp Ser Tyr
            20                  25                  30

Ser Gly Tyr Ala Phe Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Val Asn Gly Leu Ile Ile Pro His Gln Asp Tyr Leu Glu Phe Glu
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 269
<211> LENGTH: 831
<212> TYPE: DNA
<213> ORGANISM: Artificial Sequence
<220> FEATURE:
<223> OTHER INFORMATION: H14R+E27K+E34G+S37E+I39K+I98V+K106Q+K112E+I223V
      mutant

<400> SEQUENCE: 269

```
atggaatcca agatcatcgg taaagtcaac ttcgaggagc gtctgctgga taaagagctg      60

aaactgatcg acactttcaa attcaacgac agctacagcg gttacgctga aggtaaatgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tgttaacggc     300

ctgatcatcc cacaccagga ctacctggaa ttcgaaaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacgttc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831
```

<210> SEQ ID NO 270
<211> LENGTH: 276
<212> TYPE: PRT
<213> ORGANISM: Artificial Sequence
<220> FEATURE:
<223> OTHER INFORMATION: H14R+E27K+E34G+S37E+I39K+I98V+K106Q+K112E+I223V
      mutant

<400> SEQUENCE: 270

```
Met Glu Ser Lys Ile Ile Gly Lys Val Asn Phe Glu Glu Arg Leu Leu
1               5                   10                  15

Asp Lys Glu Leu Lys Leu Ile Asp Thr Phe Lys Phe Asn Asp Ser Tyr
            20                  25                  30

Ser Gly Tyr Ala Glu Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Val Asn Gly Leu Ile Ile Pro His Gln Asp Tyr Leu Glu Phe Glu
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
```

```
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

```
<210> SEQ ID NO 271
<211> LENGTH: 831
<212> TYPE: DNA
<213> ORGANISM: Artificial Sequence
<220> FEATURE:
<223> OTHER INFORMATION: H14R+E27K+E34G+Y35K+I39K+I98V+K106Q+K112E+I223V
      mutant

<400> SEQUENCE: 271

atggaatcca agatcatcgg taaagtcaac ttcgaggagc gtctgctgga taaagagctg      60

aaactgatcg acactttcaa attcaacgac agctacagcg gtaaagcttc tggtaaatgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tgttaacggc     300

ctgatcatcc cacaccagga ctacctggaa ttcgaaaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacgttc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831

<210> SEQ ID NO 272
<211> LENGTH: 276
<212> TYPE: PRT
<213> ORGANISM: Artificial Sequence
<220> FEATURE:
<223> OTHER INFORMATION: H14R+E27K+E34G+Y35K+I39K+I98V+K106Q+K112E+I223V
      mutant

<400> SEQUENCE: 272

Met Glu Ser Lys Ile Ile Gly Lys Val Asn Phe Glu Glu Arg Leu Leu
1               5                   10                  15

Asp Lys Glu Leu Lys Leu Ile Asp Thr Phe Lys Phe Asn Asp Ser Tyr
            20                  25                  30

Ser Gly Lys Ala Ser Gly Lys Trp Lys Thr Cys Met Leu Trp Asn Arg
        35                  40                  45
```

-continued

```
Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Val Asn Gly Leu Ile Ile Pro His Gln Asp Tyr Leu Glu Phe Glu
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 273
<211> LENGTH: 831
<212> TYPE: DNA
<213> ORGANISM: Artificial Sequence
<220> FEATURE:
<223> OTHER INFORMATION: H14R+E27K+E34G+S37N+I39K+I98V+K106Q+K112E+I223V mutant

<400> SEQUENCE: 273

```
atggaatcca agatcatcgg taaagtcaac ttcgaggagc gtctgctgga taaagagctg     60

aaactgatcg acactttcaa attcaacgac agctacagcg gttacgctaa tggtaaatgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tgttaacggc    300

ctgatcatcc cacaccagga ctacctggaa ttcgaaaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacgttc tgtccattct gagcaaaatt cacttctatc gcaacgtttc ctccgaactg    720
```

```
gtttttggct ggctggacga aattgccacg gcgtccaaca actataacat tcagcgcaaa    780

gcgcaggaag taaccgatct gctgattcgc aaaggcccga ttaataacta a             831


<210> SEQ ID NO 274
<211> LENGTH: 276
<212> TYPE: PRT
<213> ORGANISM: Artificial Sequence
<220> FEATURE:
<223> OTHER INFORMATION: H14R+E27K+E34G+S37N+I39K+I98V+K106Q+K112E+I223V
      mutant

<400> SEQUENCE: 274

Met Glu Ser Lys Ile Ile Gly Lys Val Asn Phe Glu Glu Arg Leu Leu
1               5                   10                  15

Asp Lys Glu Leu Lys Leu Ile Asp Thr Phe Lys Phe Asn Asp Ser Tyr
            20                  25                  30

Ser Gly Tyr Ala Asn Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Val Asn Gly Leu Ile Ile Pro His Gln Asp Tyr Leu Glu Phe Glu
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 275
<211> LENGTH: 831
<212> TYPE: DNA
<213> ORGANISM: Artificial Sequence
<220> FEATURE:
<223> OTHER INFORMATION:
      H14R+E27K+E34G+I39K+I98V+K106Q+K112E+K123Q+I223V mutant
```

<400> SEQUENCE: 275

```
atggaatcca agatcatcgg taaagtcaac ttcgaggagc gtctgctgga taaagagctg     60
aaactgatcg acactttcaa attcaacgac agctacagcg gttacgcttc tggtaaatgg    120
aagacttgca tgctgtggaa ccgttctggt cagaaagatg accatctgtc tattgaacat    180
gatacctacg tgaaacctac tgaatacggc aaacagctgg catacgtaaa cgaaatcatc    240
gctaacacct ttaagaaaga acacatcaag acggtgcgtc tgttcatgtg tgttaacggc    300
ctgatcatcc cacaccagga ctacctggaa ttcgaaaaag gcttcacccg tatccacatc    360
ccgctgcaaa tcaacgaaca cgcactgacc tctgaagaag atgttgttta caacatgcag    420
aaaggtgaaa tttggttcat cgaaggccgt aaaatccaca gcgctgccaa tttcagcaaa    480
gtgaaacgta tcaacctggt catcgacttc gcgccggata ttccgtttga agaactgttc    540
ctgaattctg agaactatca accgaacctg atcccgaaaa tctctcaacg tacccagctg    600
aaagaagaag agctgggtta tatcaaaggt ctgtctaaaa ttatcaatga aatgaacttt    660
gacgacgttc tgtccattct gagcaaaatt cacttctatc gcaacgtttc ctccgaactg    720
gtttttggct ggctggacga aattgccacg gcgtccaaca actataacat tcagcgcaaa    780
gcgcaggaag taaccgatct gctgattcgc aaaggcccga ttaataacta a             831
```

<210> SEQ ID NO 276
<211> LENGTH: 276
<212> TYPE: PRT
<213> ORGANISM: Artificial Sequence
<220> FEATURE:
<223> OTHER INFORMATION:
H14R+E27K+E34G+I39K+I98V+K106Q+K112E+K123Q+I223V mutant

<400> SEQUENCE: 276

```
Met Glu Ser Lys Ile Ile Gly Lys Val Asn Phe Glu Glu Arg Leu Leu
1               5                   10                  15

Asp Lys Glu Leu Lys Leu Ile Asp Thr Phe Lys Phe Asn Asp Ser Tyr
            20                  25                  30

Ser Gly Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Val Asn Gly Leu Ile Ile Pro His Gln Asp Tyr Leu Glu Phe Glu
            100                 105                 110

Lys Gly Phe Thr Arg Ile His Ile Pro Leu Gln Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205
```

```
Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 277
<211> LENGTH: 831
<212> TYPE: DNA
<213> ORGANISM: Artificial Sequence
<220> FEATURE:
<223> OTHER INFORMATION:
      H14R+E27K+E34G+I39K+I98V+K106Q+K112E+K123S+I223V mutant

<400> SEQUENCE: 277

atggaatcca agatcatcgg taaagtcaac ttcgaggagc gtctgctgga taaagagctg      60

aaactgatcg acactttcaa attcaacgac agctacagcg gttacgcttc tggtaaatgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tgttaacggc     300

ctgatcatcc cacaccagga ctacctggaa ttcgaaaaag gcttcacccg tatccacatc     360

ccgctgagca tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacgttc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831


<210> SEQ ID NO 278
<211> LENGTH: 276
<212> TYPE: PRT
<213> ORGANISM: Artificial Sequence
<220> FEATURE:
<223> OTHER INFORMATION:
      H14R+E27K+E34G+I39K+I98V+K106Q+K112E+K123S+I223V mutant

<400> SEQUENCE: 278

Met Glu Ser Lys Ile Ile Gly Lys Val Asn Phe Glu Glu Arg Leu Leu
1               5                   10                  15

Asp Lys Glu Leu Lys Leu Ile Asp Thr Phe Lys Phe Asn Asp Ser Tyr
            20                  25                  30

Ser Gly Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
```

```
65                  70                  75                  80

Ala Asn Thr Phe Lys Lys Glu His Ile Lys Thr Val Arg Leu Phe Met
                85                  90                  95

Cys Val Asn Gly Leu Ile Ile Pro His Gln Asp Tyr Leu Glu Phe Glu
            100                 105                 110

Lys Gly Phe Thr Arg Ile His Ile Pro Leu Ser Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 279
<211> LENGTH: 831
<212> TYPE: DNA
<213> ORGANISM: Artificial Sequence
<220> FEATURE:
<223> OTHER INFORMATION: H14R+E27K+E34G+I39K+I58A+I98V+K106Q+K112E+I223V
      mutant

<400> SEQUENCE: 279

atggaatcca agatcatcgg taaagtcaac ttcgaggagc gtctgctgga taaagagctg     60

aaactgatcg acactttcaa attcaacgac agctacagcg gttacgcttc tggtaaatgg    120

aagacttgca tgctgtggaa ccgttctggt cagaaagatg accatctgtc tgcagaacat    180

gatacctacg tgaaacctac tgaatacggc aaacagctgg catacgtaaa cgaaatcatc    240

gctaacacct ttaagaaaga acacatcaag acggtgcgtc tgttcatgtg tgttaacggc    300

ctgatcatcc cacaccagga ctacctggaa ttcgaaaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacgttc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 280
<211> LENGTH: 276
<212> TYPE: PRT
<213> ORGANISM: Artificial Sequence
<220> FEATURE:
<223> OTHER INFORMATION: H14R+E27K+E34G+I39K+I58A+I98V+K106Q+K112E+I223V
mutant

<400> SEQUENCE: 280

```
Met Glu Ser Lys Ile Ile Gly Lys Val Asn Phe Glu Glu Arg Leu Leu
1               5                   10                  15

Asp Lys Glu Leu Lys Leu Ile Asp Thr Phe Lys Phe Asn Asp Ser Tyr
            20                  25                  30

Ser Gly Tyr Ala Ser Gly Lys Trp Lys Thr Cys Met Leu Trp Asn Arg
        35                  40                  45

Ser Gly Gln Lys Asp Asp His Leu Ser Ala Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Val Asn Gly Leu Ile Ile Pro His Gln Asp Tyr Leu Glu Phe Glu
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 281
<211> LENGTH: 831
<212> TYPE: DNA
<213> ORGANISM: Artificial Sequence
<220> FEATURE:
<223> OTHER INFORMATION:
H14R+E27K+E34G+I39K+I98V+K106Q+K112E+I118F+I223V mutant

<400> SEQUENCE: 281

```
atggaatcca agatcatcgg taaagtcaac ttcgaggagc gtctgctgga taaagagctg     60
```

-continued

```
aaactgatcg acactttcaa attcaacgac agctacagcg gttacgcttc tggtaaatgg    120

aagacttgca tgctgtggaa ccgttctggt cagaaagatg accatctgtc tattgaacat    180

gatacctacg tgaaacctac tgaatacggc aaacagctgg catacgtaaa cgaaatcatc    240

gctaacacct ttaagaaaga acacatcaag acggtgcgtc tgttcatgtg tgttaacggc    300

ctgatcatcc cacaccagga ctacctggaa ttcgaaaaag gcttcacccg tttccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacgttc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

```
<210> SEQ ID NO 282
<211> LENGTH: 276
<212> TYPE: PRT
<213> ORGANISM: Artificial Sequence
<220> FEATURE:
<223> OTHER INFORMATION:
      H14R+E27K+E34G+I39K+I98V+K106Q+K112E+I118F+I223V mutant

<400> SEQUENCE: 282

Met Glu Ser Lys Ile Ile Gly Lys Val Asn Phe Glu Glu Arg Leu Leu
1               5                   10                  15

Asp Lys Glu Leu Lys Leu Ile Asp Thr Phe Lys Phe Asn Asp Ser Tyr
            20                  25                  30

Ser Gly Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Val Asn Gly Leu Ile Ile Pro His Gln Asp Tyr Leu Glu Phe Glu
            100                 105                 110

Lys Gly Phe Thr Arg Phe His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220
```

```
Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 283
<211> LENGTH: 831
<212> TYPE: DNA
<213> ORGANISM: Artificial Sequence
<220> FEATURE:
<223> OTHER INFORMATION: H14R+E27K+E34G+S37T+I39K+I98V+K106Q+K112E+I223V mutant

<400> SEQUENCE: 283

```
atggaatcca agatcatcgg taaagtcaac ttcgaggagc gtctgctgga taaagagctg      60

aaactgatcg acactttcaa attcaacgac agctacagcg gttacgctac cggtaaatgg     120

aagacttgca tgctgtggaa ccgttctggt cagaaagatg accatctgtc tattgaacat     180

gatacctacg tgaaacctac tgaatacggc aaacagctgg catacgtaaa cgaaatcatc     240

gctaacacct ttaagaaaga acacatcaag acggtgcgtc tgttcatgtg tgttaacggc     300

ctgatcatcc cacaccagga ctacctggaa ttcgaaaaag gcttcacccg tatccacatc     360

ccgctgaaaa tcaacgaaca cgcactgacc tctgaagaag atgttgttta caacatgcag     420

aaaggtgaaa tttggttcat cgaaggccgt aaaatccaca gcgctgccaa tttcagcaaa     480

gtgaaacgta tcaacctggt catcgacttc gcgccggata ttccgtttga agaactgttc     540

ctgaattctg agaactatca accgaacctg atcccgaaaa tctctcaacg tacccagctg     600

aaagaagaag agctgggtta tatcaaaggt ctgtctaaaa ttatcaatga aatgaacttt     660

gacgacgttc tgtccattct gagcaaaatt cacttctatc gcaacgtttc ctccgaactg     720

gtttttggct ggctggacga aattgccacg gcgtccaaca actataacat tcagcgcaaa     780

gcgcaggaag taaccgatct gctgattcgc aaaggcccga ttaataacta a              831
```

<210> SEQ ID NO 284
<211> LENGTH: 276
<212> TYPE: PRT
<213> ORGANISM: Artificial Sequence
<220> FEATURE:
<223> OTHER INFORMATION: H14R+E27K+E34G+S37T+I39K+I98V+K106Q+K112E+I223V mutant

<400> SEQUENCE: 284

```
Met Glu Ser Lys Ile Ile Gly Lys Val Asn Phe Glu Glu Arg Leu Leu
1               5                   10                  15

Asp Lys Glu Leu Lys Leu Ile Asp Thr Phe Lys Phe Asn Asp Ser Tyr
            20                  25                  30

Ser Gly Tyr Ala Thr Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95
```

```
Cys Val Asn Gly Leu Ile Ile Pro His Gln Asp Tyr Leu Glu Phe Glu
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 285
<211> LENGTH: 831
<212> TYPE: DNA
<213> ORGANISM: Artificial Sequence
<220> FEATURE:
<223> OTHER INFORMATION: H14R+E27K+E34G+I39K+I58V+I98V+K106Q+K112E+I223V
      mutant

<400> SEQUENCE: 285

```
atggaatcca agatcatcgg taaagtcaac ttcgaggagc gtctgctgga taaagagctg     60

aaactgatcg acactttcaa attcaacgac agctacagcg gttacgcttc tggtaaatgg    120

aagacttgca tgctgtggaa ccgttctggt cagaaagatg accatctgtc tgttgaacat    180

gatacctacg tgaaacctac tgaatacggc aaacagctgg catacgtaaa cgaaatcatc    240

gctaacacct ttaagaaaga acacatcaag acggtgcgtc tgttcatgtg tgttaacggc    300

ctgatcatcc cacaccagga ctacctggaa ttcgaaaaag gcttcacccg tatccacatc    360

ccgctgaaaa tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacgttc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831
```

<210> SEQ ID NO 286
<211> LENGTH: 276

<212> TYPE: PRT
<213> ORGANISM: Artificial Sequence
<220> FEATURE:
<223> OTHER INFORMATION: H14R+E27K+E34G+I39K+I58V+I98V+K106Q+K112E+I223V
      mutant

<400> SEQUENCE: 286

```
Met Glu Ser Lys Ile Ile Gly Lys Val Asn Phe Glu Glu Arg Leu Leu
1               5                   10                  15

Asp Lys Glu Leu Lys Leu Ile Asp Thr Phe Lys Phe Asn Asp Ser Tyr
            20                  25                  30

Ser Gly Tyr Ala Ser Gly Lys Trp Lys Thr Cys Met Leu Trp Asn Arg
        35                  40                  45

Ser Gly Gln Lys Asp Asp His Leu Ser Val Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Val Asn Gly Leu Ile Ile Pro His Gln Asp Tyr Leu Glu Phe Glu
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
                245                 250                 255

Ile Gln Arg Lys Ala Gln Glu Val Thr Asp Leu Leu Ile Arg Lys Gly
            260                 265                 270

Pro Ile Asn Asn
        275
```

<210> SEQ ID NO 287
<211> LENGTH: 831
<212> TYPE: DNA
<213> ORGANISM: Artificial Sequence
<220> FEATURE:
<223> OTHER INFORMATION:
      H14R+E27K+E34G+I39K+I98V+K106Q+K112E+K123I+I223V mutant

<400> SEQUENCE: 287

```
atggaatcca agatcatcgg taaagtcaac ttcgaggagc gtctgctgga taaagagctg      60

aaactgatcg acactttcaa attcaacgac agctacagcg gttacgcttc tggtaaatgg     120

aagacttgca tgctgtggaa ccgttctggt cagaaagatg accatctgtc tattgaacat     180
```

```
gatacctacg tgaaacctac tgaatacggc aaacagctgg catacgtaaa cgaaatcatc    240

gctaacacct ttaagaaaga acacatcaag acggtgcgtc tgttcatgtg tgttaacggc    300

ctgatcatcc cacaccagga ctacctggaa ttcgaaaaag gcttcacccg tatccacatc    360

ccgctgatta tcaacgaaca cgcactgacc tctgaagaag atgttgttta caacatgcag    420

aaaggtgaaa tttggttcat cgaaggccgt aaaatccaca gcgctgccaa tttcagcaaa    480

gtgaaacgta tcaacctggt catcgacttc gcgccggata ttccgtttga agaactgttc    540

ctgaattctg agaactatca accgaacctg atcccgaaaa tctctcaacg tacccagctg    600

aaagaagaag agctgggtta tatcaaaggt ctgtctaaaa ttatcaatga aatgaacttt    660

gacgacgttc tgtccattct gagcaaaatt cacttctatc gcaacgtttc ctccgaactg    720

gtttttggct ggctggacga aattgccacg gcgtccaaca actataacat tcagcgcaaa    780

gcgcaggaag taaccgatct gctgattcgc aaaggcccga ttaataacta a             831


<210> SEQ ID NO 288
<211> LENGTH: 276
<212> TYPE: PRT
<213> ORGANISM: Artificial Sequence
<220> FEATURE:
<223> OTHER INFORMATION:
      H14R+E27K+E34G+I39K+I98V+K106Q+K112E+K123I+I223V mutant

<400> SEQUENCE: 288

Met Glu Ser Lys Ile Ile Gly Lys Val Asn Phe Glu Glu Arg Leu Leu
1               5                   10                  15

Asp Lys Glu Leu Lys Leu Ile Asp Thr Phe Lys Phe Asn Asp Ser Tyr
            20                  25                  30

Ser Gly Tyr Ala Ser Gly Lys Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Val Asn Gly Leu Ile Ile Pro His Gln Asp Tyr Leu Glu Phe Glu
            100                 105                 110

Lys Gly Phe Thr Arg Ile His Ile Pro Leu Ile Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Thr Gln Leu Lys Glu Glu Glu Leu Gly Tyr Ile
        195                 200                 205

Lys Gly Leu Ser Lys Ile Ile Asn Glu Met Asn Phe Asp Asp Val Leu
    210                 215                 220

Ser Ile Leu Ser Lys Ile His Phe Tyr Arg Asn Val Ser Ser Glu Leu
225                 230                 235                 240

Val Phe Gly Trp Leu Asp Glu Ile Ala Thr Ala Ser Asn Asn Tyr Asn
```

```
                245                 250                 255

Ile Gln Arg Lys Ala Gln Glu Val Thr Asp Leu Leu Ile Arg Lys Gly
            260                 265                 270

Pro Ile Asn Asn
        275


<210> SEQ ID NO 289
<211> LENGTH: 280
<212> TYPE: PRT
<213> ORGANISM: Artificial Sequence
<220> FEATURE:
<223> OTHER INFORMATION: amino acid sequence of PH1

<400> SEQUENCE: 289

Met Glu Ser Lys Ile Ile Gly Lys Val Asn Phe Glu Glu His Leu Leu
1               5                   10                  15

Asp Lys Glu Leu Lys Leu Ile Asp Thr Phe Glu Phe Asn Asp Ser Tyr
            20                  25                  30

Ser Glu Tyr Ala Ser Gly Ile Trp Lys Thr Cys Met Leu Trp Asn Arg
        35                  40                  45

Ser Gly Gln Lys Asp Asp His Leu Ser Ile Glu His Asp Thr Tyr Val
    50                  55                  60

Lys Pro Thr Glu Tyr Gly Lys Gln Leu Ala Tyr Val Asn Glu Ile Ile
65                  70                  75                  80

Ala Asn Thr Phe Lys Lys Glu His Ile Lys Thr Val Arg Leu Phe Met
                85                  90                  95

Cys Ile Asn Gly Leu Ile Ile Pro His Lys Asp Tyr Leu Glu Phe Lys
            100                 105                 110

Lys Gly Phe Thr Arg Ile His Ile Pro Leu Lys Ile Asn Glu His Ala
        115                 120                 125

Leu Thr Ser Glu Glu Asp Val Val Tyr Asn Met Gln Lys Gly Glu Ile
    130                 135                 140

Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Lys Glu Leu Thr Asp Glu Val Ile Glu Gly Ile
        195                 200                 205

Leu Gly Phe Ser Ile Ile Ile Ser Glu Ala Asn Tyr Arg Glu Ile Val
    210                 215                 220

Ser Ile Leu Ala Lys Leu His Phe Phe Tyr Lys Ala Asp Cys Arg Ser
225                 230                 235                 240

Met Tyr Asp Trp Leu Lys Glu Ile Cys Lys Arg Arg Gly Asp Pro Ala
                245                 250                 255

Leu Ile Glu Lys Thr Ala Ser Leu Glu Arg Phe Phe Leu Gly His Arg
            260                 265                 270

Glu Arg Gly Glu Val Met Thr Tyr
        275                 280


<210> SEQ ID NO 290
<211> LENGTH: 276
<212> TYPE: PRT
<213> ORGANISM: Artificial Sequence
<220> FEATURE:
<223> OTHER INFORMATION: amino acid sequence of I39K+S33N
```

<400> SEQUENCE: 290

Met Glu Ser Lys Ile Ile Gly Lys Val Asn Phe Glu Glu His Leu Leu
1 5 10 15

Asp Lys Glu Leu Lys Leu Ile Asp Thr Phe Glu Phe Asn Asp Ser Tyr
20 25 30

Asn Glu Tyr Ala Ser Gly Lys Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys
100 105 110

Lys Gly Phe Thr Arg Ile His Ile Pro Leu Lys Ile Asn Glu His Ala
115 120 125

Leu Thr Ser Glu Glu Asp Val Val Tyr Asn Met Gln Lys Gly Glu Ile
130 135 140

Trp Phe Ile Glu Gly Arg Lys Ile His Ser Ala Ala Asn Phe Ser Lys
145 150 155 160

Val Lys Arg Ile Asn Leu Val Ile Asp Phe Ala Pro Asp Ile Pro Phe
165 170 175

Glu Glu Leu Phe Leu Asn Ser Glu Asn Tyr Gln Pro Asn Leu Ile Pro
180 185 190

Lys Ile Ser Gln Arg Thr Gln Leu Lys Glu Glu Glu Leu Gly Tyr Ile
195 200 205

Lys Gly Leu Ser Lys Ile Ile Asn Glu Met Asn Phe Asp Asp Ile Leu
210 215 220

Ser Ile Leu Ser Lys Ile His Phe Tyr Arg Asn Val Ser Ser Glu Leu
225 230 235 240

Val Phe Gly Trp Leu Asp Glu Ile Ala Thr Ala Ser Asn Asn Tyr Asn
245 250 255

Ile Gln Arg Lys Ala Gln Glu Val Thr Asp Leu Leu Ile Arg Lys Gly
260 265 270

Pro Ile Asn Asn
275

<210> SEQ ID NO 291
<211> LENGTH: 276
<212> TYPE: PRT
<213> ORGANISM: Artificial Sequence
<220> FEATURE:
<223> OTHER INFORMATION: amino acid sequence of E27K+I39K+F28L+S31A

<400> SEQUENCE: 291

Met Glu Ser Lys Ile Ile Gly Lys Val Asn Phe Glu Glu His Leu Leu
1 5 10 15

Asp Lys Glu Leu Lys Leu Ile Asp Thr Phe Lys Leu Asn Asp Ala Tyr
20 25 30

Ser Glu Tyr Ala Ser Gly Arg Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys
100 105 110

Lys Gly Phe Thr Arg Ile His Ile Pro Leu Lys Ile Asn Glu His Ala
115 120 125

Leu Thr Ser Glu Glu Asp Val Val Tyr Asn Met Gln Lys Gly Glu Ile
130 135 140

Trp Phe Ile Glu Gly Arg Lys Ile His Ser Ala Ala Asn Phe Ser Lys
145 150 155 160

Val Lys Arg Ile Asn Leu Val Ile Asp Phe Ala Pro Asp Ile Pro Phe
165 170 175

Glu Glu Leu Phe Leu Asn Ser Glu Asn Tyr Gln Pro Asn Leu Ile Pro
180 185 190

Lys Ile Ser Gln Arg Thr Gln Leu Lys Glu Glu Glu Leu Gly Tyr Ile
195 200 205

Lys Gly Leu Ser Lys Ile Ile Asn Glu Met Asn Phe Asp Asp Ile Leu
210 215 220

Ser Ile Leu Ser Lys Ile His Phe Tyr Arg Asn Val Ser Ser Glu Leu
225 230 235 240

Val Phe Gly Trp Leu Asp Glu Ile Ala Thr Ala Ser Asn Asn Tyr Asn
245 250 255

Ile Gln Arg Lys Ala Gln Glu Val Thr Asp Leu Leu Ile Arg Lys Gly
260 265 270

Pro Ile Asn Asn
275

<210> SEQ ID NO 292
<211> LENGTH: 280
<212> TYPE: PRT
<213> ORGANISM: Artificial Sequence
<220> FEATURE:
<223> OTHER INFORMATION: amino acid sequence of PH1 mutant with E27K
mutation

<400> SEQUENCE: 292

Met Glu Ser Lys Ile Ile Gly Lys Val Asn Phe Glu Glu His Leu Leu
1 5 10 15

Asp Lys Glu Leu Lys Leu Ile Asp Thr Phe Lys Phe Asn Asp Ser Tyr
20 25 30

Ser Glu Tyr Ala Ser Gly Ile Trp Lys Thr Cys Met Leu Trp Asn Arg
35 40 45

Ser Gly Gln Lys Asp Asp His Leu Ser Ile Glu His Asp Thr Tyr Val
50 55 60

Lys Pro Thr Glu Tyr Gly Lys Gln Leu Ala Tyr Val Asn Glu Ile Ile
65 70 75 80

Ala Asn Thr Phe Lys Lys Glu His Ile Lys Thr Val Arg Leu Phe Met
85 90 95

Cys Ile Asn Gly Leu Ile Ile Pro His Lys Asp Tyr Leu Glu Phe Lys
100 105 110

Lys Gly Phe Thr Arg Ile His Ile Pro Leu Lys Ile Asn Glu His Ala
115 120 125

Leu Thr Ser Glu Glu Asp Val Val Tyr Asn Met Gln Lys Gly Glu Ile
130 135 140

-continued

```
Trp Phe Ile Glu Gly Arg Lys Ile His Ser Ala Ala Asn Phe Ser Lys
145                 150                 155                 160

Val Lys Arg Ile Asn Leu Val Ile Asp Phe Ala Pro Asp Ile Pro Phe
                165                 170                 175

Glu Glu Leu Phe Leu Asn Ser Glu Asn Tyr Gln Pro Asn Leu Ile Pro
            180                 185                 190

Lys Ile Ser Gln Arg Lys Glu Leu Thr Asp Glu Val Ile Glu Gly Ile
        195                 200                 205

Leu Gly Phe Ser Ile Ile Ile Ser Glu Ala Asn Tyr Arg Glu Ile Val
    210                 215                 220

Ser Ile Leu Ala Lys Leu His Phe Phe Tyr Lys Ala Asp Cys Arg Ser
225                 230                 235                 240

Met Tyr Asp Trp Leu Lys Glu Ile Cys Lys Arg Arg Gly Asp Pro Ala
                245                 250                 255

Leu Ile Glu Lys Thr Ala Ser Leu Glu Arg Phe Phe Leu Gly His Arg
            260                 265                 270

Glu Arg Gly Glu Val Met Thr Tyr
        275                 280
```